United States Patent
Trauthen et al.

(10) Patent No.: US 6,491,619 B1
(45) Date of Patent: Dec. 10, 2002

(54) RADIATION DELIVERY CATHETERS AND DOSIMETRY METHODS

(75) Inventors: Brett Trauthen, Newport Beach, CA (US); Lisa Tam, Lake Forest, CA (US); Robert Fazio, Yorba Linda, CA (US); Michael Crocker, Anaheim, CA (US); Edward F. Smith, Los Flores, CA (US); Gary Strathern, Santa Monica, CA (US)

(73) Assignee: Endologix, Inc, Irvine, CA (US)

( * ) Notice: Subject to any disclaimer, the term of this patent is extended or adjusted under 35 U.S.C. 154(b) by 59 days.

(21) Appl. No.: 09/648,563

(22) Filed: Aug. 25, 2000

Related U.S. Application Data

(63) Continuation-in-part of application No. 09/382,302, filed on Aug. 24, 1999, which is a continuation-in-part of application No. 09/256,337, filed on Feb. 19, 1999, now Pat. No. 6,287,249, which is a continuation-in-part of application No. 09/025,921, filed on Feb. 19, 1998, now abandoned, application No. 09/648,563, which is a continuation-in-part of application No. 09/119,828, filed on Apr. 5, 2000, now Pat. No. 6,176,821, which is a continuation of application No. 08/789,969, filed on Jan. 31, 1997, now Pat. No. 5,782,742.

(51) Int. Cl.[7] .................................................. A61N 5/00
(52) U.S. Cl. ............................................................. 600/3
(58) Field of Search ............................ 600/3; 604/103; 623/1.42, 1.21; 606/198, 1; 427/5

(56) References Cited

U.S. PATENT DOCUMENTS

| | | |
|---|---|---|
| 3,324,847 A | 6/1967 | Zoumboulis |
| 4,115,536 A | 9/1978 | Rothman et al. |
| 4,124,705 A | 11/1978 | Rothman et al. |
| 4,126,669 A | 11/1978 | Rothman et al. |
| 4,225,790 A | 9/1980 | Parsons, Jr. et al. |
| 4,323,055 A | 4/1982 | Kubiatowicz |
| 4,423,725 A | 1/1984 | Baran et al. |
| 4,581,017 A | 4/1986 | Sahota |
| 4,588,395 A | 5/1986 | Lemelson |
| 4,655,771 A | 4/1987 | Wallsten |
| 4,674,480 A | 6/1987 | Lemelson |
| 4,706,652 A | 11/1987 | Horowitz |
| 4,762,129 A | 8/1988 | Bonzel |
| 4,815,449 A | 3/1989 | Horowitz |

(List continued on next page.)

FOREIGN PATENT DOCUMENTS

| | | |
|---|---|---|
| DE | 392700 A1 | 2/1991 |
| DE | 392 7001 | 8/1993 |
| EP | 0 433 011 B1 | 7/1994 |
| EP | 0 688 580 A1 | 12/1995 |
| EP | 0593 136 B1 | 3/1997 |

(List continued on next page.)

OTHER PUBLICATIONS

Radiation Quantities and Units, ICRU Report 33, International Commission on Radiation, Units and Measurements, Apr. 15, 1980.

(List continued on next page.)

Primary Examiner—Eric F. Winakur
Assistant Examiner—Nikita Veniaminov
(74) Attorney, Agent, or Firm—Knobbe Martens Olson and Bear, LLP

(57) ABSTRACT

Disclosed are sources and methods for delivering a radioactive dose to a site in a body lumen. The sources are preferably mounted on a balloon or other expandable or deployable mechanical structure. The source and methods enable delivery of a clinically significant dose of radiation into a vessel wall in a relatively short time while using a relatively low activity. The sources also enable delivery of a substantially uniform dose into the vessel wall, whether or not such delivery is through the wall of a stent.

47 Claims, 24 Drawing Sheets

U.S. PATENT DOCUMENTS

| | | | |
|---|---|---|---|
| 4,819,618 A | 4/1989 | Liprie | |
| 4,878,492 A | 11/1989 | Sinofsky et al. | |
| 4,946,435 A | 8/1990 | Suthanthiran et al. | |
| 4,994,013 A | 2/1991 | Suthanthiran et al. | |
| 5,011,677 A | 4/1991 | Day et al. | |
| 5,019,369 A | 5/1991 | Presant et al. | |
| 5,040,548 A | 8/1991 | Yock | |
| 5,059,166 A | 10/1991 | Fischell et al. | |
| 5,061,273 A | 10/1991 | Yock | |
| 5,100,429 A | * 3/1992 | Sinofsky et al. | 623/1.21 |
| 5,106,360 A | 4/1992 | Ishiwara et al. | |
| 5,152,747 A | 10/1992 | Oliver | |
| 5,163,896 A | 11/1992 | Suthanthiran et al. | |
| 5,176,617 A | 1/1993 | Fischell et al. | |
| 5,199,939 A | 4/1993 | Dake et al. | |
| 5,213,561 A | 5/1993 | Weinstein et al. | |
| 5,267,960 A | 12/1993 | Hayman et al. | |
| 5,302,168 A | 4/1994 | Hess | |
| 5,302,369 A | 4/1994 | Day et al. | |
| 5,342,283 A | 8/1994 | Good | |
| 5,354,257 A | 10/1994 | Roubin et al. | |
| 5,411,466 A | 5/1995 | Hess | |
| 5,424,288 A | 6/1995 | Order | |
| 5,484,384 A | 1/1996 | Fearnot | |
| 5,498,227 A | 3/1996 | Mawad | |
| 5,503,613 A | 4/1996 | Weinberger | |
| 5,540,659 A | 7/1996 | Tierstein | |
| 5,605,530 A | 2/1997 | Fischell et al. | |
| 5,609,629 A | * 3/1997 | Fearnot et al. | 623/1.42 |
| 5,616,114 A | 4/1997 | Thornton et al. | |
| 5,618,266 A | 4/1997 | Liprie | |
| 5,643,171 A | 7/1997 | Bradshaw et al. | |
| 5,653,683 A | 8/1997 | D'Andrea | |
| 5,662,580 A | 9/1997 | Bradshaw et al. | |
| 5,674,177 A | 10/1997 | Hehrlein et al. | |
| 5,683,345 A | 11/1997 | Waksman et al. | |
| 5,688,220 A | 11/1997 | Verin et al. | |
| 5,707,332 A | 1/1998 | Weinberger | |
| 5,713,828 A | 2/1998 | Coniglione | |
| 5,720,717 A | 2/1998 | D'Andrea | |
| 5,722,984 A | 3/1998 | Fischell et al. | |
| 5,728,042 A | 3/1998 | Schwager | |
| 5,730,698 A | 3/1998 | Fischell et al. | |
| 5,755,690 A | 5/1998 | Saab | |
| 5,762,631 A | 6/1998 | Klein | |
| 5,762,903 A | 6/1998 | Park et al. | |
| 5,766,204 A | * 6/1998 | Porter et al. | 606/198 |
| 5,782,740 A | 7/1998 | Schneideman | |
| 5,782,741 A | 7/1998 | Bradshaw et al. | |
| 5,782,742 A | 7/1998 | Crocker et al. | |
| 5,795,286 A | 8/1998 | Fischell et al. | |
| 5,840,008 A | 11/1998 | Klein et al. | |
| 5,840,009 A | 11/1998 | Fischell et al. | |
| 5,860,991 A | 1/1999 | Klein et al. | |
| 5,863,284 A | 1/1999 | Klein | |
| 5,871,436 A | 2/1999 | Eury | |
| 5,879,282 A | 3/1999 | Fischell et al. | |
| 5,911,717 A | 6/1999 | Jacobson et al. | |
| 5,919,126 A | 7/1999 | Armini | |
| 5,924,973 A | * 7/1999 | Weinberger | 600/3 |
| 5,980,566 A | 11/1999 | Alt | |
| 6,013,019 A | 1/2000 | Fischell et al. | |
| 6,019,718 A | 2/2000 | Hektner | |
| 6,024,690 A | 2/2000 | Lee et al. | |
| 6,033,357 A | 3/2000 | Ciezki et al. | |
| 6,042,600 A | 3/2000 | Rosenthal et al. | |
| 6,045,495 A | 4/2000 | Weinberger | |
| 6,048,299 A | 4/2000 | Hoffmann | |
| 6,050,930 A | 4/2000 | Teirstein | |
| 6,059,713 A | 5/2000 | Urick et al. | |
| 6,059,714 A | 5/2000 | Armini et al. | |
| 6,059,752 A | 5/2000 | Segal | |
| 6,071,227 A | 6/2000 | Popowski | |
| 6,077,413 A | 6/2000 | Hafeli | |
| 6,099,499 A | * 8/2000 | Ciamacco, Jr. | 604/103 |
| 6,103,295 A | 8/2000 | Chan et al. | |
| 6,149,574 A | 11/2000 | Trauthen et al. | |
| 6,176,821 B1 | 1/2001 | Crocker et al. | |

FOREIGN PATENT DOCUMENTS

| | | |
|---|---|---|
| WO | WO 93/04735 | 3/1993 |
| WO | WO 94/23789 | 10/1994 |
| WO | WO 94/26205 | 11/1994 |
| WO | WO 95/19807 | 7/1995 |
| WO | WO 95/29008 | 11/1995 |
| WO | WO 96/10436 | 4/1996 |
| WO | WO 96/13303 | 5/1996 |
| WO | WO 96/14898 | 5/1996 |
| WO | WO 96/22121 | 7/1996 |
| WO | WO 97/18012 | 5/1997 |
| WO | WO 98/33555 | 8/1998 |
| WO | WO 99/24116 | 5/1999 |
| WO | WO 99/32192 | 7/1999 |
| WO | WO 99/42163 | 8/1999 |
| WO | WO 99/42177 | 8/1999 |
| WO | WO 00/29501 | 5/2000 |
| WO | WO 01/14011 | 3/2001 |

OTHER PUBLICATIONS

Effects of high–dose intracoronary iradiation on vasomotor function and smooth muscle histopathology, Joseph G. Wiedermann, et al., Interventional Cardiology Center, Department of Medicine and Radiation Oncology and Section of Cardiac Pathology, Columbia–Presbyterian Medical Center and Columbia University, 1994 the American Physiological Society.

Intracoronary Irradiation Markedly Reduces Restenosis After Balloon Angioplasty in a Porcine Model, Joseph G. Wiedemann, M.D., et al., JACC vol. 23 No. 6, May 1994; 1491–8.

Intracoronary Irradiation Markedly Reduces Neointimal Proliferation After Balloon Angioplasty in a Swine; Persistent Benefit at 6–Month Follow–up; Joseph G. Wiedemann, M.D., et al., JACC vol. 25 No. 6, May 1995; 1451–6.

Discoveries in Radiation for Restenosis, Emory University of School of Medicine, Presented by The Andreas Gruentzig Cardiovascular Center and the Department of Radiation Oncology of Emory University School of Medicine; J.W. Marriott Hotel at Lenox, Atlanta, GA; Jan. 11–12, 1996.

* cited by examiner

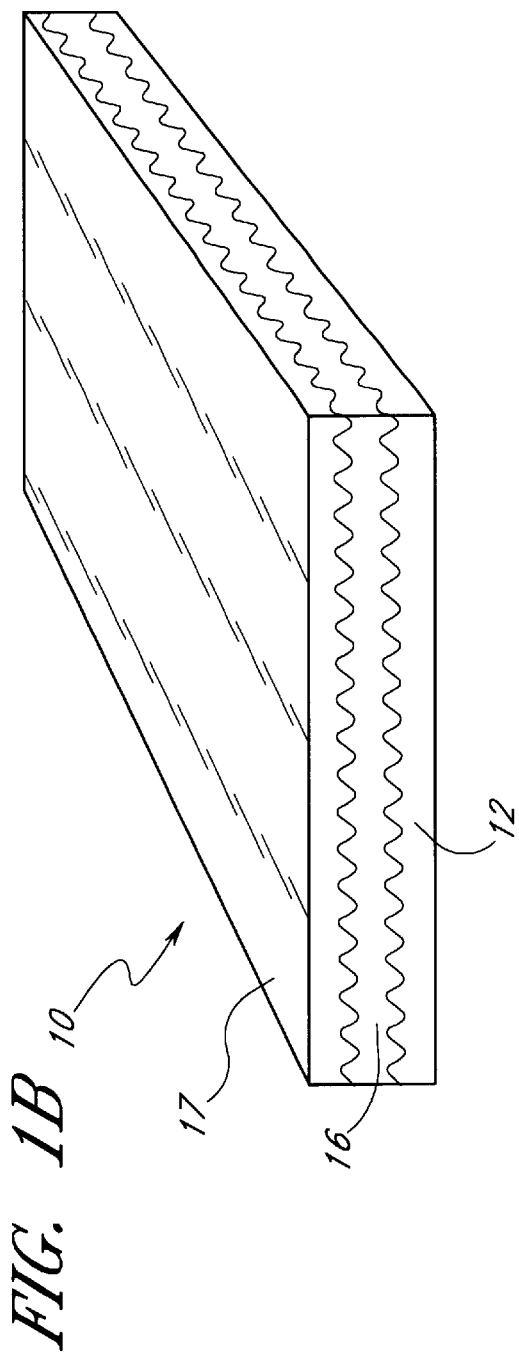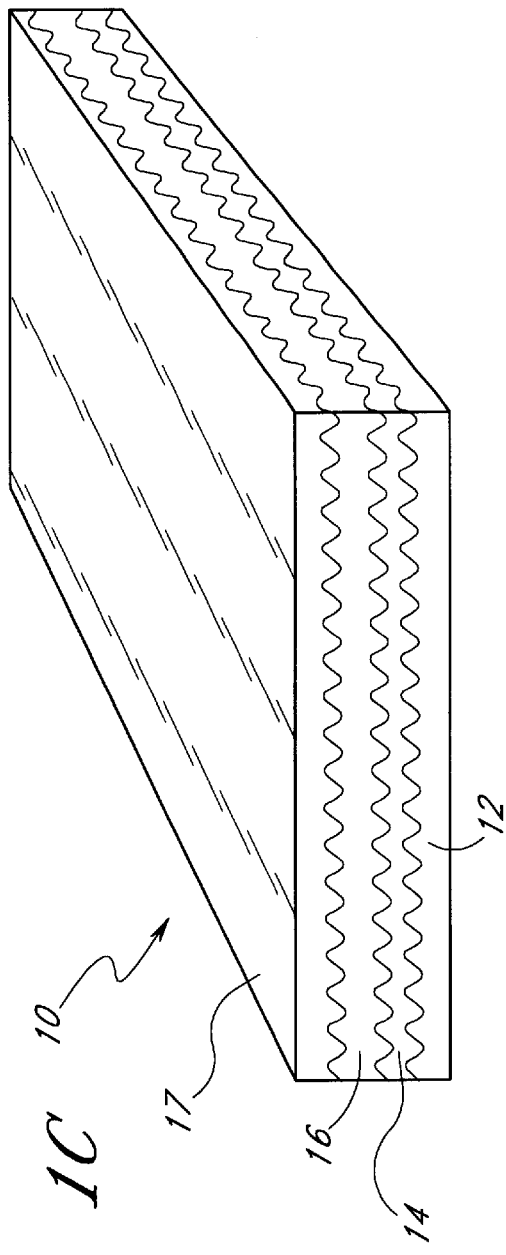

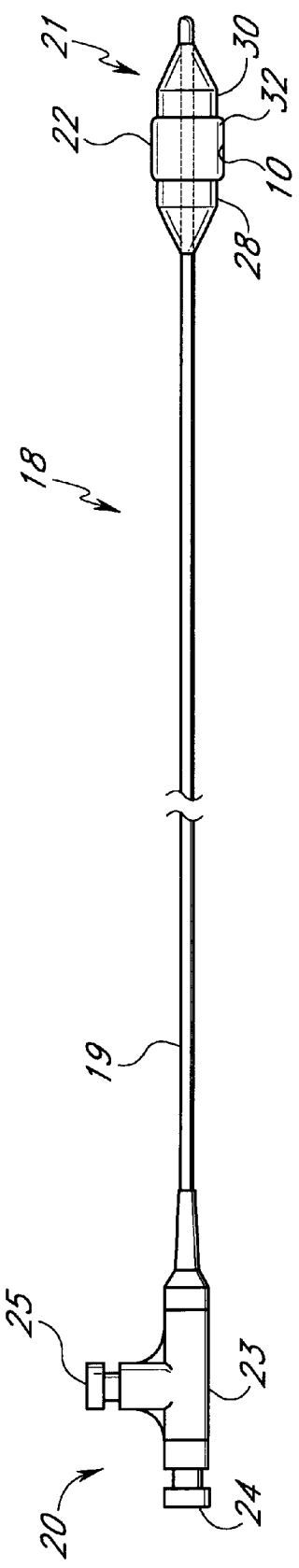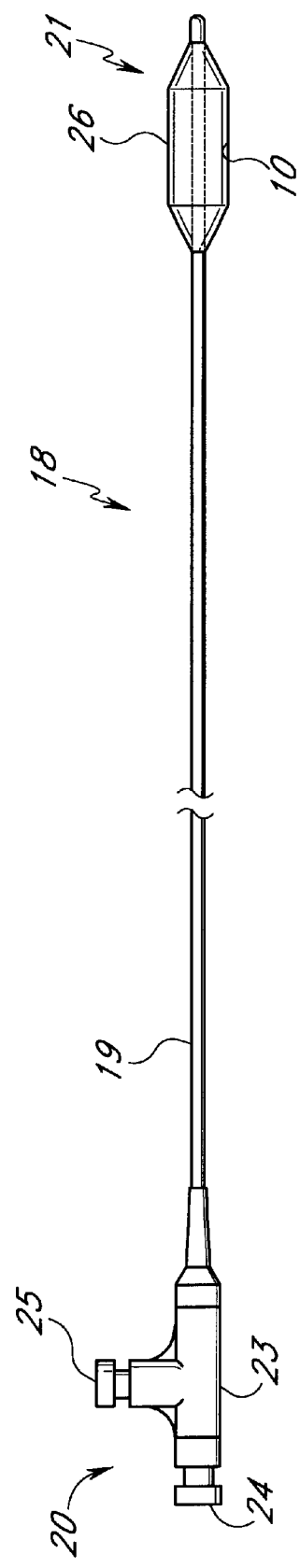

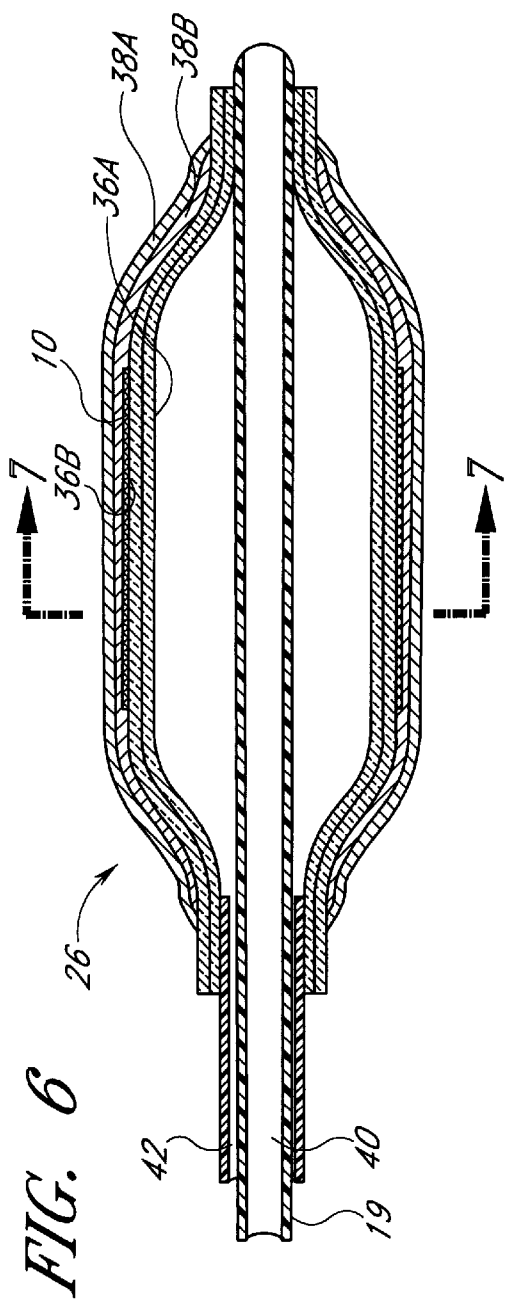
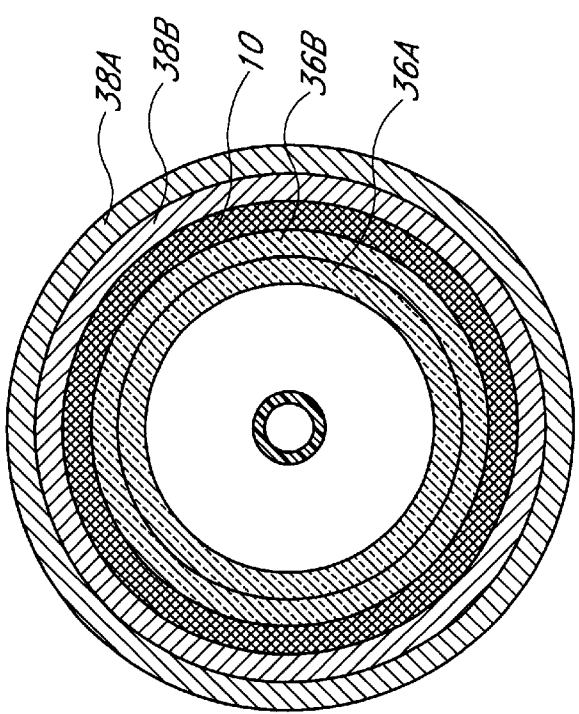

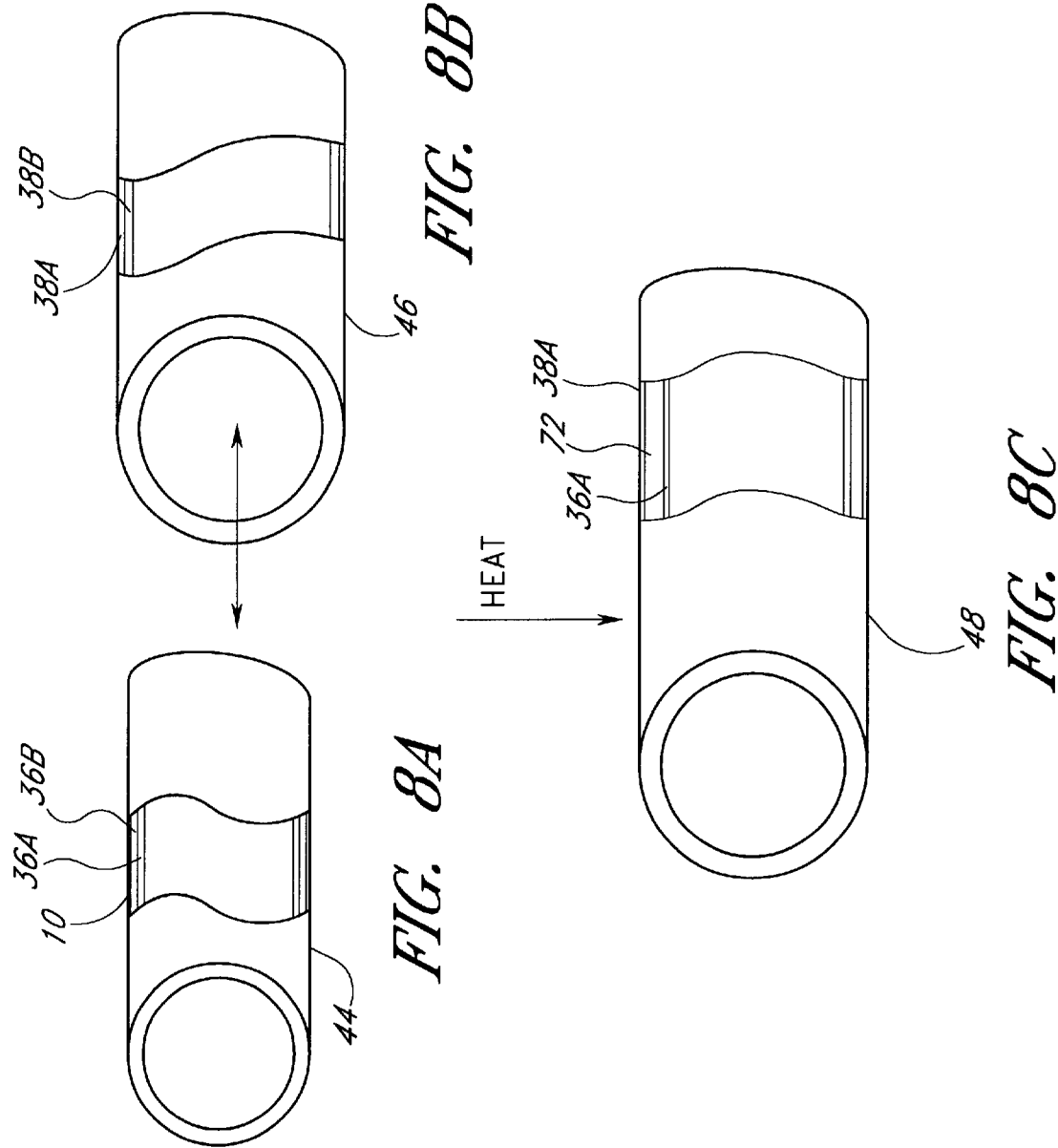

$$V_{\text{AFFECTED TISSUE}} = \tfrac{4}{3}\pi R^3$$

$$V_{\text{AFFECTED TISSUE}} = \ell\pi(R + D)^2 - \ell\pi R^2$$

RADIATION DELIVERY CATHETERS AND DOSIMETRY METHODS

RELATED APPLICATION DATA

This application is a continuation in part of Ser. No. 09/382,302, filed Aug. 24, 1999, which is a continuation-in-part of Ser. No. 09/256,337, filed Feb. 19, 1999, now U.S. Pat. No. 6,287,249, which is a continuation-in-part of Ser. No. 09/025,921, filed Feb. 19, 1998, abandoned. This application is also a continuation in part of Ser. No. 09/119,828, filed Apr. 5, 2000, now U.S. Patent No. 6,176,821, which is a continuation of Ser. No. 08/789,969, filed Jan. 31, 1997, now U.S. Pat. No. 5,782,742.

FIELD OF THE INVENTION

This invention relates to structures attachable to catheters to deliver radiation to a treatment site in the body. In one application, the catheter is used to prevent or slow restenosis of an artery traumatized such as by percutaneous transluminal angioplasty (PTA).

BACKGROUND OF THE INVENTION

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States in 1990 and nearly one million procedures worldwide in 1997. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 40% or more of all patients requiring repeat PTCA procedures or by-pass surgery, with attendant high cost and added patient risk.

Various attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to prevent the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of vascular cells in the region traumatized by the angioplasty which is termed neointimal hyperplasia. Neointimal hyperplasia narrows the lumen that was opened by the angioplasty, regardless of the presence of a stent, thereby necessitating a repeat PTCA or other procedure to alleviate the restenosis.

Preliminary studies indicate that intravascular radiotherapy (IVRT) has promise in the prevention or long-term control of restenosis following angioplasty. IVRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation, hemorrhaging, and other risks discussed below. Underdosing will result in inadequate inhibition of smooth muscle cell hyperplasia, or even exacerbation of hyperplasia and resulting restenosis.

The prior art contains many examples of catheter based radiation delivery systems. The simplest systems disclose seed train type sources inside closed end tubes. An example of this type of system can be found in U.S. Pat. No. 5,199,939 to Dake. In order to separate the radiation source from the catheter and allow re-use of the source, a delivery system is disclosed by U.S. Pat. No. 5,683,345 to Waksman et al. where radioactive source seeds are hydraulically driven into the lumen of a closed end catheter where they remain for the duration of the treatment, after which they are pumped back into the container. Later disclosures integrated the source wire into catheters more like the type common in interventional cardiology. In this type of device, a closed end lumen, through which is deployed a radioactive source wire, is added to a conventional catheter construction. A balloon is incorporated to help center the source wire in the lumen. It is supposed that the radioactive source wire would be delivered through the catheter with a commercial type afterloader system produced by a manufacturer such as Nucletron, BV. These types of systems are disclosed in Liprie U.S. Pat. No. 5,618,266, Weinberger U.S. Pat. No. 5,503,613, and Bradshaw U.S. Pat. No. 5,662,580.

In the systems disclosed by Dake and Waksman, the source resides in or very near the center of the catheter during treatment. However, it does not necessarily reside in the center of the artery. The systems disclosed by Weinberger and Bradshaw further include a centering mechanism, such as an inflatable balloon, to overcome this shortcoming. In either case, the source activity and energy must be high enough to overcome absorption loss encountered as the radiation traverses the lumen of the blood vessel to get to the target tissue site in the vessel wall.

Higher activity and energy sources, however, can have undesirable consequences. First, the likelihood of radiation inadvertently affecting untargeted tissue is higher because the absorption factor per unit tissue length is lower. Second, the higher activity and energy sources are more hazardous to the medical staff and thus require additional shielding during storage and additional precaution during use. In addition, the source of any activity or energy may or may not be exactly in the center of the lumen, so the dose calculations are subject to error factors due to non-uniformity in the radial distance from the source surface to the target tissue. The impact of these factors is a common topic of discussion at recent medical conferences addressing Intravascular Radiation Therapy, such as the Trans Catheter Therapeutics conference, the Scripps Symposium on Radiotherapy, the Advances in Cardiovascular Radiation Therapy meeting, the American College of Cardiology meeting, and the American Heart Association Meeting.

The impact on treatment strategy is discussed in detail in a paper discussing a removable seed system similar to the ones disclosed above (Tierstein et al., Catheter based Radiotherapy to Inhibit Restenosis after Coronary Stenting, NEJM 1997; 336(24):1697–1703). Tierstein reports that Scripps Clinic physicians inspect each vessel using ultrasonography to assess the maximum and minimum distances from the source center to the target tissue. To prevent a dose hazard, they will not treat vessels where more than about a 4×differential dose factor (8–30 Gy) exists between the near vessel target and the far vessel target. Differential dose factors such as these are inevitable for a catheter in a curvilinear vessel such as an artery, and will invariably limit the use of radiation from conventional wire and seed train sources and add complexity to the procedure. Moreover, the paper describes the need to keep the source in a lead transport device called a "pig", as well as the fact that the medical staff leaves the catheterization procedure room during the treatment. Thus added complexity, time and risk is added to the procedure caused by variability of the position of the source within the delivery system and by the activity and energy of the source itself.

A variety of additional structures have been disclosed, as alternatives to the wire and seed train systems. For example, U.S. Pat. No. 5,302,168 to Hess teaches the use of a radioactive source contained in a flexible carrier with remotely manipulated windows; Fearnot discloses a wire basket construction in U.S. Pat. No. 5,484,384 that can be introduced in a low profile state and then deployed once in place; Hess also purports to disclose a balloon with radioactive sources somehow attached on the surface in U.S. Pat. No. 5,302,168; Hehrlein discloses a balloon catheter which carries an active isotope on the balloon in WO 96/22121; and Bradshaw discloses a balloon catheter adapted for use with a liquid isotope in U.S. Pat. No. 5,662,580.

In a non-catheter based approach, U.S. Pat. No. 5,059,166 to Fischell discloses an IVRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. In addition, current stents are generally not removable without invasive procedures. The dose delivered to the blood vessel is also non-uniform because the tissue that is in contact with the individual struts of the stent receive a higher dosage than the tissue between the individual struts.

Another approach is to use a nuclide suspended in solution to inflate a balloon (Thornton '114). This technique provides uniform nuclide distribution within the balloon to form the source, resulting in uniform dose patterns. Also, this configuration moves the position of the nuclide closer to the target tissue. A relatively conventional appearing catheter may be used for this type of approach, and many nuclides are available in liquid form. Hence, several investigators have begun clinical studies on so-called radioactive liquid filled balloons.

While in some ways appearing to provide a solution to the problem of centering, the liquid filled balloon systems have other drawbacks. For example, as is known to those familiar with the design, manufacture, or use of balloon angioplasty catheters, balloons potentially break. If a balloon is used to contain an active nuclide, a break poses an obvious health threat to the patient, physician and any nearby laboratory personnel. A break or leak may also shut down the procedure room. In addition, the activity to achieve a desired delivered dose is still relatively high. The distribution of isotope throughout the radius of the balloon acts like a source spaced apart from the vessel wall with a resulting decay in activity before reaching the target tissue.

In all of the foregoing designs, full containment of the isotope remains a significant challenge. The American National Standards Institute (ANSI) publishes a standard for sealed sources (ANSI N44.1-1973 Integrity and Test Specifications for Selected Brachytherapy Sources), and the US Nuclear Regulatory Commission (NRC) defines a sealed source as containing less than 5 nanoCuries ($5\times10^{-9}$ Curies) of removable activity. Hehrlein reported (Scripps Conference, January 1998) a balloon coated with P-32 that lost 0.5% of its contained activity in an animal study. Even with only 1 mCi of contained activity, the balloon proposed by Hehrlein would have lost 5000 nCi, well beyond NRC standards for a sealed source, and well outside of the ANSI definition of a sealed source.

Despite the foregoing, among many other advances in IVRT, there remains a need for an IVRT method and apparatus that delivers an easily controllable uniform dosage of radiation without the need for special devices or methods to center a radiation source in the lumen. Furthermore, a need remains for a radiation delivery device which is similar in use to conventional angioplasty balloon catheters, and which has a sealed source to prevent escape of radioactive species.

SUMMARY OF THE INVENTION

There is provided in accordance with one aspect of the present invention, a method of optimizing an in stent radiation delivery profile, comprising the steps of identifying a stent positioned against the wall of a vessel; positioning a radiation source within the stent; and exposing the vessel to radiation through the stent such that variations in the dose delivered to a depth of about 1 mm in the wall of the vessel along the length of the source do not exceed about 50%, and preferably do not exceed about 20%.

In accordance with another aspect of the invention, there is provided a radiation delivery catheter for in stent delivery of a substantially uniform dose of radiation, comprising an elongate, flexible, tubular body, having a proximal end and a distal end; and a radiation source near the distal end, wherein the source is capable of a substantially uniform delivery of radiation at a depth of about 1 mm in tissue behind the stent along a length of at least about 30% of the length of the source.

In accordance with another aspect of the present invention, there is provided a method of treating tissue, comprising delivering radiation at a dose of at least about 8 Gy, at a depth of 1 mm into the tissue, over a time of less than about 20 minutes, and preferably less than about 15 minutes. In different applications of the invention, the tissue is in the coronary arteries, carotid arteries, intra-cranial vasculature, peripheral vasculature, vascular anastomoses anywhere in the body and in one application on saphenous vein grafts, the esophagus, trachea, airways of the lung, stomach, intestines, rectum, uterus, fallopian tubes, or other hollow organs, lumens or surgically created pathways in the body.

In accordance with another aspect of the present invention, there is provided a radiation delivery catheter, for delivering a dose of radiation within a vessel, comprising an elongate flexible body, having a proximal end and a distal end; and a radiation source carried by the body near the distal end thereof; wherein the source is configured to deliver a dose in excess of about 8 Gy at a depth of 1 mm into the vessel wall over a time period of no more than about 15 minutes.

In accordance with another aspect of the present invention, there is provided a method of optimizing radiation dose uniformity in a vessel wall behind a stent, comprising the steps of positioning a radiation delivery catheter within a stent in a body vessel, delivering a first dose of beta radiation along a first axis past a first side of a stent strut and into the vessel wall; and delivering a second dose of beta radiation along a second axis past a second side of the strut and into the vessel wall; wherein the first axis and the second axis converge behind the strut to deliver a desired dose behind the strut.

In accordance with a further aspect of the present invention, there is provided a method of optimizing an intraluminal radiation delivery profile, comprising the steps of identifying a treatment site in the wall of a vessel; positioning a radiation source against the wall; and exposing the vessel to radiation such that variations in the dose delivered to a depth of about 1 mm in the wall of the vessel along the length of the source do not exceed about 50%, and preferably do not exceed about 20%.

In accordance with yet another aspect of the present invention, there is provided a radiation delivery catheter for delivering a substantially uniform dose of radiation, comprising an elongate, flexible, tubular body, having a proximal end and a distal end; and a radiation source near the distal end; wherein the source is capable of a substantially uniform delivery of radiation at a depth of about 1 mm into the wall of the vessel along a length of at least about 30% of the length of the source.

In accordance with yet another aspect of the present invention, there is provided a method of optimizing a radiation delivery profile in a peripheral vessel, with or without a stent at the treatment site, comprising the steps of identifying a treatment site in a vessel, positioning a radiation source at the site; and exposing the vessel to radiation such that variations in the dose delivered to a depth of about 2 mm in the wall of the vessel along the length of the source do not exceed about 20%.

In accordance with another aspect of the present invention, there are provided methods for making radiation delivery catheters having non-uniform, non-homogeneous, or discontinuous sources. Such sources include, but are not limited to, those having higher or lower activity on different areas of the source, sources in which some areas of the source contain one or more additional layers, sources having slits, notches or grooves, sources comprising a plurality of source strips which are spaced apart by a minor amount, sources having greater activity near the ends of their length (extended effective radiaiton length), and sources having reduced activity at their ends. The methods for making such sources include use of techniques such as masking, etching, variable reaction times, inhomogeneous deposition of source layers, ion implantation, plastics extrusion and molding, electrodeposition, adsorption, and metal sheet stamping.

In accordance with another aspect of the present invention there is provided a method for treating lesions having a length greater than that of the source used for treatment. In this method, a radiation delivery catheter is provided in which the source has bands of reduced activity at the proximal and distal ends of the source. After insertion, the source on the catheter is placed at two or more generally adjacent positions in the area of the lesion, in series, allowing for some overlap of the regions with reduced activity.

Further features and advantages of the present invention will become apparent to those of skill in the art in view of the detailed description of preferred embodiments which follow, when considered together with the attached drawings and claims.

BRIEF DESCRIPTION OF THE DRAWINGS

FIG. 1B is a schematic of a cross-section of one embodiment of the radiation delivery source of the present invention having a substrate layer, an isotope layer and a coating layer.

FIG. 1C is a schematic of a cross-section of one embodiment of the radiation delivery source of the present invention having a substrate layer, a tie layer, an isotope layer and a coating layer.

FIG. 2 is a schematic side elevational view of a catheter incorporating the thin film source of the present invention.

FIG. 3 is a schematic side elevational view of an alternate catheter incorporating the thin film source of the present invention.

FIG. 6 is an enlarged side elevational cross-sectional detail view through a balloon incorporating a multi-layered sealed source embodiment of the present invention.

FIG. 7 is a cross-section taken along the line 7—7 in FIG. 6.

FIG. 8 is a schematic illustration of the assembly of one embodiment of a multi-layered sealed source in which portions are shown in partial cross-section.

Figure 1:
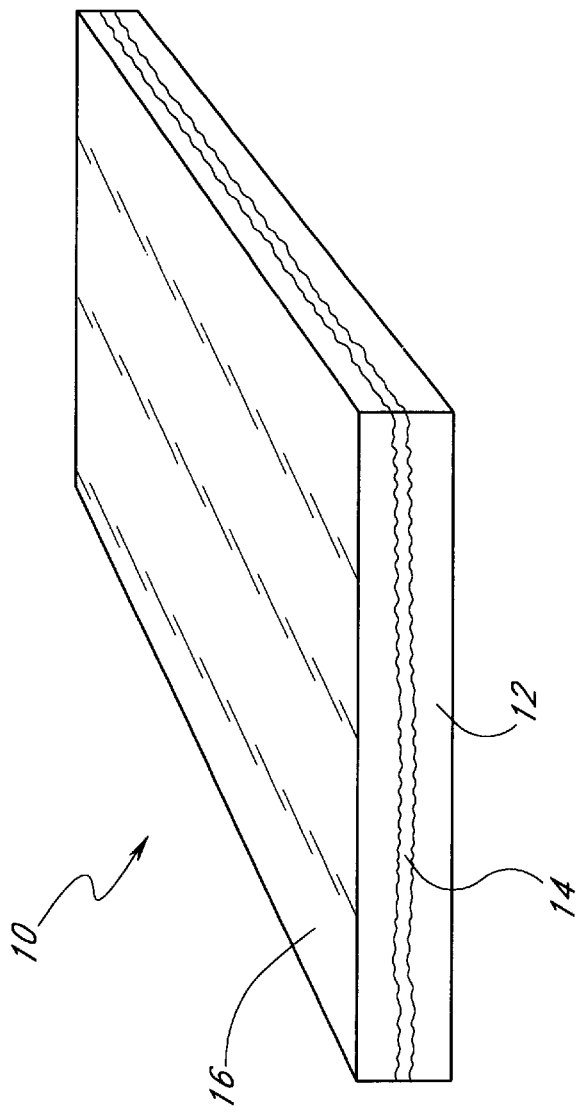
FIG. 1 is a schematic perspective view of a thin film radiation source in accordance with the present invention.

The drawing figures are not necessarily to scale.

DETAILED DESCRIPTION OF THE PREFERRED EMBODIMENT

This invention provides dosimetry methods and catheters which incorporate a radioactive source intended for site specific delivery of radiation ("brachytherapy") to an anatomical structure. As presently contemplated, in one embodiment the source is incorporated into an expandable or enlargeable region at the distal end of a catheter.

In one aspect, this invention provides a novel multilayered sealed source design, new in terms of structure, materials and production methods which can be generally described as a thin film radioactive source. This source can be incorporated in a catheter or the source could be incorporated into traditional "seeds," or placed on a wire, or on a trocar, or most any other delivery system. The thin film can be rolled up into a cylindrical configuration for insertion and unrolled in-situ for positioning adjacent the vessel wall either by itself or as a laminate on a flexible metal or polymeric support sheet, such as disclosed in U.S. Pat. No. 6,048,299 the disclosure of which is incorporated in its entirety herein by reference. Although other types of sources, including foils, and these other structures for carrying the sources are contemplated, for the sake of simplicity, the sources will be described herein primarily in the context of a sealed multilayer source balloon structure for use in intravascular procedures.

Multilayer Thin Film Sources

The term "thin film source" is descriptive of the invention's structure. Referring to FIG. 1, the source 10 comprises of a thin sheet, or "substrate" layer 12, a chemical attachment or "tie" layer 14 for binding the isotope, and an isotope species 16. The substrate 12 can consist of a very thin (1 microns, or from about 0.00004 to about 0.002" thickness) sheet or tubing. At these thicknesses, a wide variety of biologically compatible materials are very flexible and conforming. Examples of substrates commercially available at these thicknesses are Mylar® (polyester), Kapton® (polyirnide), polyethylene, nylon, and polyurethane, EMA, and polyethylene terephthalate (PET), in the form of sheet or tubing, or even metal foils.

Figure 1A:
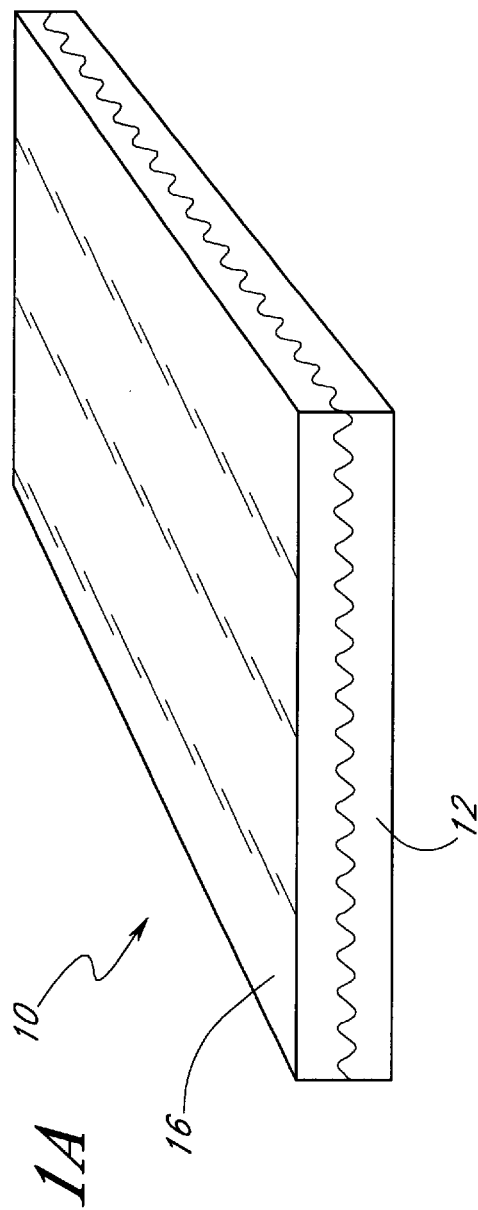
FIG. 1A is a schematic perspective view of an alternate thin film source in accordance with the present invention.

FIGS. 1A–1C show additional embodiments of the thin film source of the present invention. Referring to FIG. 1A, a schematic of a cross-section of a two-layer embodiment of thin film source is shown. The first or innermost layer is the substrate 12, and the second or outer layer is the isotope layer 16.

Referring to FIG. 1B, a schematic of a cross-section of thin film source, wherein the source has three layers, is shown. The first or innermost layer is the substrate 12, the second or middle layer is the isotope layer 16, and the outer layer is the coating layer 17.

Referring to FIG. 1C, a schematic of a cross-section of a four-layer embodiment of the thin film source of the present invention is shown. The four layers are the substrate layer 12, tie layer 14, isotope layer 16, and coating layer 17.

The thin film sources of the present invention are comprised of two or more layers of materials. There may or may not be a clear visual or physical distinction between the various layers in the source 10 because each layer need not be a discrete structural element of the thin film source 10. As the layers bond together to form the source, they may become blended, alloyed, intermingled or the like to form what looks and acts like a single layer having a somewhat heterogeneous composition. For this reason, the various layers as defined and used herein are intended to denote the functional characteristics of the components or help denote what process steps are used in their formation, whether through the use of discrete structural layers or layers blended with neighboring layers, the selection of which will be apparent to those of skill in the art in view of the particular materials and components used.

For example, the term tie layer as used herein is intended to denote a functional characteristic which enables securing of the isotope species 16 to the substrate 12, whether through the use of a discrete structural layer (such as an adhesive, reactive metal, metal salt, or functionally analogous component) or a surface modification to the substrate 12 (such as chemical activation or chemical reaction so as to form a salt). For example, FIG. 1A schematically represents a substrate 12 having an isotope zone 16 comprising at least one isotope.

The thin film sources of the present invention all comprise a substrate layer or substrate 12. The thickness and composition of the substrate layer 12 can be varied widely, depending upon the catheter design or the design of the other medical device to which the isotope species 16 is to be bound. For example, materials in the thickness of conventional PTCA balloons (from about 0.0005 to about 0.005 inches) may be utilized, such as where the balloon itself is used as the substrate 12. Additionally, a layer of bonding material or encapsulant may be used as the substrate 12.

A balloon substrate may be either of the compliant or non-compliant variety, as known in the art. Thus, for a radiation delivery balloon which is not intended to additionally accomplish angioplasty, working pressures on the order of 1 to 6 atmospheres may be used. At such relatively low pressures, a variety of balloon materials may be utilized, which do not experience excessive expansion as a function of pressure. If higher inflation pressures are desired, more traditionally non-compliant materials such as polyethylene terephthalate may be desirable. In general, the radioactive source on the delivery balloon preferably exhibits minimal or no expansion in response to pressure. The substrate 12 may be polymeric or a metal, depending upon the desired characteristics of the finished product.

The thin film sources also all comprise an isotope layer 16. The isotope layer comprises at least one radioactive isotope. Such isotopes are preferably either beta- or gamma-emitting, although x-ray emitters or Bremsstrahlung radiation from a beta source may also be used. In one embodiment, the isotope layer comprises a collection of individual isotope ions, atoms, or compounds attached to the layer below, preferably in a relatively even distribution. In another embodiment, the isotope layer comprises a metal salt (tie layer) wherein some or all of one ion of the salt has been replaced by isotope ions (simple or complex). Such an isotope layer may be bound directly to the substrate layer 12 or to another tie layer 14, if present. In a preferred embodiment, the isotope layer has an isotope density or nuclide density in the range of $10^5$–$10^{22}$ atoms/cm$^2$, preferably about $10^{10}$–$10^{20}$ atoms/cm$^2$ more preferably for coronary applications about $10^{15}$ to $10^{17}$ atoms/cm$^2$. The thickness is preferably from about 25 to about 10,000 Angstroms thick, and more preferably from about 25 to about 100 Angstroms thick.

As used herein, the term "metal salt" refers to a compound comprised of at least one anion and at least one cation. The anions and cations of the metal salt may be either simple (monatomic) ions such as $Al^{3+}$, $Cl^-$, $Ca^{2+}$, $Zn^{2+}$, $I^-$, and $Na^+$, and $Ag^+$, or complex (polyatomic) ions such as $PO_4^{3-}$, $O_3^{2-}$, and $WO_4^{2-}$. At least one of the ions in the metal salt should comprise a metal. The term "metal" as used herein means all metals, including, for example, transition metals, alkali metals, and alkaline earth metals, as well as semi-metals. Preferably metals are selected from the transition metals or main group of the Periodic Table of the Elements. The term "metal salt" as used herein in its broadest sense encompasses metal oxides. A metal salt layer, when present, is preferably 100 to 10,000 Angstroms thick, more preferably 200 to 1000 Angstroms thick.

The thin film sources of the present invention may further comprise at least one tie layer 14. The tie layer 14 lies between the substrate 12 and isotope layer 16 and may act to increase the tenacity of attachment of the isotope layer 16 to the substrate 12. The tie layer 14 may be any composition or structure which functions to bind the isotope 16 to the substrate 12. The tie layer 14 may comprise adhesives, chemically activated surfaces, mechanical locking structures, a chemical coating layer, or a layer of one or more an organic or inorganic compound. Preferred tie layer materials include metals, alloys, metal salts, alumina and other metal oxides, polyester, polyimide and other polymers. Its chemical composition and structure can be varied, depending on the isotope to be attached. It can be an organic or inorganic material or compound; it must only have the appropriate chemistry to attract and bind the isotope or isotope layer materials or other tie layers. The tie layer may be applied to one or both surfaces of the substrate, depending on factors such as the desired activity, composition or geometry of the finished product. In one embodiment, the tie layer 14 is a layer of metal or metal oxide, and it is within the range of from about 100 to about 10,000 Angstroms thick, more preferably from about 200 to about 1000 Angstroms thick. The multiple layers and/or materials that make up the tie layer 14 may be alloyed, complexed or otherwise physically or chemically bound or attached to each other.

The thin film sources of the present invention may further comprise one or more coating layers 17, as is discussed in connection with FIGS. 6–7 below. A coating layer 17 can act as a sealing means to protect the isotope layer from mechanical abrasion or other injury which could remove radioisotopes from the isotope layer. The coating layer preferably also minimizes or prevents isotope loss in vivo, thus allowing the device to be classified as a sealed radiation source, i.e. one that has less than 5 nCi of removable activity. The coating layer may also provide the additional advantage of sealing or binding the layers of the source to the balloon or encapsulant.

The coating may be a metal or plastic. Plastic coating materials are preferably biocompatible, but not excessively biodegradable. Preferred materials include cyanoacrylates, acrylics, ethylene methyl acrylate, ethylene methyl acrylate/ acrylic acid (EMA/AA), urethanes, thermal plastic urethane (TPU) polybutyl vinyl chloride (PBDC), polycarbonate, polystyrene, polyvinylidene chloride (PVDC, such as Saran®) polyethylene, polyethylene terephthalate, nylon and the like. Likewise, metal coatings can be used as well. If the coating is metal, the metal used is preferably one which is bio-stable. For example, alumina, platinum, gold, or titanium may be vapor deposited on the surface to encapsulate the isotope layer.

The foregoing thin film structures offer several advantages over existing source designs. First, the source can conform to almost any shape, unlike conventional seed or solid wire type sources or even a thin metal film. Thus, this type of source is ideal for incorporation into flexible catheter-based delivery systems.

Isotopes and Isotope Attachment in Thin Film Sources

The radioisotopes used in the thin film sources of the present invention may be beta or gamma emitters, or both, and may have any of a wide range of half-lives, both long and short. The particular isotope, or combination of isotopes as well as the concentration of isotopes in the source (which, along with treatment time, determines the dose), can be chosen by one skilled in the art to serve the needs of a particular application in view of the disclosure herein. In choosing an isotope, possible characteristics of a good candidate isotope may include a low dose gradient, low dose levels to surrounding body tissues, manageable radiation exposure levels around the patient and a sufficient but not excessive half-life. Iodine-125 (I-125, half-life 60 days), tungsten-188/rhenium-188 (W/Re-188, half-life about 70 days) and phosphorous-32 (P-32, half-life 14.3 days) are among the preferred isotopes for use in the present invention.

Preferred radioisotopes are selected from the group of gamma emitters (or x-ray emitters) with energies less than about 300 keV such as I-125, Pd-103, As-73, Gd-153, or the high-energy beta emitters ($E_{max}$>1.5 meV) including P-32 and W/Re-188, or others as may be deemed suitable for a particular use. The selection of the isotope may be influenced by its chemical and radiation properties, and other isotopes not mentioned herein, but which have properties suitable for a particular application, can be utilized in the present invention. Preferred radioisotopes used in the thin film sources of the present invention may be purchased from Oak Ridge National Laboratory (Oak Ridge, Tenn.), New England Nuclear (NEN) or any other commercial suppliers of radioisotopes.

In accordance with one isotope attachment technique, a thin film substrate is treated with a tie layer composed of a three-dimensional matrix with an ionic compound. The choice of the ionic compound is made to encourage the ion desired to bond within the tie layer to make the isotope layer. In one embodiment, the three-dimensional matrix is polyvinyl pyrrolidone (PVP) with an ionic compound containing a $Br^-$ anion. The PVP matrix is commonly used as a carrier for $I_2$ in antimicrobial applications. Direct attachment of the ionic compound would result in layers on the molecular scale. To accomplish attachment, the treated substrate is placed in an ionic solution of I-125 ($Na^{125}I$, a commercially available form of I-125). I-125 anions exchange with $Cl^-$ $Br^-$ anions with less affinity to PVP from the PVP, thus incorporating I-125 into the tie layer and producing a gamma radiation source. A similar system can work alternatively in a solution comprising $^{32}P$-containing ions such as $H_3^{32}PO_4$ (a commercially available form of P-32) to form a beta emitting source.

In one specific embodiment of the source, a generally rectangular polyester sheet having a width of about 2 cm, a length of about 3 cm and a thickness of about 12 microns was coated with a PVP ion exchange surface and soaked in a 0.125 wt % I-125 in NaI solution. The resulting source may thereafter be wrapped around a balloon having an inflated diameter of about 3.0 mm and an axial length of about 30 mm. The sheet length of 3 cm would allow the source to be wrapped around the inflated balloon approximately 3 full revolutions. Thus, in this context, sheet length corresponds to the circumferential direction as wrapped around the balloon, and sheet width corresponds to the axial length of the source along the balloon. In this embodiment, the activity of the source would be approximately 110 milliCuries per centimeter length of the substrate sheet. Thus, by providing three full revolutions, a net activity of about 330 milliCuries may be produced. This activity is similar to that disclosed by Teirstein for the Ir-192 (gamma) source used in the Scripps study. Using the apparatus and methods disclosed herein, the net activity could conveniently be doubled, for example, by lengthening the substrate sheet to about 6 cm, thereby enabling six revolutions of the substrate around the balloon. This may accomplish a respective reduction in treatment time of 50%.

In cases where adequate activity can be achieved with a single wrap of the source (e.g., source sheet length equals expanded source circumference), a thin tube could be used alternatively to the sheet. For example, PET tubing can be commercially obtained with wall thicknesses similar to the sheet material described earlier (0.0003–0.001 inch). The tube construction may allow for simpler assembly, but otherwise it possesses the same properties as the rolled sheet.

In one specific embodiment of the present invention a PE/EMA coextruded, crosslinked and expanded tube was manufactured to a wall thickness of 0.0005" to 0.0015" thick. A metal oxide (metal salt) tie layer, a metal salt layer and an isotope layer was placed on the sheet. The nuclide density of P-32 on the tube was similar to that of a sheet of the same specific surface area. A delivery system may be manufactured in similar fashion to the sheet source with the added benefit of sealing the entire tubular substrate to at least the encapsulant in addition to the proximal and distal balloon to encapsulant seal.

There are alternative ways of taking advantage of the thin film structural properties, however, without utilizing a chemical attachment system for the isotopes. For example, the radioactive isotope or a salt thereof can be attached directly to the sheet without a distinct tie layer 14 such as through ion implantation, vapor deposition, or sputtering. Thus, for some techniques, a distinct tie layer 14 is omitted completely. See FIGS. 1A and 1B.

Other methods of direct isotope attachment to the substrate can be considered for some isotopes. For example, vapor deposition and sputtering can be used to deposit metal isotopes on the substrate in a manner similar to that used to deposit polymers, metals or salts. The layers in these processes can be controlled to submicron thicknesses, such that all of the physical/mechanical advantages described in the above paragraphs for chemical attachment systems are maintained: flexibility, ability to adjust activity based on multiple wraps, ability to utilize less active isotopes.

Preferred methods of making the isotope layer of the preferred embodiments may begin with either a substrate to be coated or a tie layer to serve as the place of attachment. Preferred methods comprise exposing surfaces to fluids comprising reactants or isotopes.

Such fluids may be gaseous (including plasma and vapor) or liquid (such as solutions), with liquid solutions being preferred. As such, the methods below are described in terms of liquid solutions.

Some methods of making the isotope layer of the thin film sources comprise, in part, either one or both of the following solution processes: (1) oxidation in an acidic solution to form a metal salt from a metal; and (2) ion exchange wherein ions at or near the surface of the metal salt are exchanged with those present in a solution. The first process is based on differences in oxidation-reduction potentials, and the second process is based on differences in solubility. These processes will be taken in turn.

In the first process, the equilibrium is driven by principles of oxidation-reduction (redox). A metal, in the form of a pure metal or part of an alloy, may be converted to a metal salt when it is placed in solution comprising an oxidizing agent. Many metals, including those in preferred embodiments discussed below, can be readily oxidized in solution to form metal cations, which may then form salts with anions in solution.

Whether or not a particular reaction of an oxidizing agent and a metal will occur spontaneously can be predicted by reference to a standard table of half-cell potentials such as that in *CRC Handbook of Chemistry and Physics*, (CRC Press). If the sum of the potentials of the oxidation half-reaction and the reduction half-reaction is positive, then the reaction will occur spontaneously.

For example, it can be predicted that when silver is added to an acid solution of sodium chlorite, the silver will be oxidized. When added to the solution, sodium chlorite ($NaClO_2$) disproportionates to form hypochlorous acid and chlorine dioxide, which is capable of oxidizing silver as shown below:

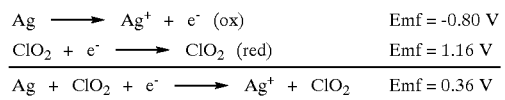

In addition to the reaction shown above, the hypochlorous acid undergoes a redox reaction whereby chloride ions are produced, which then couple with the silver cations to form silver chloride.

The second process is a solubility-driven ion exchange. When, for example, two anions are placed in solution with a given cation, there is a driving force which results in the formation of the metal salt which is less soluble/more insoluble. Because it is difficult to compare solubilities and thus predict behavior when the relative terms "soluble" and "insoluble" are used, solubility is related to a type of equilibrium constant, the solubility product ($K_{sp}$), in order to quantify the degree of solubility in water for a given compound. The solubility product for a salt having one anion and one cation is equal to the concentrations of the dissociated ions of the salt at equilibrium, that is for salt AB, $K_{sp}=[A^+][B^-]$ wherein $[A^+]$ and $[B^-]$ are the concentrations of the A cation and the B anion, respectively. If a salt is fairly soluble, the concentrations of its component ions in solution will be relatively high, leading to a relatively large $K_{sp}$. On the other hand, if a salt is fairly insoluble, most of it will be in solid form, leading to low concentrations of the ions and a relatively small $K_{sp}$. When comparing two salts of the same metal, the salt with the lower $K_{sp}$ is the less soluble/more insoluble of the two. For a system where the salt comprises more than two ions, the equation for dissolution is $X_aZ_b(s) \rightarrow aX^{+c}+bZ^{-d}$ (aq) and the solubility product is represented by $K_{sp}=[X^{+c}]^a[Z^{-d}]^b$ where X is the cation, Z is the anion, a is the number of cations in the salt, b is the number of anions in the salt, c is the charge on the cation, and d is the charge on the anion. Solubility products for most common compounds can be found in reference texts such as the *CRC Handbook of Chemistry and Physics* (CRC Press).

The salts silver chloride (AgCl, $K_{sp}=1.77\times10^{-10}$) and silver iodide (AgI, $K_{sp}=8.51\times10^{-17}$) can be used to illustrate the principle of solubility driven ion exchange. The solubility products for these compounds are both fairly low, but $K_{sp}$ for silver iodide is lower by nearly 7 powers of ten, indicating that it is more insoluble than silver chloride. Thus, if solid silver chloride is placed in a solution containing iodide ions, the equilibrium lies on the side of the silver iodide, and the chloride ions will exchange with the iodide ions so that the more insoluble silver iodide (solid) is formed. On the other hand, if silver iodide is placed into a solution containing chloride ions, the ion exchange will not take place. In this manner, chloride ions in silver chloride coated on the surface of a substrate can be replaced by $^{125}I$ anions to form a radiation source according to a preferred embodiment.

The metal salt layer which is the starting point for the above solution ion exchange process may be formed by a redox process such as that described above, or it may be applied directly by means of sputtering, vapor deposition, or other techniques known in the art. Alternatively, if a redox process described above is performed using an oxidizing solution containing a radioisotope, for example $H_3{}^{32}PO_4$ or $Na^{125}I$, the radioisotope-containing metal salt layer may be obtained directly, eliminating the need for the ion exchange.

Another method for making thin film sources in accordance with the present invention comprises oxidizing a metal, such as those bound to or incorporated in the substrate, and then binding an isotope to the metal oxide. The step in which the metal is oxidized preferably occurs spontaneously in the presence of oxygen, such as in air. Thus, metals such as aluminum and copper, which readily and spontaneously undergo oxidation to form their respective oxides, are preferred. Oxide formation occurs when the metal is exposed to air, but may be enhanced or increased by exposure to oxygen-enriched atmospheres or increased temperature. The binding of the isotope may be performed by immersing the metal oxide in a solution containing isotope ions, either simple or complex. The attraction between the metal oxide and the isotope ions is such that the isotope ions will bind to the metal oxide rather than existing free in solution, such as in the case of binding sodium tungstate to a layer of alumina. This binding or "plating" process may occur either with or without displacement of ions from the metal oxide.

There are several advantages to using the processes above to place active isotopes on a source as opposed to the ion implantation of radioisotopes and nuclear bombardment. Such advantages may include the ability to use a wider range of materials, greater production capabilities, and lack of formation of unwanted isotopes.

Another advantage of the process is that it does not create large quantities of radioactive waste. By using the correct quantity of radioisotope solution, very little waste is produced. Isotopes which are not incorporated into a given source remain in solution and may be used to form another source. Unlike radioactive ion implantation, there is no stray isotope-filled machine chamber that must be cleaned and safely discarded or taken out of use and allowed to "cool."

Yet another advantage of the process is that it allows use of isotopes which cannot be readily obtained on a solid source by the other means known in the art. Furthermore, by using particular long-lived isotopes, a radiation source with a longer half-life can be produced that is capable of delivering a dose with less variation between maximum and minimum. Use of an isotope with a longer half-life may provide for a radiation source which is capable of lowering the amount of radioactivity necessary to perform its function over that which incorporates a short-lived isotope.

Another advantage of the aforementioned process is that the radioisotopes are held by strong atomic-level bonding interactions, and which are highly resistant to leaching or release under physiological conditions or during handling. Additionally, the use of ionic bonding is especially useful for radioisotope species such as iodine-125, as the salt form holds the normally volatile iodine atoms in place.

Another benefit to these solution processes is that the density of activity of a given isotope or multiple isotopes may be controlled by simply controlling the time of immersion and/or the density and amount of metal salt or tie layer on the source.

Another advantage of the thin film source is that the structure lends itself to batch processing. The coating step can be done in relatively large volumes using common chemical attachment techniques found in the photographic film and semiconductor industries. Radioactive isotopes are commonly provided in solutions, so the final production step of adding the isotope may be as simple as soaking the coated substrate in the isotope solution. This can be simply performed in very small or very large sheet sizes. The ability to perform this step in small batches is advantageous because the amount of radiation in process can be adjusted to suit the radiation capabilities of the manufacturer.

The basic method, as discussed in part above, comprises providing a substrate and forming a coating comprising an insoluble metal salt with at least one radioactive isotope species thereon.

One embodiment of thin film source is that which has an isotope layer comprising the gamma-emitting isotope $^{125}I$. One method for making a thin film source having an isotope layer comprising $^{125}I$ is that which uses both solution methods discussed above. First, a substrate is provided that comprises silver or elemental silver is attached to the surface of the substrate using well-known methods such as ion implantation, vapor deposition, sputtering, electroplating, or rolling. The silver is then converted to silver chloride (AgCl) via an oxidation-reduction solution process such as that described above which uses an acidic solution of sodium chlorite to reduce the silver and produce silver chloride. Then the silver chloride-coated source is immersed in an ion exchange solution comprising sodium iodide in the form of $Na^{125}I$, wherein the AgCl is converted to $Ag^{125}I$ on the surface of the source. This manufacturing process may be performed quickly, easily and efficiently. In addition, the I-125 with a half-life of 60 days would provide an equivalent or lower dose of radiotherapy for a longer period of time.

As an alternative to the above method, silver chloride could be directly deposited to the surface of the thin film source by means of vapor deposition or other method known in the art, and then immersed in the ion exchange solution containing $Na^{125}I$.

In one embodiment, a silver foil having a surface area of 4 cm$^2$ was immersed in a solution of 6M HCl and 1M $NaClO_2$ in a 10:1 ratio. A portion of the silver was thereby converted to silver chloride. The foil was then immersed in a bath having about 2 ml of a solution. The solution in the bath contained about 0.07% $Na^{125}I$ in NaI, and was prepared by dissolving 0.5 mg NaI in 2 ml water and adding 4.6 mCi $^{125}I$ into the solution. Following immersion, the resulting activity of the foil was measured at 2 mCi, which, when the amount of carrier (non-radioactive) iodine is factored in, corresponds to about $10^{18}$ atoms of iodine attached to the sheet. In a carrier free solution, this number of I-125 ions would result in an activity of 3 Ci per 4 cm$^2$ of substrate.

Another embodiment of thin film source is that which has an isotope layer comprising $^{32}P$. A thin film source having an isotope layer comprsing $^{32}$P can be made by methods similar to that described above for $^{125}$I using P-32 in the form of orthophosphoric acid (H$_3$$^{32}$PO$_4$). First, a substrate is provided. The substrate may be manufactured to contain zinc or a zinc alloy, or the substrate may be coated with zinc or a zinc alloy by vapor deposition or other methods known in the art. The zinc is then converted to a salt such as zinc fluoride (ZnF$_2$, K$_{sp}$=3.04×10$^{-2}$) via an oxidation-reduction process similar to that discussed above. The source is then activated by immersing the zinc fluoride-coated source in a solution containing phosphate ion in the form of $^{32}$PO$_4$$^{3-}$ or a soluble phosphate salt, whereby the more soluble fluoride ion is exchanged for phosphate to form zinc phosphate (Zn$_3$(PO$_4$)$_2$, K$_{sp}$=5×10$^{-36}$), zinc hydrogen phosphate, zinc dihydrogen phosphate or other zinc-fluorite-phosphate salt combinations, depending upon the reaction conditions.

Alternatively, the substrate may be directly coated with zinc fluoride or other similarly insoluble salt by vapor deposition or other means known in the art, and then placed in an ion exchange solution. Another alternative is to use a solution containing H$_3$$^{32}$PO$_4$ in the oxidation step so that the zinc is directly converted to zinc phosphate containing the radioisotope, thus eliminating the ion-exchange step. Yet another alternative is to deposit or form calcium fluoride (CaF$_2$, K$_{sp}$=1.61×10$^{-10}$) and then expose this to a source of phosphate (orthophosphate) such as H$_3$$^{32}$PO$_4$ or Na$_3$$^{32}$PO$_4$.

There is an additional advantage to using zinc phosphate in the isotope layer. Zinc phosphate is a stable molecule and is often used in the automotive industry for paint adhesion to galvanized steel. Zinc phosphate has anticorrosive characteristics of its own, and has been used in the past to increase the corrosion resistance of steel. A zinc phosphate coating on a source made of steel, such as a wire or seed, may be an advantage to the source even in the case that it is not used as a radiation delivery device.

For sources which comprise a Mylar substrate, CaF$_2$ metal salt tie layer and P-32 as the isotope, in the form of orthophosphate, it has been found that the conditions under which the source is formed effect the amount of P-32 which becomes incorporated into the source (yield). The yield increases with increasing density or increasing thickness of the CaF$_2$ layer, with best results coming when the thickness and density of the CaF$_2$ layer are both increased. An increase in concentration of P-32 in the solution in which the Mylar strips (coated with CaF$_2$) are dipped also increases yield. In one series of experiments, a concentration of 35–50 mCi/ml was found to be optimal. The initial pH has been found to have a substantial impact on the overall yield, as well as the fonration of particular compounds, and the rate of formation. When the P-32 solution has either a pH over 7 or when the pH is very low (1–3), the yields are lower than when the pH is more moderate. As such it is preferred that the pH of the P-32 solution initially be between about 4.5 to about 6.5, with an initial pH of 6.0+/−0.1 being more preferred. Although the pH is important, it has been found that attempts to control pH with buffers may meet with difficulty due to the reactivity of the orthophosphoric acid.

It has further been found that yield is increased if the isotope solution is gently agitated such as by bubbling N$_2$ gas through the solution at a rate of a few bubbles or so per minute. Greater agitation, however, results in a reduction in yield. Yields are enhanced when the P-32 orthophosphoric acid solution is used soon after it is made. Solutions for which use was initiated within 2 hours of its preparation had greater yields than those solutions for which use was initiated 2 days after preparation. The total time for immersion of the CaF$_2$ coated Mylar also affects yield. Yield was found to be greatest after about 5 hours of immersion. Following their removal from the P-32 solution, the Mylar strips or sheets may be dried directly following removal or they may be dipped into acetone prior to drying.

Yet another embodiment of thin film source is that which has an isotope layer comprising tungsten-188 (W-188 or $^{188}$W). Tungsten-188 undergoes beta decay to become rhenium-188 (Re-188 or $^{188}$Re). Rhenium-188 undergoes beta decay as well, but emits a much higher energy particle than in W-188 decay. The W-188 has a much longer half-life than does Re-188, thus the W-188 almost continuously creates more Re-188. This process is known as "generator," and these generator isotopes are referred to together by the shorthand W/Re-188 to indicate the relationship between the species. Generators are attractive for use in radiation delivery devices because they combine the energy levels of a short half-life species with the durability of the long half-life species. It is a general rule that particle energy and half-life are inversely proportional, and that long half-life species are more economical and practical to work with than short half-life species.

W/Re-188 is a parent/daughter radioactive pair, with Re-188 being the more interesting nuclide. Re-188 has a maximum beta energy 25% greater and an average beta energy 10% higher than P-32. Re-188 has the disadvantage of having a gamma component, which requires significant additional shielding. W/Re-188 is a highly favorable beta emitting species for IVRT. The advantage of the W/Re-188 source would be that the source would provide a dose which could be consistently administered over a long period of time. The half-life of W-188 is 70 days as compared to 14 days for the P-32. This represents a consistent dose rate as Re-188, itself a beta emitting isotope, is being produced by the decay of tungsten for a longer period of time.

Tungsten, in the form of tungstate ion (WO$_4$$^{2-}$) may be readily attached to an oxidized aluminum surface to produce a W/Re-188-containing thin film source. An aluminum oxide surface may be attached to the source by sputtering Al$_2$O$_3$, or Al can be attached by implantation or deposition, followed by an oxidation step. Ambient environment will facilitate the formation of Al$_2$O$_3$ from aluminum which can be accelerated by increasing the temperature and/or using an oxygen-rich atmosphere. The aluminum oxide surface may then be immersed in a tungstate containing solution, such as an acidic solution of sodium tungstate (Na$_2$$^{188}$WO$_4$), in order to attach the W-188 to the alumina surface.

Tungsten may also be applied together with a phosphate in a manner similar to that disclosed by Larsen in U.S. Pat. No. 5,550,006, which is hereby incorporated into the present disclosure by this reference thereto. The method disclosed in Larsen is claimed for use in increasing adhesion of organic resists for printed circuits. The method was used to perform a phosphate conversion coating onto copper. A modification of this method may find its application in the radiation delivery devices of the present invention in that many polymers and metals other than copper may be coated with this solution. In this method, phosphate may be in the form of $^{32}$PO$_4$$^{3-}$, tungstate may be in the form of $^{188}$WO$_4$$^{2-}$, or any combination of the isotopes in radioactive or stable form may be used.

Sources employing combinations of various isotopes provide another preferred embodiment in that beta-emitting isotopes may be combined with gamma-emitting isotopes where gamma isotopes can deliver dosage to greater depths.

Thin film sources comprising other metals, metal salts, and isotopes can be made by procedures similar or analogous to the preferred embodiments disclosed above, using materials appropriate for the chemistry of the isotope to be included, as can be determined by one skilled in the art in view of the disclosure herein.

Tie Layers in Thin Film Sources

In some embodiments of the thin film source of the present invention, it may be desirable to provide a tie layer, onto which the isotope layer will be placed. The tie layer may comprise adhesives, chemically activated surfaces, a chemical coating layer, or an organic or inorganic compound. Preferred tie layer materials include metals, alloys, metal salts, metal oxides, PVP, and other polymeric materials.

For some polymeric tie layers, the nature of the tie layer 14 will depend on the isotope to be attached. Many different coatings and attachment technologies are available, and new ones can be developed as applications are developed. For example, Iodine-125 (I-125) can be bound to the substrate by passing it over a substrate coated with a polyvinyl pyrrolidone (PVP) as discussed previously. Other polymeric-type tie layers comprise polymeric materials such as polyesters and polyamides.

Another type of tie layer is the metal-type that which comprises a thin layer of metal, metal oxide, metal salt, or alloy. Depending upon the composition of the other layers and materials in the source, depositing a metal-type tie layer may allow an "alloying" process to take place between the metal of the tie layer and any metals present in the isotope layer. This may serve to enhance the tenacity of attachment of the metal salt, and hence the isotope. This may also occur if the tie layer comprises more than one metal or if more than one tie layer is used in making the source. Alloying of this type is common in the semiconductor industry, wherein a chromium layer is used as an initial layer in the deposition of gold. The chromium is alloyed with the gold in order to increase the strength at which the gold is bound to the substrate. If, for example, the isotope layer comprises a zinc salt, a metal such as copper or aluminum may be used as the tie layer. The tie layer may also be in the form of an oxide, such as alumina ($Al_2O_3$) which may aid attachment by providing oxygen to chemically bind the atoms of the metal salt layer thereby increasing the tenacity of attachment. In one embodiment of source, alumina is deposited on a substrate upon which is placed calcium fluoride. The calcium fluoride may then undergo anion exchange with a source of radioactive phosphate to form a P-32 based thin film source.

A metal-type layer to which the isotope layer is attached may comprise any suitable metal, metal oxide, metal salt or alloy. The layer may be deposited by vapor deposition, sputtering, ion plating, ion implantation, electrodeposition, or other method. When the tie layer is present, there may or may not be a clear distinction between the tie layer and the isotope layer. In performing its function, and depending on the chemistry of the materials involved, the tie layer may become blended, alloyed or intermingled with the isotope layer, thus blurring the lines between the layers. For many of the same reasons, the distinction between the tie layer and a metal-containing substrate layer may also be blurred. In these cases, the term tie layer is meant to be a functional or process-defining definition, rather than a reference to a physically distinct layer of the thin film source.

In another type of system, the tie layer 14 can incorporate a metal exchange surface, which will attach Pd-103 in the form of palladium metal drawn directly from solution. For example, the substrate layer, made from polyimide as disclosed previously, can be coated with reactive metals such as copper, aluminum, or chromium using commonly available techniques such as vapor deposition or sputtering. The coated substrate is then placed in a solution containing the isotope. The difference in oxidation-reduction (redox) potential between the coating metal and the isotope causes the isotope to deposit on the surface of the substrate film. This system can also be used to attach W-188 from a solution of tungsten salts or other metal salt isotopes as well.

Metal isotope species, such as Palladium-103 (Pd-103) or Tungsten/Rhenium-188 (W/Re-188) or Gd-153 can be attached by incorporating a chelating agent onto the polymer substrate, and then soaking the sheet in a solution of Palladium salts, Tungsten salts or Gadolinium salts. These types of chemical technologies can be incorporated into the source design described herein.

An experiment was done to test the effectiveness of using a copper tie layer to enhance the attachment of zinc fluoride onto a Mylar® sheet. A layer of $ZnF_2$ was placed on a first sheet of Mylar by vapor deposition. On a second sheet of Mylar, a layer of copper was placed by vapor deposition, followed by deposition of a layer of $ZnF_2$. The sheets were each placed into solutions of $H_3{}^{32}PO_4$ having similar activities and allowed to react for several hours. The P-32 activity was counted via scintillation counting. It was found that the sheet having the copper tie layer resulted in a greater adsorption of P-32: 71.6% for $Cu/ZnF_2$ vs. 56% for $ZnF_2$ after 1 hour; and 98.4% for $Cu/ZnF_2$ vs. 86% for $ZnF_2$ after 24 hours. Thus, after a significant period of time, the copper tie layer appears to promote and maintain adherence of the zinc salt to the Mylar surface, and can result in a source which has significantly more activity and adhesion than that without the copper tie layer.

Coating Layers in Sources

Preferably, an outer sleeve or coating is provided over the thin film source. An outer coating can increase the abrasion resistance of the source and help reduce activity loss to a point below the regulatory sealed source standard. As used herein, "sealed" radioactive sources are those which have less than 5 nCi of removable activity.

Coating materials are preferably biocompatible, and sufficiently stable to achieve the above objectives. Acceptable materials include polymeric materials such as cyanoacrylates (Loctite, Hartford, Conn.), acrylics, ethylene methyl acrylate (Exxon Chemical Co., Houston, Tex.), ethylene methyl acrylate/acrylic acid (EMA/AA) (Exxon Chemical Co., Houston, Tex.), urethanes and thermal plastic urethane (TPU) (BF Goodrich, Richfield, Ohio), PVDC, PBVC, PE, PET, and combinations thereof. Other preferred coatings may comprise other biocompatible materials, drugs or similar compounds, such as Taxol or heparin. Many methods are available to perform the coating process, such as dip or immersion coating, spray coating, spin coating, gravure or shrink wrap tubing. If thermal curing is required, the curing technique may be any of the various techniques available, such as air, heat, or UV. The thickness of the coating which is formed may be from 1 $\mu$m to 30 $\mu$m or preferably for some materials 10 $\mu$m to 20 $\mu$m, but may be thicker depending upon the isotope permeability of the coating material and the desired physical properties of the finished device (e.g., crossing profile and flexibility).

One embodiment of the present invention has a coating that is formed with cyanoacrylate. Another coating layer is that formed by ethylene methyl acrylate/acrylic acid (EMA/AA) polymer. An aqueous dispersion of this coating material, preferably having a viscosity less than 100 centipoise, allows for use of any of the above-mentioned coating methods. UV curable polyurethane acrylate is also useful as a coating layer material. Yet another preferred coating layer is that formed by Saran. Such a layer may be formed, for example, by immersing the source or a portion thereof into a melt of Saran or a solution containing Saran.

The coating layer may also be formed by a spin coating process. Spin coating the thin film source finds advantage in the flexibility to use coating materials having a wide range of viscosities. Low viscosity liquids may be spun on slowly, while a higher viscosity liquid may be spun at a higher velocity to maintain a thin coating. The substrate may be held in place by fixturing or by vacuum during the spin coating process. In an experiment, a dispersion of cyanoacrylate in acetone was dispensed on top of the metal salt surface while the substrate was rotated at 8000 rpm for five minutes. The resulting thickness of the coating was about 6.5 $\mu$m (0.00025 inch). When this specimen, having the spin-coated surface curable coating of cyanoacrylate was extracted in saline for 8 hours at 50° C., the amount of radioactivity extracted was negligible.

In another experiment, two sources were tested to demonstrate the effectiveness of the coating layer by measuring the amount of removable isotope on coated and uncoated sources. Both sources comprised a Mylar thin film substrate and a $ZnF_2/Zn_3(^{32}PO_4)_2$ isotope layer, with the coated source further comprising a cyanoacrylate coating layer made by dip coating an uncoated source. The test was performed on each source by wiping it with a cotton swab three times on each side. The activity of the swab was measured by scintillation counting. It was found that the amount of removable activity on the uncoated Mylar-based source was 6.76%, while on the coated source the removable activity was merely 0.050%.

Discontinuous or Inhomogeneous Sources

In some embodiments, it may be desired that the source have a composition, structure or other characteristic that is different at one or more parts of its total area, as compared to other portions. Differences include, but are not limited to, varying of activity along the length of a source (discussed below), and the provision of minor discontinuities in the source, and/or the presence or absence of particular layers in one or more parts of a source.

For example, the Mylar or other support structure for carrying the isotope may be conveniently formed in long strips, which may then be helically wound around the balloon and sealed thereto. A minor gap (e.g., generally no more than about 1 mm) may be formed between adjacent windings of the support, thereby providing a helical gap along the length of the source. Alternately, the source may be formed from a plurality of short cylindrical sections, which are aligned axially along the length of the balloon or other mechanical support structure. Each circumferential ring may be separated axially from the adjacent ring by the minor distance. As a further alternative, a plurality of sources may extend axially in parallel with each other around the circumference of the balloon or other support structure. Circumferential spacing of the discrete source sub-assemblies will result in an axially extending gap between adjacent source sub-assemblies. Other patterns may be utilized, depending upon the desired manufacturing technique and desired reduction in the percentage area of isotope coverage of the delivery zone of the catheter. This may be desirable to achieve a variety of objectives, such as enabling a desired manufacturing technique, controlling the isotope density within the delivery zone, or increasing flexibility of the source.

Methods of forming such a discontinuous source include cutting or slitting a source through one or more layers during or after formation of the source, removing portions of a source during or after its formation, or employing masking techniques during the formation of the source, as discussed below. Other techniques having similar results may also be used in making discontinuous sources. The one or more regions having little or no activity which mark the border between the active areas of the source may be of any desired shape or geometry. Patterns of such borders include, but are not limited to, spiral patterns formed by one or more borders, one or more borders along the length of the source (as would parallel the length of a catheter), one or more borders around the width (as would follow the circumference of a balloon), a combination of the length and width as would form a cross-hatched pattern, or other single or combination patterns. The borders may also be random and of no particular geometric pattern.

In making some embodiments of thin film sources, it may be desired that one or more portions of the source or substrate are not covered or coated by particular layers or portions of layers, or that there be differences in the amount of a particular layer material from one portion of the source to another. In such embodiments, the source may be made by the use of masking techniques. In such a technique, the portions of the source or substrate which are to be left alone for a particular step or steps are covered with a piece of a material to serve as the mask. Portions of the source may also be masked for some of the processing time such that the masked portions only receive some smaller part of the treatment in a particular step. The other portions not covered by the mask are treated (reacted, coated) and then the mask is removed. For example, it may be preferred to have a small border of substrate surrounding the portion of the source onto which the isotope layer is placed. Such an arrangement may be preferred to reduce coating of the side surfaces of the substrate by the isotope layer, reduce edge effects or to enable several distinct and separate sources to be prepared on a single sheet of substrate having spaces therebetween which are not coated by isotope to that the individual sources may be separated once they are completely prepared without the risk of radioactive contamination of the blade or other implement which is used to cut or separate the individual sources.

In one embodiment, a plurality of sources comprising a Mylar substrate, alumina tie layer and $CaF_2/^{32}PO_4$ isotope layer are made using a mask. In this method, the Mylar sheet is placed between a plate and a mask. The plate may be formed of glass, metal or other suitable material. The mask is a stainless steel sheet from which several rectangular-shaped portions have been removed. The three pieces (plate, Mylar, mask) are secured together and then placed in a chamber. Alumina, which forms the tie layer, is then deposited on the rectangular-shaped portions of the Mylar which have been left exposed by the mask. Calcium fluoride is then deposited on the alumina. The mask is then removed, and the entire sheet placed in an ion-exchange bath containing $^{32}PO_4^{3-}$ ions to complete formation of the isotope layer. One or more outer coating layers may optionally be placed on the sheet prior to separation of the individual sources. The sources may also be coated individually following separation, such as following incorporation onto a balloon catheter.

The masking technique is described above in terms of making sources having a border of substrate surrounding an active area comprising a tie layer and isotope layer coating the substrate. Although described as such, the masking technique or variations thereof as would be apparent to one skilled in the art, may be used for other purposes in making the sources according to some preferred embodiments, such as placing a coating layer on selected portions of the source, and placing different tie layers on different portions of the source.

Sources may be made having activity which varies over the total area of the source. A source may have one or more areas having greater activity, one or more areas having lesser activity, or some combination thereof. The demarcation between the areas having different activity may be sharp, gradual, or separated by a border as discussed above.

One embodiment of non-uniform activity source is that in which the source, preferably balloon mounted, has an activity greater near the proximal and distal ends of the balloon than it is at the center. A source of this type, one having extended effective radiation length ("EERL") may be used to counteract the normal fall off of radiation delivered to the tissues near the ends of the source as seen with reference to FIG. 17. By increasing the activity at the ends, one makes up for the dosage that would be provided to those tissues in the end regions if there were additional source material extending beyond the end of the source, thus increasing the effective length of the source. In a catheter having EERL sized for use in coronary vessels, the area with greater activity is preferably about 0.1 mm to 3 mm long, more preferably about 0.5 mm to 1.5 mm long, as measured from the proximal and/or distal edge extending towards the center of the source. The activity of the ends is greater than the average activity of the rest of the source preferably by about 10% to 100%, more preferably by about 40% to 60%. However, the activity of the hot ends or any portion of the source should not be increased to a point where the activity is so great as to cause tissue necrosis when used as intended.

Modeling indicates that if the activity per unit area is increased at the end of the source, a more uniform dose profile is obtained. The width of the region at the end of the source in which the activity per unit area is increased is dependent upon the energy of the isotope, but, for example, the lengthened dose profile effect is seen when the end 1 mm of a source is made to have increased activity. For a flattening of the dose profile at 1 mm target depth, an activity that is approximately 50% higher in the end regions will result in the 100% dose (at 1 mm) to be reduced from 3.75 mm to 1.5 mm from the source end while maintaining the same 3 mm 10% to 90% dose gradient as a source not having the higher activity in the end regions.

Such a source may be advantageous in reducing the incidence of "edge restenosis" found in certain intravascular brachytherapy interventions. By maintaining the dose gradient at the end of the source, herein described as the distance over which the dose increases from 10% to 90% of the maximum dose, a proposed alternate mechanism for inducing "edge restenosis" is not increased.

One possible limitation of expandable sources is the target site treatment length, which is effectively the source length minus the placement error. However, the treatment length could be increased by stepping, the serial treatment of the vessel with the source placed at the end of the previous irradiation.

Stepping has two problems that must be overcome: placement of the source during stepping, and the effects of an error in this placement. A marker band on the balloon catheter which delineates the ends of the sources can be helpful in this regard. However, using these markers to align the edge of the source may prove difficult in practice. The error in placement, based upon clinical experience, is approximately 3 mm. Models have been generated to determine the effect of a miss of 3 mm, and it has been found that a gap of 3 mm between sources would likely leave the patient without adequate irradiation to the target tissue. An overlap of about this same magnitude would lead to the dose at the target tissue being about 1.8 times prescribed dose. A serious amount of overlap may lead to the dose being delivered to the vessel wall being significantly higher than that normally considered acceptable.

Stepping of a source (serial movement of the radioactive source along a linear path) through a vessel is a common procedure in brachytherapy and used by some systems in vascular brachytherapy. All stepping reported to this point have involved wire sources or metal capsules situated in the center of the vessel. In this aspect of the present invention proposes the use of an expandable source such as a radioactive balloon catheter in a stepping procedure. Although this disclosure is in terms of a balloon source, it is intended that here, as in all places of the application, a mechanically expandable source may be substituted for the balloon mounted source.

As such, in accordance with another embodiment of a non-uniformly active source is that in which the source, preferably balloon mounted, has an activity which is less near the proximal and distal ends of the balloon than it is at the center. A source of this type is referred to herein as a "stepping source." In this embodiment, the activity would be decreased by about 10%–90%, more preferably about 40%–60% in the end regions. The length of the end regions having a decreased activity is preferably about 1 mm–10 mm, more preferably about 2 mm–5 mm. Furthermore, it is preferred that the size of the reduced activity portions should be selected so as to be approximately equal to the placement error and that the overlap be approximately this same size. This will allow the placement error to be corrected, because that overlap will be between 0 mm overlap and an overlap of two times the positioning error.

Figure 23:
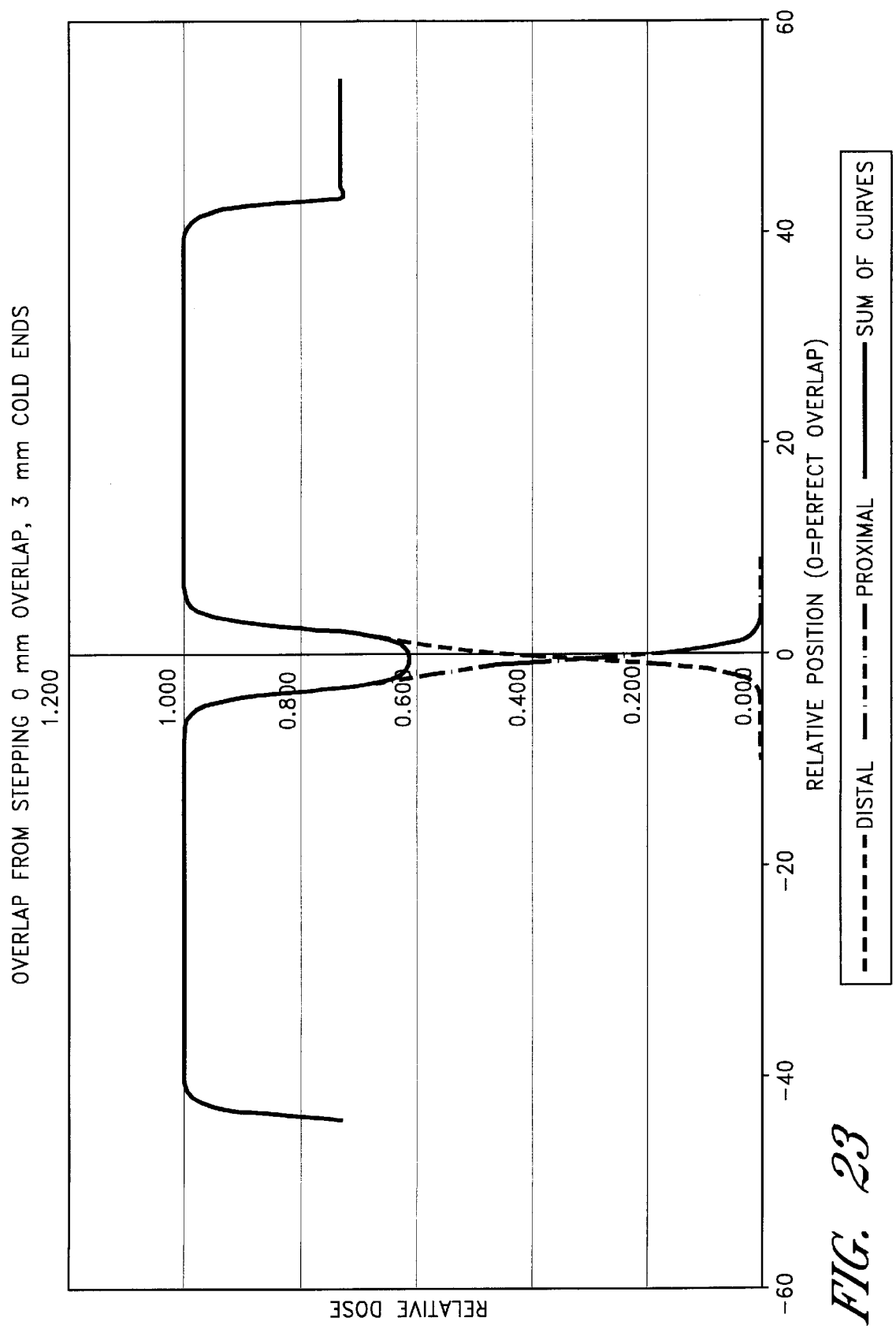
FIG. 23 is a graph showing the results from modeling the dose delivered by a stepping source placed in two positions with 0 mm of overlap.
Figure 24:
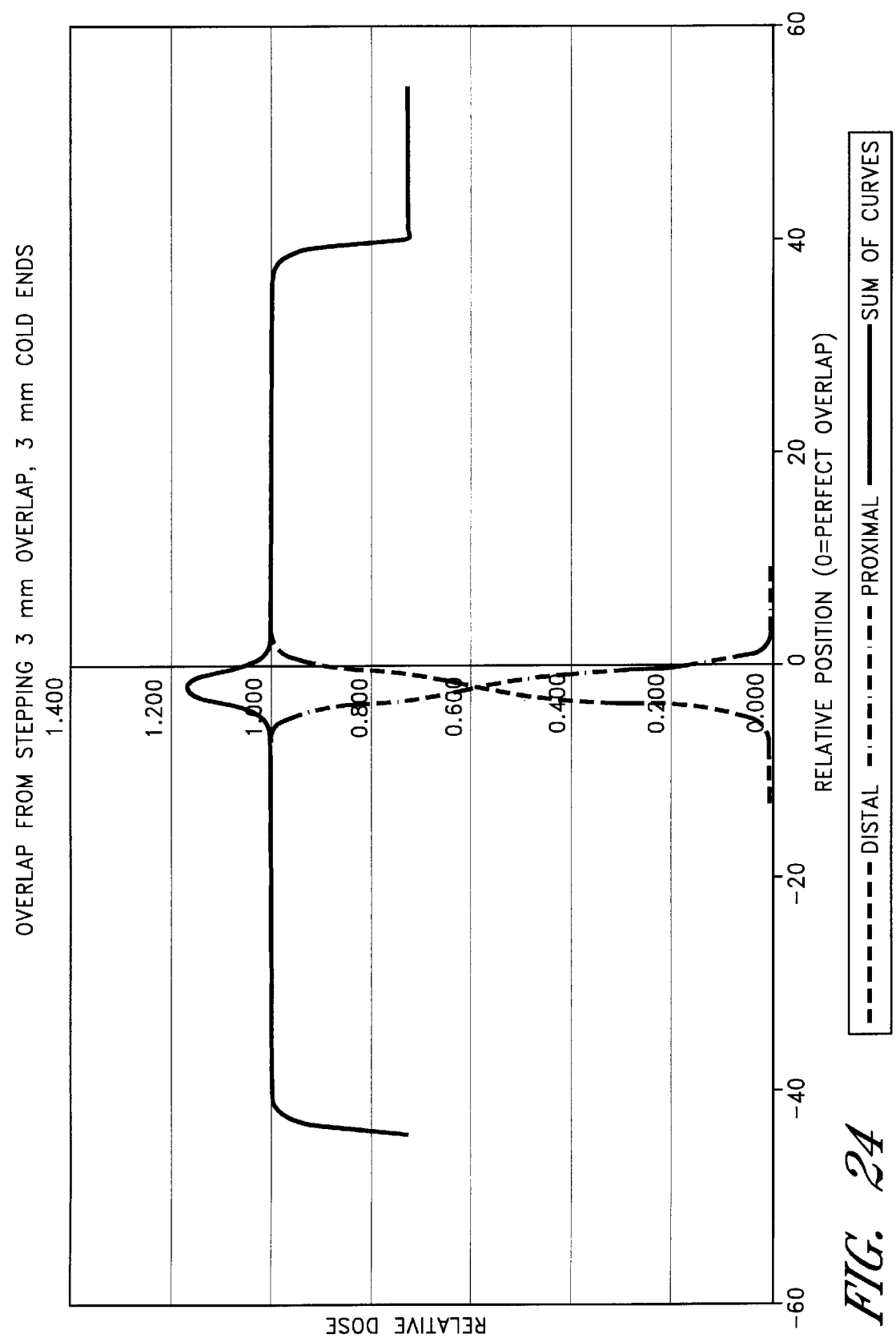
FIG. 24 is a graph showing the results from modeling the dose delivered by a stepping source placed in two positions with 3 mm of overlap.
Figure 25:
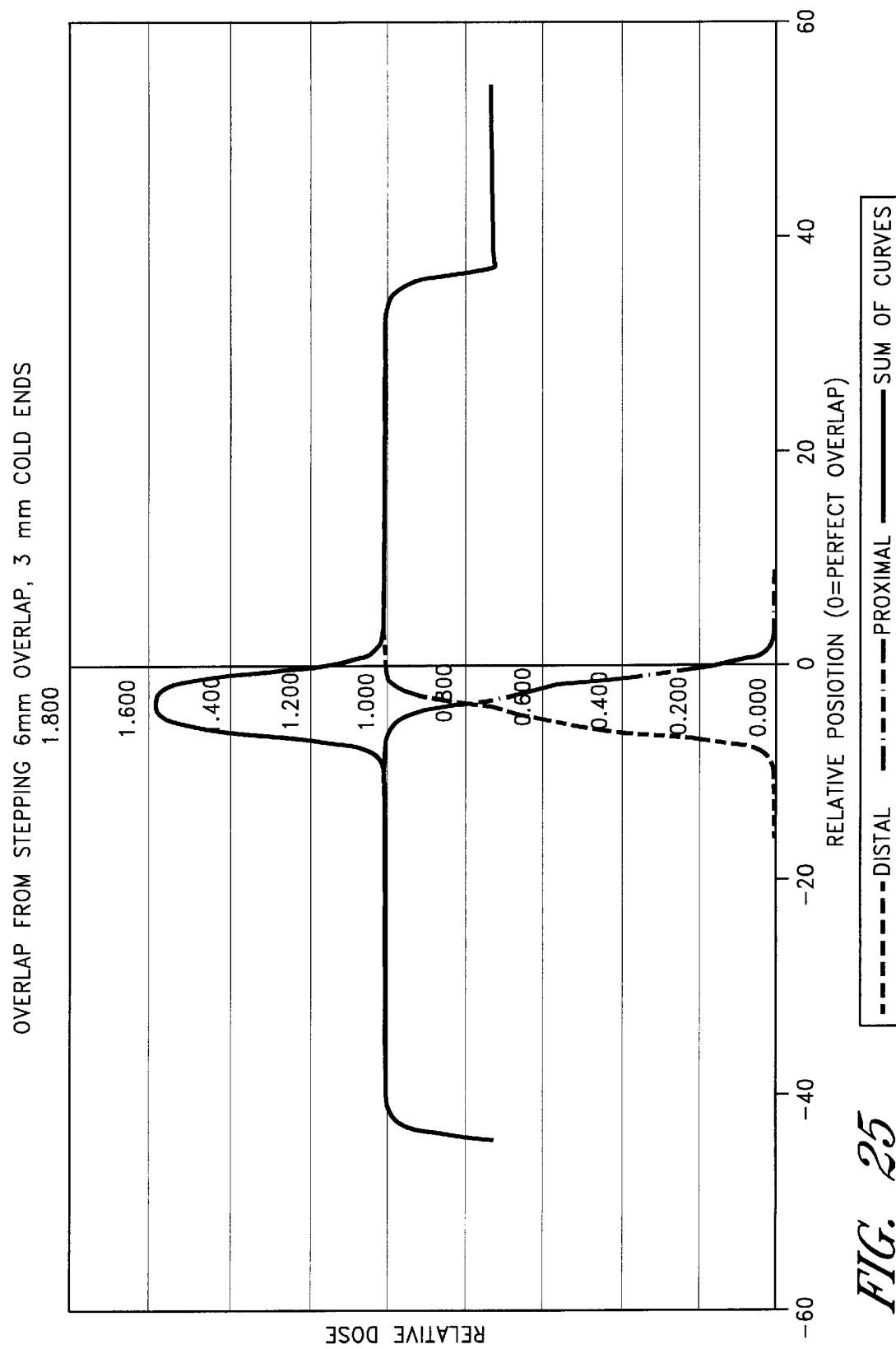
FIG. 25 is a graph showing the results from modeling the dose delivered by a stepping source placed in two positions with 6 mm of overlap.

In the present example, the placement error is 3 mm such that the overlap is between 0 mm and 6 mm. With a decreased activity, the actual dose this overlap will generate is between 0.6 times (at 0 mm overlap) to 1.6 times (at 6 mm overlap) the normal prescribed dose. The results of modeling the situations of 0 mm overlap, 3 mm overlap, and 6 mm overlap for a source having 3 mm "cold" or reduced activity ends is shown in FIGS. 23–25. For example, if 20 Gy is the prescribed dose, this allows a minimum dose of between 12 Gy and 32 Gy to the target tissue and between 36 Gy and 96 Gy to the vessel wall.

Modeling indicates that the target overlap amount should be the distance at the source active end that should have reduced activity. The amount the activity should be reduced will vary on the circumstances, including the minimum dose needed at the target and the maximal wall dose which can be given to the vessel wall. Finally, the decrease should still allow the reduced zone target tissue, when not overlapped, to receive adequate dose.

The general size, shape and other characteristics of a balloon for stepping is similar to those for non-stepping applications as described elsewhere herein, and may include slits or grooves in the source or other means to increase flexibility. However, it is preferred that none of the slits, if present, are included in the overlap zones. Although in normal conditions no problems should occur, in the cases where the vessel is curved and the placement results in an overlap close to the maximum, and overlap of the source at the slit area due to the bending might increase wall dose significantly past the safety zone established for intravascular brachytherapy.

There are several manufacturing techniques which may be used to produce a source that has higher or lower activity at the source ends. Included within these techniques are possibilities of using one or more radioactive isotopes, different geometries, including gradients of activity from normal to higher, possible overlap patterns, and any combination of one or more each of beta, gamma or alpha emitting radionuclides. Exemplary techniques are discussed below.

In one technique, a continuous, uniform matrix of a metal salt or other tie layer is deposited, such as by vapor deposition. Then, all but the area of increased activity is masked and additional active matrix is deposited. When the nuclide (P-32 for example) is exposed to the salt matrix, the area with the thicker vapor deposit will absorb more nuclide, resulting in greater activity in those areas, be they in the center or at the ends.

After the completion of the vapor deposit of the metal salt matrix or other tie layer, the vapor deposited area may be etched such as by photoetching, laser etching, or chemical etching,. This would remove chemical matrix from the central source area or from the ends of the source. When the activity (e.g., P-32) is added by exposure to the isotope solution, it will be absorbed in greater amounts in the thick, non-etched areas.

During the processing to make the active matrix such as by ion exchange, the end portions may be left in the nuclide batch for a longer time period. This will allow the ends to react for a longer time period and hence fix a greater amount of activity. On the other hand, the center could be left in the nuclide batch solution for a longer time period than the ends to make a stepping source.

If it is desired that particular regions have an activity of about 50% of the activity of the rest of the source, a standard two sided source can be designed where the metal salt source matrix area is not placed onto the areas where lower activity is desired. Because only one side will absorb activity in these areas, the activity will be only about 50% of that of the other regions.

Other techniques such as ion implantation could be adapted to increase the P-32 or other isotope implantation at the ends or in the center of the active matrix, as desired.

Two or more isotopes (any type of isotopes, beta, gamma or alpha; for example P-32 and I-125) may also be used in techniques. For example, different radioisotopes can be deposited in set patterns. For example, a gamma emitter could be used as the main dose emitter with extra beta in the middle sections of the source, or a gamma emitter could be used as the main dose emitter but with beta ends to produce a sharpening of the dose profile. In addition, the matrices which uptake the different nuclides could be adjusted by masking the source sheet during deposition so that the placement of the isotopes could be directed to particular regions.

In another technique, one may incorporate the radioactive material into a metal in a uniform manner. A roller may then be used to produce a thin sheet which is capable of being used in balloon angioplasty. The sheet could then be stamped to thin the thickness, and hence decrease the activity, in particular regions, such as in the central portion of the sheet or at the edges.

Alternatively, the radioactive material may be incorporated into a plastic precursor, plastic or similar material, preferably in a uniform manner. The plastic can then be extruded as a sheet where the edges are either thicker or thinner than the rest of the sheet, so as to deliver a greater or lesser dose. The plastic could be molded into flat sheets where the edges are either thicker or thinner than the rest of the sheet, so as to deliver a greater or lesser dose. Alternatively, the plastic material could be spray deposited onto a sheet with masking techniques being employed to allow for areas of greater and lesser activity as determined by the amount of material deposited.

A radionuclide (most metals, e.g., Y-90) can be electroplated/electrodepositied onto a thin metal foil, or onto a plastic sheet coated with a conductive surface. After the main surface is electrodeposited to the desired activity, the regions for which lower activity is desired may be coated with a nonconductive surface (plastic) and electrodeposition continued in the areas for which greater activity is desired.

In another technique, a radionuclide or mixture of radionuclides may be deposited onto a thin, porous surface as a solution or dispersion, to generate a uniform activity on the surface or a portion thereof. Removal of the solvent is then followed by the addition of a second generation of radionuclide (same or different than the first) to the portions of the surface where the second generation of radionuclide is desired by addition of a second round of liquid deposition. Use of a solvent with a high vapor pressure at room temperature is suggested.

If the radioactive material is a metal (e.g., Co-57 or Ir-192), a single-displacement or self-plating reaction can be performed. In this case, a reactive metal is coated onto the active matrix and a metal salt of the radioactive material is applied. The redox reaction leaves the radioactive metal deposited onto the active surface while releasing the active metal as a salt ion.

Lastly, the radioactive nuclide may be applied either during or after surface modification of a plastic substrate. Most commonly this is done by attaching a ligand to the active surface of the substrate, which binds to the radioactive material either through ionic bonding or covalent bonding. Alternatively, the radioactive nuclide can be bonded straight to the surface without the ligand.

Preferred Balloon Catheters

Referring to FIG. 2, there is disclosed a radiation delivery catheter 18 incorporating the thin film source 10 in accordance with one aspect of the present invention. Although the description below is primarily directed to the radiation aspect of the invention, catheters embodying additional features known in the vascular dilatation art, such as carrying implantable stents, drug delivery, perfusion and dilatation features, or any combination of these features, can be used in combination with the balloon or other support structure of the present invention as will be readily apparent to one of skill in the art in view of the disclosure herein.

The catheter 18 generally comprises an elongate tubular body 19 extending between a proximal control end 20 and a distal functional end 21. The length of the tubular body 19 depends upon the desired application. For example, lengths in the area of about 130 cm to about 150 cm are typical for use in radiation delivery by way of a femoral access following or during percutaneous transluminal coronary angioplasty.

The tubular body 19 may be produced in accordance with any of a variety of known techniques for manufacturing balloon-tipped catheter bodies, such as by extrusion of appropriate biocompatible plastic materials. Alternatively, at least a portion or all of the length of tubular body 19 may comprise a spring coil, solid walled hypodermic needle tubing, or braided reinforced wall, as is understood in the catheter and guide wire arts.

In general, tubular body 19, in accordance with the present invention, is provided with a generally circular exterior cross-sectional configuration having an external diameter with the range of from about 0.02 inches to about 0.065 inches. In accordance with one preferred embodiment of the invention, the tubular body 19 has an external diameter of about 0.042 inches (3.2 F) throughout most of its length for use in coronary applications. Alternatively, generally triangular or oval cross-sectional configurations can also be used, as well as other noncircular configurations, depending upon the number of lumens extending through the catheter, the method of manufacture and the intended use.

In a catheter intended for peripheral vascular applications, the tubular body 19 will typically have an outside diameter within the range of from about 0.026 inches to about 0.085 inches. Diameters outside of the preferred ranges may also be used, provided that the functional consequences of the diameter are acceptable for the intended purpose of the catheter. For example, the lower limit of the diameter for tubular body 19 in a given application will be a function of the number of fluid or other functional lumens, support structures and the like contained in the catheter, and the desired structural integrity.

In general, the dimensions of the catheter shaft and balloon can be optimized by persons of skill in the art in view of the present disclosure to suit any of a wide variety of applications. For example, the balloon of the present invention can be used to deliver radiation to large and small arteries and veins, as well as other lumens, potential spaces, hollow organs and surgically created pathways. The present inventor contemplates radiation delivery to the esophagus, trachea, urethra, ureters, fallopian tubes, intestines, colon, and any other location accessible by catheter which may benefit from radiation delivery. This includes surgically created lumens such as, for example, transjugular intrahepatic portosystemic shunts, saphenous vein grafts implanted in a CABG procedure, and others previously identified herein and which will be recognized by those of skill in the art. Thus, although the present invention will be described herein primarily in terms of coronary artery applications, it is understood that this is for illustrative purposes only, and the present invention has much broader applicability in the field of radiation delivery.

Tubular body 19 must have sufficient structural integrity (e.g., "pushability") to permit the catheter to be advanced to a treatment site such as distal arterial locations without buckling or undesirable bending of the tubular body 19. Larger diameters generally have sufficient internal flow properties and structural integrity, but reduce perfusion in the artery in which the catheter is placed. Larger diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 2, the distal end 21 of catheter 18 is provided with at least one inflatable balloon 22. The proximal end 20 of catheter 18 is provided with a manifold 23 which may have one or more access ports, as is known in the art. Generally, manifold 23 is provided with a guide wire port 24 in an over the wire embodiment and a balloon inflation port 25. Additional access ports are provided as needed, depending upon the finctional capabilities of the catheter 18.

The balloon 22 can also be mounted on a rapid exchange type catheter, in which the proximal guidewire port 24 would not appear on the manifold 23 as is understood in the art. In a rapid exchange embodiment, the proximal guidewire access port 24 is positioned along the length of the tubular body 19, such as between about 1 and about 20 cm from the distal end of the catheter.

Referring to the embodiment of the balloon illustrated in FIG. 2, an enlarged zone 32 is positioned between a proximal reference zone 28 and a distal reference zone 30. The relative lengths of each of the three zones may vary considerably depending upon the intended use of the balloon. In general, suitable dimensions of the balloon, both in terms of diameters and lengths, as well as other catheter dimensions, are disclosed in U.S. Pat. No. 5,470,313 to Crocker, et al., entitled Variable Diameter Balloon Dilatation Catheter, the disclosure of which is incorporated in its entirety herein by reference.

In one particular substantially noncompliant balloon application, the central zone 32 has an axial length of about 25 mm, and each of the proximal zone 28 and distal zone 30 have an axial length of about 5 mm. Upon inflation, the proximal zone 28 has an outside diameter of about 3 mm, and the central zone 32 has an outside diameter of about 3.4 mm. The same balloon at 18 atmospheres inflation pressure has an outside diameter of about 3.1 mm in the proximal zone 28 and an outside diameter of about 3.5 mm in the central zone 32. That particular balloon was constructed from PET, having a wall thickness of about 0.0006 to about 0.0008 inches.

In accordance with an alternative embodiment of the balloon of the present invention, illustrated in FIG. 3, the balloon 26 has a generally cylindrical inflated profile throughout its axial working length such as with conventional PTCA balloons. Either the stepped balloon of FIG. 2 or the cylindrical balloon of FIG. 3 can be readily provided with the radiation source 10 in accordance with the present invention.

The overall dimensions of any particular balloon 22 or 26 will be governed by the intended use, as will be well understood to those of ordinary skill in the art. For example, balloons can be inflatable to a diameter of anywhere within the range of from about 1.5 mm to about 10 mm for most cardiovascular applications. For coronary vascular applications, the central zone 32 or overall balloon 26 will normally be inflatable to a diameter within the range of from about 1.5 mm to about 5 mm, possibly larger for certain SVG anastomosis applications, with balloons available at about every 0.25 mm increment inbetween.

The proximal zone 28 and distal zone 30 are generally inflatable to a diameter within the range of from about 1.25 mm to about 9.5 mm. For coronary vascular applications, the proximal and distal zones 28, 30 are preferably inflatable to a diameter within the range of from about 1.25 mm to about 4.5 mm.

The axial length of the central section 32 can be varied considerably, depending upon the desired radiation delivery length as will become apparent. For example, the axial length of the central section 32 may be anywhere within the range of from about 0.5 cm to about 5.0 cm or longer. For relatively focal coronary vascular applications, the axial length of the central section 32 will normally be within the range of from about 0.5 cm to about 4.0 cm, and the balloon may be designed to deliver radiation as well as simultaneously perform conventional PTCA. In a radiation delivery balloon which is not intended to perform PTCA, the axial length of the central zone 32 may exceed the typical length of the lesion, and, in coronary vascular applications, the axial length may be within the range of from about 0.5 cm to about 5 cm or longer.

The axial length of the proximal zone 28 and distal zone 30 may also be varied considerably, depending upon the desired performance characteristics. In general, axial lengths of the cylindrical portion of the proximal zone 28 and distal zone 30 of at least about 3 mm appear useful.

The stepped balloon 22 can be manufactured using any of a variety of techniques which will be understood to those of skill in the art. For example, the balloon can be manufactured by blowing suitable tubing stock into a stepped mold cavity. Alternatively, the tubing stock can be blown into a first mold having a diameter approximately equivalent to the diameter of the proximal section 28 and distal section 30. The balloon can then be blown into a second mold having a larger diameter section corresponding to the central section 32 in the finished balloon. The balloon is inflated into the larger mold under the application of heat, as will be understood by those of skill in the art.

Variations on the configuration of the balloon 22 can be readily constructed, as desired, depending upon the clinical objective. For example, either the proximal section 28 or the distal section 30 can be eliminated. The proximal section 28 or the distal section 30 can alternatively be provided with a diameter that is greater than the central section 32.

In accordance with an alternative embodiment of the balloon of the present invention, illustrated in FIG. 3, the balloon 26 has a generally cylindrical inflated profile throughout its axial working length such as with conventional PTCA balloons. Either the stepped balloon of FIG. 2 or the cylindrical balloon of FIG. 3 can be readily provided with the radiation sources discussed herein in accordance with the present invention.

Figure 4:
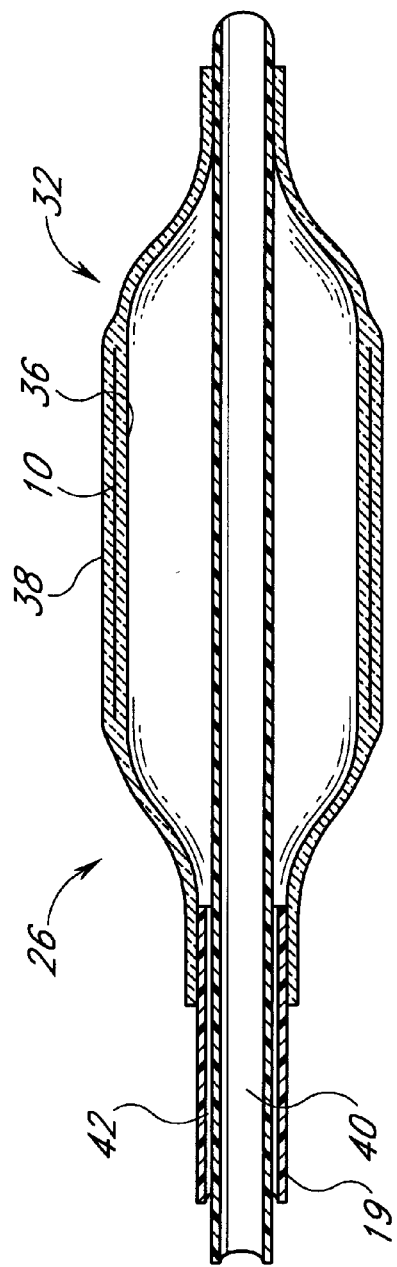
FIG. 4 is an enlarged side elevational cross-sectional view through a balloon incorporating the thin film source of the present invention.

Referring to FIG. 4, there is disclosed a radioactive balloon in accordance with the present invention, configured as in FIG. 3. The balloon 26 comprises a radiation delivery zone 32. The radiation zone 32 comprises an inner balloon wall 36 surrounded by the radiation source 10. Preferably, the radiation source 10 is surrounded by an outer sleeve 38 (sometimes referred to herein as a coating or encapsulant) several embodiments of which are described in additional detail in connection with FIGS. 6 through 9A. In the illustrated embodiment, the radiation source 10 is entrapped between the outer sleeve 38 and balloon wall 36, and the outer sleeve 38 is adhered to the balloon wall 36 or catheter shaft such as through the use of thermal bonding or an adhesive. Suitable adhesives include medical grade UV curable and urethane adhesives known in the art. Any of a wide variety of alternate techniques known to those of skill in the art can also be utilized for securing an outer sleeve 38 to the balloon, sometimes referred to as fusing, heat shrinking, spot welding, and the like.

The sleeve 38 may extend only slightly longer in the axial direction than the axial length of the radiation source 10. The outer sleeve 38 can alternatively extend the entire length of the balloon, or longer, such that it is necked down at the proximal end of the balloon to the catheter shaft and similarly necked down at the distal end of the balloon to the catheter shaft. One outer sleeve 38 comprises 0.0003 inch wall thickness PET tube. Other materials could be polyolefins, nylons, or urethanes, or compounds thereof, and are discussed in detail below.

The balloon 26 is mounted on a tubular body 19, which preferably comprises at least a guidewire lumen 40 and an inflation lumen 42. In the illustrated embodiment, the two lumens 40 and 42 are illustrated in a concentric relationship as is known in the art. Alternatively, the two lumens 40 and 42 can be formed in a side-by-side geometry, (FIG. 5) such as through the use of conventional extrusion techniques.

Figure 5:
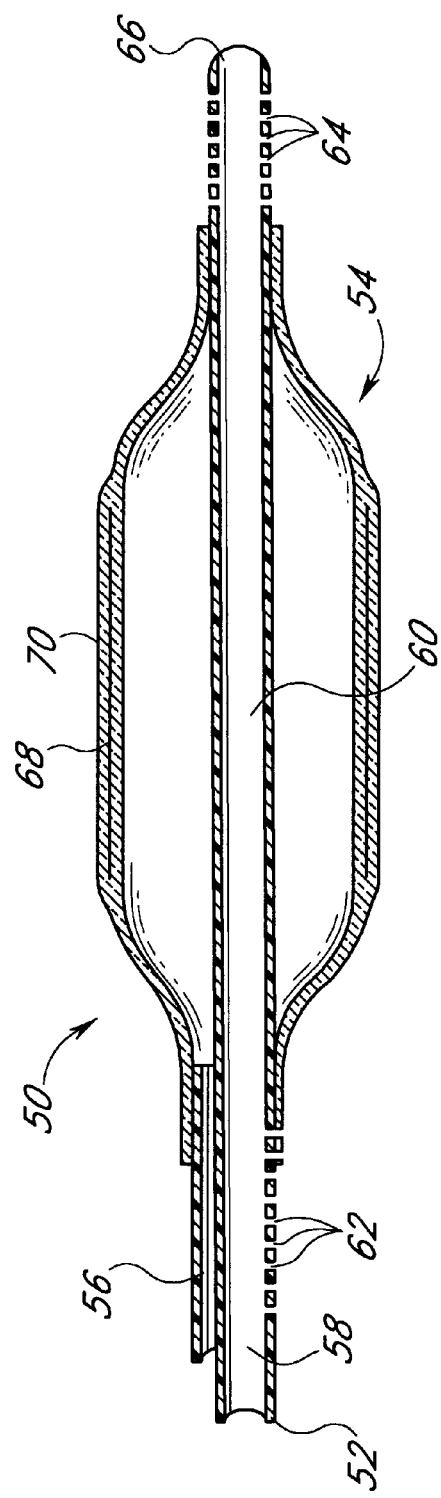
FIG. 5 is an enlarged elevational cross-sectional view of a perfusion balloon incorporating the thin film source in accordance with another aspect of the present invention.

Referring to FIG. 5, there is illustrated a perfusion embodiment of the present invention. The radiation delivery cathether with perfusion 50 comprises an elongate flexible tubular body 52 having a distal balloon 54 thereon. In this embodiment the tubular body 52 is preferably configured in a side by side orientation, as is well understood in the catheter art. Thus, the tubular body 52 comprises at least an inflation lumen 56 and a guidewire lumen 58. Additional lumen may be provided, depending upon the desired functionality of the catheter.

The guidewire lumen 58 extends from the proximal guidewire access port (not illustrated) to the distal guidewire access port 66 as is well known in the art. The proximal guidewire access port may either be on the side wall of the catheter as has been discussed in a rapid exchange embodiment, or at the proximal manifold in an over the wire embodiment. A perfusion section 60 of the guidewire lumen 58 extends through the balloon 54, and places a plurality of proximal ports 62 in fluid communication with a plurality of distal ports 64. In this manner, the guidewire (not illustrated) can be proximally retracted within the guidewire lumen 58 to a position proximal to the proximal ports 62 once the balloon 54 has been positioned at the treatment site. The balloon 54 can be inflated by injecting inflation media through the inflation lumen 56, and the perfusion section 60 permits blood to perfuse across the balloon by way of proximal ports 62 and distal ports 64 and 66.

Figure 10:
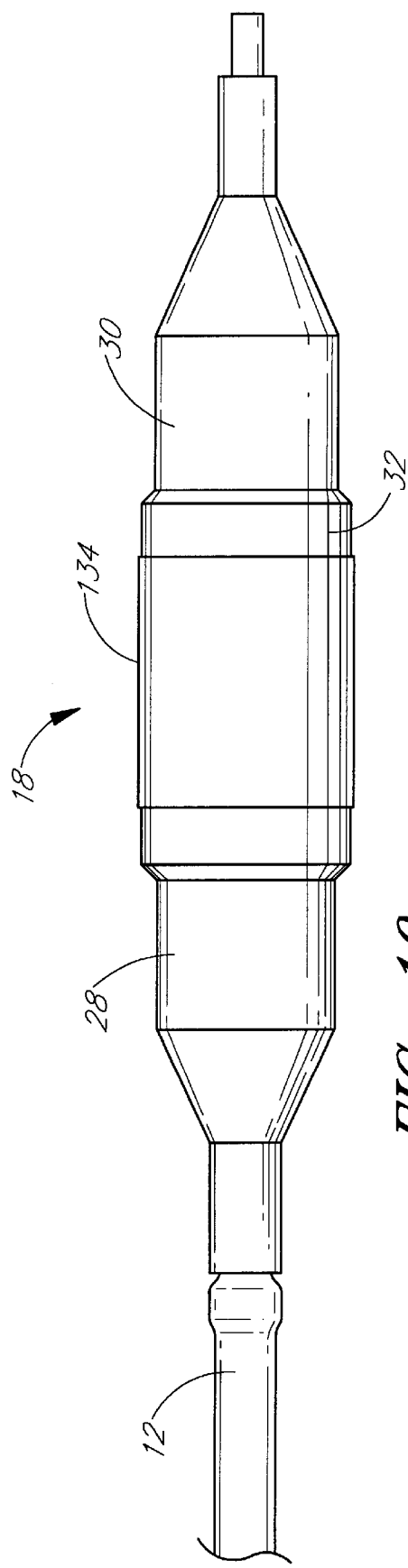
FIG. 10 is a schematic side elevational view of a third embodiment of a balloon catheter in accordance with the present invention.
Figure 11:
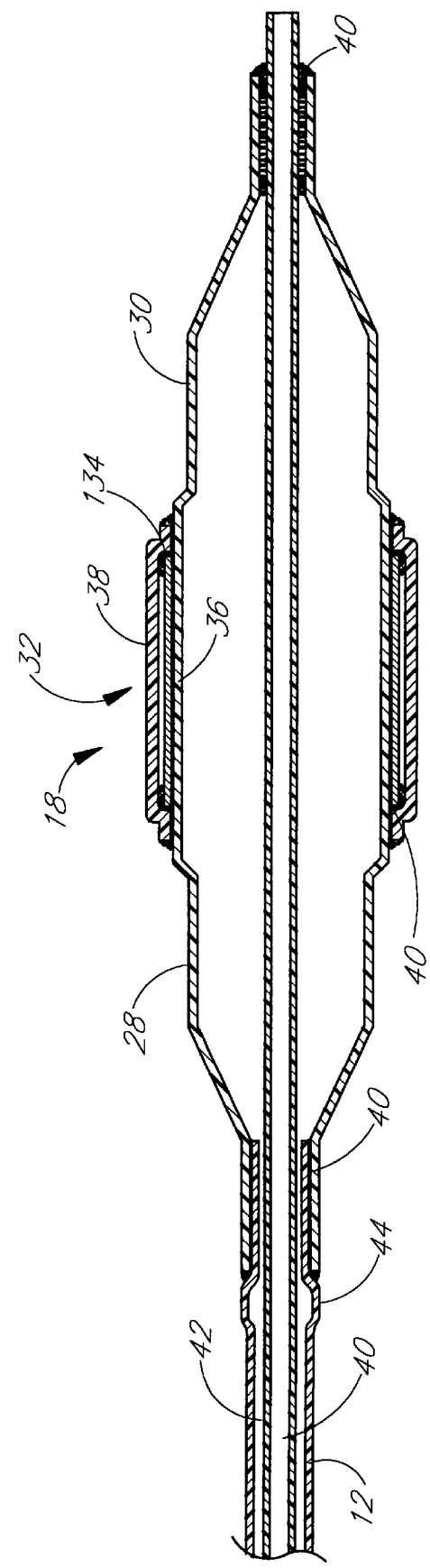
FIG. 11 is a cross-sectional view of a balloon of the type illustrated in FIG. 10.

Referring to FIGS. 10 and 11, there is disclosed a radioactive balloon in accordance with the present invention, configured as in FIG. 2. In general, the balloon 22 comprises a proximal zone 28, and a distal zone 30 having approximately equivalent inflated diameters. The proximal zone 28 and distal zone 30 are separated by an enlarged central zone 32 as has been discussed. Enlarged zone 32 is provided with a radiation source 134, preferably distributed uniformly throughout the circumference of the balloon.

Referring to FIG. 11, the central zone 32 comprises an inner balloon wall 36 surrounded by the radiation source 134. Preferably, the radiation source 134 is surrounded by an outer sleeve 38. In the illustrated embodiment, the radiation source 134 is entrapped between the outer sleeve 38 and balloon wall 36, and the outer sleeve 38 is adhered to the balloon wall 36 such as through the use of an adhesive. Suitable adhesives include medical grade UV curable and urethane adhesives known in the art. Any of a wide variety of techniques known to those of skill in the art can be utilized for securing an outer sleeve 38 to the balloon, such as thermal bonding, heat shrinking, adhesives, spot welding, and the like. Alternatively, one or more bonding layers, as discussed elsewhere herein, may be used. In addition, the sleeve 38 as illustrated extends only slightly longer in the axial direction than the axial length of the radiation source 134.

Figure 12:
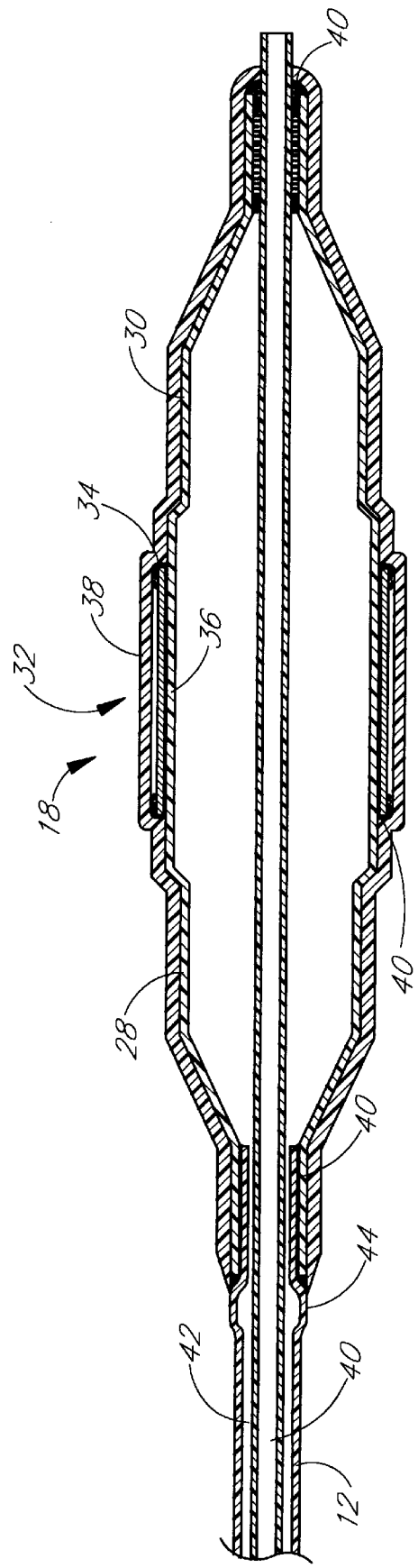
FIG. 12 is a cross-sectional view of an alternate embodiment of a balloon of the type illustrated in FIG. 10.
Figure 13:
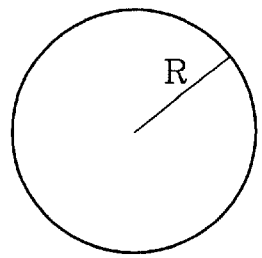
FIGS. 13, 14a and 14b show geometrical relationships which are relevant to theoretical radiation dose calculations.

The outer sleeve 38 can alternatively extend the entire length of the balloon, such that it is necked down at the proximal end of the balloon to the catheter shaft and similarly necked down at the distal end of the balloon to the catheter shaft. One embodiment of a such a necked down outer sleeve is in FIG. 12. Preferably, however, to minimize the amount of material contained in the balloon and minimize the insertion profile of the balloon, the outer sleeve 38 extends only as far axially as necessary to secure and seal the radiation source 134. In an alternate embodiment, the outer sleeve 38 extends from a distal point of attachment to the balloon wall as illustrated in the proximal direction all the way to the catheter shaft, since insertion profile on the proximal side of the central zone 32 is less critical than on the distal side thereof. One suitable outer sleeve 38 comprises 0.0003 inch wall thickness PET tube.

Alternatively, the outer sleeve 38 can be omitted, so long as the radiation source 134 is adequately secured to the balloon.

The tubular body 19 is farther illustrated as having an optional radial enlargement 144, to facilitate in smoothing the transition between the diameter of the tubular body 19 and the adjacent diameter of the proximal end of the balloon as illustrated. The proximal end of the balloon may be secured to the tubular body 19 and the distal end of the balloon may be secured to the wall defining the guidewire lumen through the use of any of a variety of techniques such as adhesives, as illustrated, heat shrinking, and the like.

Mechanically Expandable Sources

The encapsulated thin film source in accordance with the present invention can be formed into any of a variety of configurations for use with a variety of delivery catheters. Although the source is described primarily in the context of a layered source sealed to the wall of a balloon, the thin film source may alternatively be mounted on any of a variety of structures for bringing the source into contact with the vessel wall. For example, the thin film source may be provided in the form of a cylinder or rectangular sheet or a plurality of circumferencially extending strips, which may be unrolled at the treatment site to position the source against the vessel wall, and then rolled back up to a smaller crossing profile for removal. See, e.g., U.S. Pat. No. 5,782,742 to von Hoffmann, the disclosure of which is incorporated in its entirety herein by reference. Alternately, any of a wide variety of mechanical stent deployment catheters which are capable of enlarging a distal zone from a low profile for positioning the catheter within a vessel to an enlarged profile for expanding a tubular stent may be used to carry a tubular thin film source as described herein. In addition, any of a variety of wire baskets or woven wire structures can be utilized to position a thin film source against a vessel wall. See, for example U.S. Pat. No. 6,059,752 to Segal and U.S. Pat. No. 5,484,384 to Fearnot the disclosures of which are incorporated in their entirety herein by reference.

Depending upon the structure of the mechanical deployment device, certain advantages may be achieved compared to a balloon. For example, many of the expandable mechanical structures will enable perfusion through the structure while the source is positioned against the vessel wall. Mechanical deployment structures can also be modified to optimize crossing profile, flexibility, durability in contact with the radioactive source or other advantages or parameters depending upon the specific deployment structure and desired objectives.

Other Radiation Sources

The radiation source used in this or the other embodiments of balloon or support 134 can comprise any of a variety of materials capable of retaining a radiation charge for a sufficient length of time to deliver a predetermined therapeutic amount of radiation to the treatment site. Materials such as phosphorous-32, Yttrium-90, Gold-198 and Iridium-192, among others, may be useful, as well as other metals and non metals having a suitable density depending upon the desired radioactivity and desired deflated balloon profile. In an alternate embodiment of the invention, the balloon material carries the radioactive charge, so that no separate carrier layer is necessary. This could be accomplished by layering and other means discussed in greater detail above, or by doping the balloon material with a radioactive element.

Preferably, the filler is uniformly distributed throughout the circumference of the balloon. Sodium phosphate filler will generally be introduced within the range of from about 0.5% to about 10% by weight, although the optimal weight percent will be determined by compromising various variables such as desired radioactivity, crossing profile, flexibility, and others which will be apparent to those of skill in the art in view of the particular filler.

In one embodiment, the radiation source 134 comprises a metal foil such as gold. The metal foil is preferably evenly circumferentially distributed around the balloon 22, and, most preferably, comprises a continuous or substantially continuous annular sleeve. For example, in an embodiment of the catheter intended to have a 10 mm axial length radiation delivery zone, a rectangular strip of metal foil having a width of 10 mm can be rolled around the balloon through one complete revolution, or two or more revolutions to provide multiple layers, depending upon the thickness of the metal foil and desired radiation charge capabilities. Alternatively, the radiation source may comprise a plurality of annular bands or other configurations as will be apparent from the disclosure herein.

The desired radiation charge will depend in part upon the manner in which the catheter is intended to be handled prior to use at the clinical site. For example, in one embodiment of the invention, the balloon is intended to retain a radioactive charge for an extended period such as two to six months or longer, so that it can be dosed at the point of manufacture and hold the radioactive charge for a reasonable shelf life. Alternatively, considerably shorter dosage retention times are desired if the catheter is designed to be charged at the clinical site, such as within minutes or hours preceding the procedure in which the treatment site within the patient is exposed to the radiation source.

When the catheter is charged at the clinical site, the radiation source 134 may be produced by exposing the carrier (e.g., metal foil) designed to carry the radioactive charge to a stream of neutrons. This technique is known as neutron activation and is one method that is commonly used for transmuting stable (nonradioactive) elements into radioactive ones (An. N. Nesmyanov, *Radiochemistry*, Translated by Artvaz Beknazarov, Mir Publishers, Moscow, 1974). The method is relatively simple, as it involves placing the material to be activated into a flux of neutrons having the required energy. Typically, such a reaction might involve a neutron entering the nucleus of the target atom and a gamma photon exiting it. This is designated as an (n,γ) reaction, and it raises the atomic mass of the original isotope by one atomic mass unit. With such a reaction, a new isotope is made of the same element used as the target material. The amount of activity of the new isotope produced is a function of many variables, including the neutron flux and energy used, the nuclear cross section of the desired reaction, the mass and isotopic abundance of the target material, and the half-life of the new isotope that is produced. This last parameter is significant. If the half-life of the new isotope is very long (e.g., $10^9$ years), then very little activity can be produced. Should the new isotope be stable, then no activity will be produced.

An example of radionuclide production by this method is the transmutation of molybdenum-98 to molybdenum-99 by neutron bombardment [$^{98}Mo(n,\gamma)^{99}Mo$]. This can be written as $^{98}Mo+n\rightarrow^{99}Mo+\gamma$. The threshold reaction energy for this reaction can be calculated by determining the total reaction energy (known as the Q value), and multiplying this by the ratio of the masses of the neutron to the target nucleus (Bernard G. Harvey, *Introduction to Nuclear Physics and Chemistry*, Prentice-Hall, Inc., Englewood Cliffs, N.J., 1969, and Kenneth S. Krane, *Modern Physics*, John Wiley & Sons, New York, 1983). To find the Q value, one sums the mass of the Mo-98 nucleus and neutron, and then subtracts the mass of the resultant Mo-99 nucleus. The resulting difference in mass is converted into energy. Using the masses given by Krane, one obtains: [97.905405u+ 1.00866501u−98.907709u]931.5 MeV/u=5.92 MeV (Mega electron Volts), where u=atomic mass unit (Dalton). This value is actually slightly high, since the energy of the gamma photon has been neglected. The threshold for the desired reaction is thus $$5.92 \frac{1.00866501u}{97.905405u} = 0.061 \text{ MeV}.$$

Since the calculated Q value is slightly high, this threshold energy for the reaction is also slightly high. Neutrons with energies below one MeV are considered "thermal" (see Nesmyanov reference), i.e., this reaction would proceed with very slow neutrons which are abundant in nuclear reactors.

The actual production rate R of the isotope produced by neutron bombardment (e.g., Mo-99) is governed by the equation:

$$R = \phi \sigma M_t \frac{ap}{MW} N_0$$

in which the production rate is in reactions per second, the neutron flux $\Phi$ is in neutrons per square centimeter per second, the nuclear cross section $\sigma$ is in barns (1 barn=$10^{-24}$cm$^2$), and the mass of the target is designated as $M_t$. The number of atoms of interest per molecule of target material (given by its chemical formula) is a, and p is the abundance of the isotope of interest. The atomic weight of the target atom is designated as MW, and $N_0$ is Avogadro's number (6.023×10$^{23}$) (*CRC Handbook of Radiation Protection and Measurement* Volume I, Allen Brodsky, Editor, CRC Press, Inc. Boca Raton, Fla., 1985). The production rate can be increased by increasing the flux $\Phi$, target mass $M_t$, or the percent of abundance of the isotope of interest in the target material. Concerning the production of Mo-99 from Mo-98, Mo-98 is only 24.1% abundant in nature. Using enriched molybdenum that is >90% in the 98 mass will greatly increase the production rate.

The activity of the material that is produced is a function of the new isotope's half-life and irradiation time. The activity A, produced is determined by the formula $$A = R(1 - e^{\lambda t})$$

in which e is the base of the Naperian or natural logarithm (i.e., 2.718 . . . ), and the elapsed time is t. $\lambda$ designates the decay constant of the isotope that is formed, and is calculated as the Naperian logarithm of two divided by the half life of the isotope. (It is important that time is measured in the same units in all of these calculations.) It should be noted that after a given time, a saturation point is reached, and no further activity is produced by neutron bombardment, i.e., the material is decaying away as fast as it is being produced. This represents an upper limit for the specific activity of a given isotope that can be produced under these conditions.

The above procedure is useful for producing radioactive isotopes of the same element that is used as the target material (e.g., producing Au-198 from Au-197). Sometimes a different element can be produced by bombarding the target atom with neutrons. Bombarding aluminum with thermal neutrons will yield Al-28[$^{27}$Al+n→$^{28}$Al+γ], a reaction called an (n,p) reaction. However, if neutrons with an average energy of 8.1 MeV are used (neutrons with an energy. 1 MeV are termed "fast"), the following reaction occurs: $^{27}$Al+n→$^{24}$Na+α. Another useful reaction using fast neutrons is the bombardment of sulfur (natural sulfur is 95.02% isotope of mass 32): $^{32}$S+n→$^{32}$P+p. The threshold energy of this reaction can be calculated (as in the Mo case), with the following results: [31.972072u+1.00866501u− 31.973908u−1.00727647u]931.5 MeV/u=33.12 MeV. (Once again the masses are from Krane.) The threshold for the desired reaction is:

$$33.12 \frac{1.00866501u}{31.972072u} 3 = 1.04 \text{ MeV}.$$

Experimental observation and measurement show that this is indeed the threshold energy for this reaction, and it reaches its maximum yield at neutron energies of about 2.9 MeV (CRC).

In one embodiment, the radiation source 134 comprises a gold foil, having an axial length as mounted on the balloon of about 1.0 cm, a width sufficient to be rolled up into a cylinder having a diameter of about 3 mm. The thickness of the gold foil is about 0.0003 inches. These dimensions provide a volume of 7.18 E−4cm. The density of gold, according to the Merck Index, is 19.3 gm/cm$^3$. Such a density gives a mass of 13.9 mg of gold, or 4.23 E+19 atoms of gold to activate.

Gold-197 (Au-197) has a nuclear cross-section of 98.65 barns. The half-life of gold-198 is 2.696 days. Using a reactor having a thermal flux of 2 E+12 neutrons/square cm/second at 100% Au-197 (naturally occurring) and ignoring burn-up (conversion to Au-199), the following relationship between irradiation time and resultant activity should be observed:

TABLE 1

| Irradiation Time | Resultant Activity |
|---|---|
| 0.25 hours | 0.605 mCi |
| 0.50 hours | 1.21 mCi |
| 1.0 hour | 2.41 mCi |
| 2.0 hours | 4.79 mCi |
| 3.0 hours | 7.15 mCi |
| 5.0 hours | 11.8 mCi |
| 8.0 hours | 18.6 mCi |

The resultant activity as a function of irradiation time illustrated in Table 1 can be varied considerably by selecting a different thermal flux than 2 E+12 neutrons/cm$^2$/second. For example, higher resultant activities for the stated irradiation times can be achieved by selecting higher E values. A thermal flux of 6 E+12, 8 E+12, 10 E+12, 12 E+12, or higher can be used depending upon the material of the radiation carrier, the thickness of the radiation carrier layer, the indwelling time within the patient, and the desired clinical result. Optimizing the radiation dose parameters can be readily accomplished through routine experimentation by one of skill in the art in view of the disclosure herein, depending upon the desired clinical method.

Although the parameters will most likely be optimized through clinical procedures, the radiation dose required can be roughly estimated from physical considerations. It is helpful to first consider the case of a radiation point source, such as phosphorous-32 (P-32), several of whose key radiation parameters are listed here:

Half-life=14.28 days
Maximum Beta Energy=1.71 MeV
Average Beta Energy=0.6948 MeV
Betas Per Nuclear Disintegration=1.00
Maximum Range in Tissue=0.80 cm Where the maximum range in tissue is related to the maximum beta energy.

The following calculations give the activity that yield a dose of 12 Grays in 5 hours to the tissue surrounding the radiation point source. It is assumed that the radionuclide will bombard the tissue continuously for five hours and then be removed. When the implanted P-32 is a point source, the distribution of beta particles will be in a spherical pattern emanating from the center of a sphere with a radius of 0.80 cm, as illustrated in FIG. 5. Since the volume of a sphere is $4/3\pi r^3$, the corresponding spherical volume of tissue is 2.17 cm$^3$. Assuming a density ($\rho$) of the tissue essentially equal to that of water, this gives a mass of 2.17 grams. If a total absorbed dose of 12 Grays is required over a period of 5 hours, the initial dose rate will decrease only slightly with the 14.28 day (342.72 hour) half life of P-32. This gives a decay constant ($\lambda$) of 0.002002/hour [1n2/342.72 hours]. The accumulated dose in 5 hours can be determined exactly by the integral $$12 \text{ Grays} = {}_0\int^5 R_e^{-0.002002t} dt4,$$

where R is the initial dose rate in Rads per hour, and t is the elapsed time. Evaluating this integral gives a value for R of approximately 2.4 Grays per hour. It should be noted that the 14 day half-life is sufficiently long relative to the 5 hour irradiation time that the decay of the P-32 could have been ignored.

The initial activity required to deliver the desired dose can be determined by beginning with the definition of a Gray, namely, one Joule of energy absorbed per kilogram of material. Since 2.4 Grays/hour are absorbed by 2.17 grams of tissue, this amounts to $$2.4 \frac{J/kg}{hour} \times 0.00217 \text{ kg} = 0.00520 \text{ J/hour}$$

of absorbed energy by the tissue, which is equal to $$3.25 \times 10^{10} \frac{MeV}{hour} 6.$$

Since 0.6948 MeV of energy are released per average disintegration, this gives a required P-32 activity of $4.67 \times 10^{10}$ disintegrations per hour, or $1.30 \times 10^7$ Bq, or 351 $\mu$Ci.

As an alternative to P-32, other radionuclides such as Yttrium-90 (Half-life=64.0 hours; Maximum Beta Energy= 2.27 Mev; Average Beta Energy=0.9314 MeV; Betas Per Nuclear Disintegration=1.00; Maximum Range in Tissue= 1.11 cm); Gold-198 (Half-life=2.696 Days; Maximum Beta Energy=961 keV; Average Beta Energy=316.3 keV; Betas Per Nuclear Disintegration=1.00; Maximum Range in Tissue=0.42 cm); and Iridium-192 (Half-life=74.2 Days; Maximum Beta Energy=666 keV; Average Beta Energy=222 keV; Maximum Range in Tissue=0.25 cm) may also be useful.

Figure 14A:
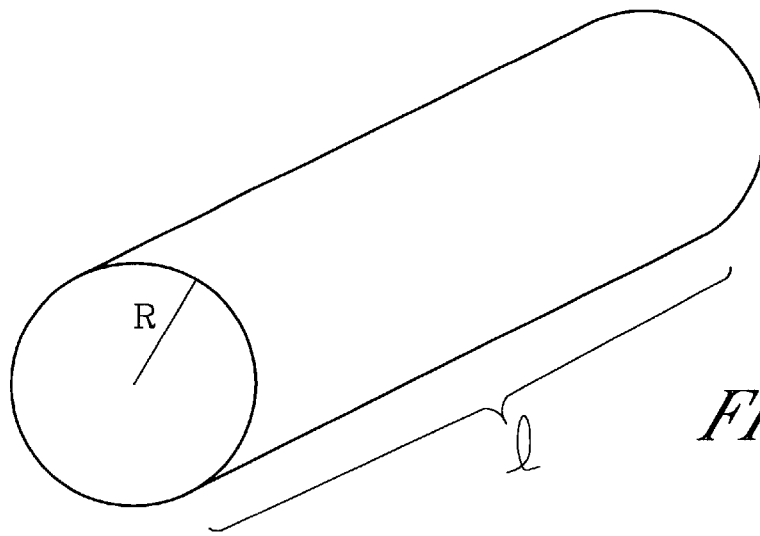
Figure 14B:
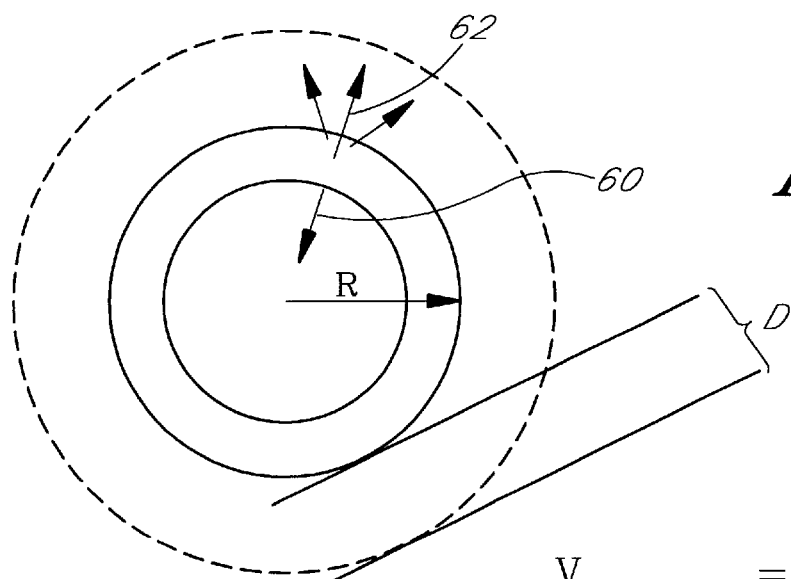

There are differences in geometry between the radiation delivery balloon of the present invention and a point source which lead to significant differences in how radiation is distributed in the tissue, as illustrated in FIGS. 14a and b. Whereas a point source results in a spherical distribution of radiation, the catheter produces a distribution of radiation that has cylindrical symmetry. Assuming a radiation penetration depth of D and a catheter of length I and radius r, the volume of tissue affected by a catheter wrapped in a radiation source can be roughly estimated as $$Vol_{cath} = l\pi(r+D)^2 - l\pi r^2$$

This quantity depends explicitly on the catheter's length l and radius r.

Actually, radiation leaving either a point source or a cylindrical one has a distribution of beta decay energies, and there is a nonuniform distribution of energy deposited within the absorbed tissue: it is easier to expose tissue closer to the radiation source to 12 Grays, as tissue further away from the radiation source is partially blocked. This means that in order to expose all of the desired tissue to a desired dose such as 12 Grays, tissue closer to the radiation source will be exposed to more than 12 Grays, and more radiation is required than a simple model of uniform distribution would suggest. Furthermore, some of the radiation may pass through the tubular body 19 before reaching tissue (i.e. radiation whose direction of propagation is given by arrows 160 as opposed to 162) depending upon the stopping power of the inflation media and materials that make up the catheter. In any case, those skilled in the art will appreciate that the optimal radiation dose and related parameters will be determined by routine experimentation and clinical study.

In an embodiment using PET or other substantially non-compliant material, it is unnecessary that the gold foil or other radiation delivery media be able to elastically expand with inflation of the balloon. Instead, the balloon can be assembled in the inflated configuration, and then deflated so that the gold foil is folded with the PET balloon into the insertion profile.

If the catheter used is one which is not active upon shipment, including but not limited to one using a metal foil source such as gold, the catheter is shipped without a charge and is then placed in a reactor and charged for a sufficient period of time to dose the balloon at the clinical site. The balloon is thereafter percutaneously inserted and transluminally advanced through a patient's vasculature, to the treatment site. At the treatment site, the balloon is expanded to position the radioactive delivery layer against the vessel wall.

The catheter may be provided with a perfusion conduit. In general, perfusion capabilities can be added to the radiation delivery balloon of the present invention by providing an axially extending perfusion lumen through the balloon (not illustrated). One or more perfusion apertures is provided on the catheter shaft on the proximal side of the balloon, for permitting communication between the perfusion conduit and the outside of the catheter, and one or more perfusion apertures is provided on the distal side of the balloon for permitting blood to bypass the balloon as will be understood by those of skill in the art. Any of a variety of perfusion structures can be utilized, such as any of those disclosed in U.S. Pat. No. 5,344,402 to Crocker entitled Low Profile Perfusion Catheter or U.S. Pat. No. 5,421,826 to Crocker et al. entitled Drug Delivery and Dilatation Catheter Having a Reinforced Perfusion Lumen, the disclosure of each of which is incorporated in its entirety herein by reference.

Additional Aspects of Thin Film Sources

As discussed elsewhere herein, the balloon 54 is provided with a thin film source 10 which may comprise one or more layers of radioactive thin film source. The thin film source 10 may be adhered to or otherwise carried by the inside surface or outside surface of the balloon wall and may be further entrapped within an outer tubular layer 70 as illustrated. Alternatively, the thin film source 10 is adhered to or carried by the inside surface or outside surface of the balloon wall without an outer layer 70. Tubular layer 70 preferably is positioned concentrically about the thin film source 10 and heated or otherwise bonded to attach the layer 70 securely to the balloon. The axial length of the tubular layer 70 on, for example, a 3 cm long balloon, may be anywhere within the range of from about 15 mm to about 150 mm or up to the entire working length of the balloon measured along the axis of the catheter. In one embodiment, it is between 32 and 40 mm.

In any of the foregoing embodiments, the isotope layer 16 may comprise either a homogenous isotope population, or a blend of two or more isotopes. For example, a blend may be desirable to achieve a desired combination of half life, activity, penetration or other characteristics in the finished product. Two or three or four or five or more different isotopes may be dispersed uniformly throughout the isotope layer 16, or may be concentrated in different zones along the isotope layer, depending upon the desired activity profile in the finished thin film radiation source.

In accordance with another aspect of the present invention, the thin film radiation source is applied to a delivery structure such as a balloon in a manner that permits radially asymmetric delivery. This may be desirable for treating only a selected site within the circumference of the arterial wall, such as in the case of an eccentric stenosis.

In this embodiment radioisotope is provided only along a portion of the circumference of the delivery structure such as a balloon. The radioisotope zone may comprise anywhere in the range of from about 10% to about 70% of the total circumference of the balloon, and, in one embodiment, is within the range of from about 30% to about 50% of the total circumference of the balloon. This may be accomplished in any a variety of manners, such as masking the thin film prior to application of the isotope, applying a blocking layer to block release of radiation from portions of the circumference, and the like as will be apparent to those of skill in the art in view of the disclosure herein. In one embodiment, a thin film sheet is prepared as has been described herein, except that radioisotope is only adhered to the thin film substrate in a series of discrete zones which are separated by nonradioactive portions of substrate. The radioactive zones can be spaced apart along the substrate sheet to correspond to the circumference of the delivery balloon, so that when the radioactive thin film is wrapped around the balloon, the radioactive zones align with each other to provide a radioactive stack on only a predetermined circumferential portion of the balloon.

Thus, at least a first and a second zone can be provided on the thin film source in accordance with the present invention. In one embodiment the first zone is radioactive and the second zone is not radioactive. In another embodiment, the first zone has a first radioactive activity and the second zone has a second, lesser radioactive activity. Alternatively, other characteristics of the radioactive source can be varied between the first zone and the second zone, depending upon the desired delivery performance. These zones may be applied in a manner that permits axially asymmetric delivery.

In accordance with another aspect of the present invention, a balloon catheter may be constructed which allows for delivery of radiation to differing sizes of lumens. In such a device, the balloon preferably comprises a compliant material. The substrate for the source may be either the balloon itself or another thin film of a compliant or elastomeric plastic. As the pressure inside the compliant balloon is increased, the outer diameter of the balloon will increase. Thus, a single balloon catheter may be used to treat different size lumens by simply varying the pressure and hence the inflation diameter of the balloon.

The increase in diameter will result in a decrease in density of isotope atoms per surface area. By adjusting the dwell time, the predetermined dosage can be delivered. For example, a 20 mm balloon having an outer diameter of 2.0 mm and $10^{17}$ atoms of isotope on the surface will result in a density of $7.96 \times 10^{14}$ atoms/mm$^2$. If this balloon were pressurized to increase to a 2.5 mm diameter, the density would decrease to $6.34 \cdot 10^{14}$ atoms/mm$^2$. This is a 20% decrease, resulting in a need for a 20% increase in dwell time to achieve an equivalent dose. There may also be a slight decrease in balloon length with increased diameter of inflation. This change, however, is dependent on the level of compliance and may be negligible in most cases, but is easily remedied by careful selection of balloon size.

Sources Containing Fused Layers

Details of an outer layer configuration for enhancing the seal for containing the radioactive source are illustrated in FIGS. 6 and 7. The present inventors have determined that one reason for failure of certain radiation delivery balloon designs to adequately contain the isotope is due to the separation of the cover sheet from the balloon or catheter shaft at the axial ends of the balloon. Another reason for failure may occur in the clinical environment as balloon may get punctured or torn on a stent or calcium. The repeated inflation and deflation which is common to dilatation procedures and/or regulatory approval protocols can cause a separation at the bond between the cover sheet and the balloon. The failure of the cover and the balloon to hold together is typically due to processing of materials disclosed in the prior art for use as balloon and cover sheet elements, such as polyethylene, EMA, nylon and polyethylene terephthalate. These materials, as previously disclosed, provide a mechanical radiation barrier seal rather than a chemical or fused seal to the radiation source, catheter shaft and underlying balloon. Thus, heat and adhesives are utilized to create mechanical barriers which lack sufficient stability when they are worked in the manner often required during balloon inflation and deflation.

In accordance with the present invention, the encapsulant cover layer and the balloon materials are fused together at least on either side of the source. A "fused" attachment as that term is used herein is readily distinguishable from purely mechanical attachment (e.g. heat shrink or wrap), wherein the layers may become delaminated or otherwise separated as a consequence of excessive pressure or inflation cycling. In a "fuse" type of attachment, the two or more starting layers of the source and coversheet cannot be peeled apart without tearing through all layers. The tear line between the original layers is oftentimes partially or completely obscured. A fuse as contemplated in the context of the present invention thus has a significantly reduced risk of separation or delamination during use, and may therefore be worked by inflation and deflation without separation. An outer sleeve such as sleeve 38 or other encapsulant disclosed herein is at least fused to an underlying surface on each of the proximal and distal ends of the source to encapsulate the source in a cylindrical envelope carried by the balloon. In a preferred embodiment, the fused seal extends throughout the entire axial length of the source such that fluid will not be drawn between layers enveloping the source should any such layers be punctured or torn and then inflated and deflated. The fused bond may be formed between at least some of the layers, such as between the outer cover and the balloon, to provide a sealed encapsulated source on the balloon.

In accordance with one aspect of the invention, a polyethylene tube is coextruded with an ethyl methacrylate (EMA) layer over the PE to form a PE balloon with an EMA outer bonding layer, or the two materials are coextruded together. The extrusion process, performed at about 300–400° F., leads to a complete attachment between the EMA and PE that can undergo the balloon forming process without forming gaps or voids in the PE/EMA border. The cover tube is formed in the same way as the balloon, only the EMA is the first (inner) layer and the PE is the second (outer) coextruded layer.

The balloon is thereafter attached to the catheter shaft according to methods well known to catheter manufacturers and discussed elsewhere herein. After the source and cover layer are assembled onto the balloon, the entire assembly can be heat fused. At this point, the EMA layer of the PE balloon directly opposes the EMA layer on the PE encapsulant layer proximally and distally of the source, forming a PE-EMA-EMA-PE stack. In embodiments where the source also comprises EMA or a material with similar melting point characteristics, the EMA layers of the balloon and encapsulant fuse together along the length of the source as well, forming an EMA fuse layer 72 with the isotope suspended therein, as illustrated in FIG. 8. Since the EMA melts at a much lower temperature than the crosslinked PE, the cover can be heat fused in a mold under moderate temperatures (200–300° F.) and pressures (1–4 ATM) without damaging the balloon. An annular fused seal is thus formed at least both proximally and distally of the source to fully encapsulate the source within the wall of the multilayer balloon. In the case of a source having compatible fusing surfaces, the seal continues throughout the source length increasing the strength of the body of the balloon from about 120 psi to about 210 psi.

EXAMPLE 1

One set of ten samples constructed with a PE-EMA-source-EMA-PE stack as described above but with an annular source layer which is not fusible with the EMA was placed in an experimental fixture capable of repeatedly inflating and deflating the balloon. The PE was 0.00052" thick and the EMA was 0.000052" thick. Each balloon/source was 2.5 mm in diameter and 22 mm in length. The balloon was submerged within a test tube containing a methylene blue dye (0.5%) in order to detect separation between the cover and balloon layers. The balloons were inflated to 3 ATM and deflated after 10 seconds for over 250 cycles without detecting any leaks. A second set of ten samples constructed with gaps at the balloon necks using misformed encapsulant and little or no heat fusion in the EMA layer were similarly tested and each sample displayed dye present in the source area after 10–20 cycles.

EXAMPLES 2

A set of ten samples constructed as described above (PE-EMA-source-EMA-PE stack) with source activities in the 1 mCi range were constructed and tested as above. The PE-EMA-EMA-PE stack extended proximally of the source for about 5 mm and distally of the source for about 5 mm. The devices were first wipe tested to establish that no removable surface activity was present on the samples. The test tubes containing one balloon each were removed from the fixture every twenty cycles and surveyed with a Geiger counter for removed activity. No removed activity was found after 200 cycles.

Thus, one embodiment of the sealed source configuration in accordance with the present invention is schematically illustrated at FIGS. 6 and 7. In these figures, the bonding surfaces are shown for clarity as discrete layers 36b and 38b. In preferred embodiments, however, the layers 36b and 38b would be fused together on at least a portion of their lengths and preferably throughout the length of the source such that the interface between the layers would be partially or fully obscured.

In the illustrated embodiment, a radioactive source 10 is encapsulated between a balloon 36 and an outer encapsulant 38 as has been described. In the illustrated embodiment, however, the balloon comprises an inner support layer 36a and an outer bonding surface 36b. The encapsulant 38 comprises an inner bonding surface 38b and an outer support layer 38a. As illustrated, bonding surface 36b from the balloon is in contact with bonding surface 38b both proximally and distally of the radiation source 10. The source includes an isotope, and may comprise a single layer or a multilayer stack as is discussed elsewhere herein. This structure at least enables a fused annular seal beyond the axial ends of the source. A further embodiment provides a seal completely through the source zone. This can be accomplished by forming the source substrate out of appropriate materials.

In one polyethylene embodiment, the outer encapsulant support layer 38a comprises polyethylene and the bonding layer 38b comprises EMA. The inner balloon support layer 36a comprises polyethylene and the balloon bonding layer 36b comprises EMA. This construction permits a fused seal between the encapsulant and the balloon, as has been discussed, to prevent leakage of radioisotope.

A schematic diagram showing assembly of a sealed source is illustrated in FIG. 8. An extruded tube 44 comprised of an outer bonding layer 36b, preferably of EMA over an inner structural layer 36a preferably of PE, which forms the balloon, has the radiation source layer 10 placed or formed thereon. The coextruded cover tube 46, comprised of an inner bonding layer 38b, preferably of EMA, and an outer structural layer 38a, preferably of polyethylene, is placed over the balloon and source. Following application of heat and at least a slight pressure to ensure contact between the bonding layers, the sealed source 48 is formed, in which the two bonding EMA layers 36b and 38b have fused at least proximally and distally of the source to form what functions as a single layer 72 with the isotope suspended therein.

In one of the simplest forms, the source comprises an isotope attached to or carried on a bonding layer. The bonding layer may be that on either the sheet or encapsulant, or it may be a separate structure. Due to the physical properties of most suitable bonding materials (low softening or melt point), if the source is a separate structure, it preferably also includes at least one layer having greater structural integrity than the bonding layer. This construction can be accomplished in three portions or layers: two bonding layers (B) with an isotope-containing layer (I) between them, or (B)-(I)-(B) in shorthand. It may be desirable to add an additional support layer (S) to one or both bonding layers or replace one or both bonding layers with a support layer to provide greater support to the source for ease of processing or use, if the assembly is not otherwise sufficiently supportive for a given application. Such sources include, in shorthand, (SB)-(I)-(B), (B)-(I)-(BS), (SB)-(I)-(BS), B-I-S or S-I-S. It is preferred that the bonding layers all comprise fasable materials and preferably comprise a common material.

The materials which form the structural layers and bonding layers preferably have one or more characteristics which aid the layers performing their functions within the structure. The bonding layer and support layer materials preferably have a strong bond between them. A strong bond may be the result of chemical or mechanical attachment, or some combination of the two, and it may be achieved by coextrusion or coinjection of the materials. It may also be achieved by casting one material over the other or injection molding one material over the other. Attachment of the materials may also be enhanced if the bonding and support layers have at least one material in common (e.g. a small amount of the support layer material is incorporated into the material which forms the bonding layer). Another preferred characteristic is for the melting or softening points of the bonding layer and support layer to differ, with the melting or softening point of the bonding layer being the lower of the two. This allows for the structure or shape of the source to be maintained by the support layer(s) when the bonding layers are fused by the application of heat. In some embodiments, it is preferred that the support layer material be generally non-compliant.

In preferred embodiments, the isotope-containing layer (I) above is a multilayer isotope-containing substructure or radiation source which can be combined with one or more bonding layers or bonding-support stacks (SB) and assembled into a larger structure. For example, when the radiation delivery source is the balloon of a balloon catheter, it may be desirable to prepare the isotope-containing substructure portion of the source separately. Following its preparation, the isotope-containing substructure, preferably in a tubular form or a rolled-up sheet, is then placed upon or into the balloon of a balloon catheter and then covered with a single or multilayer encapsulant structure and heated to fuse the bonding layers. Pressure may also be placed on the assembled stack such as by inflation within a capture tube with heating to further facilitate the fusing process. In another embodiment, the source may comprise two substructures, a balloon and an encapsulant, wherein either the encapsulant substructure or the balloon substructure incorporates the isotope-containing layer. In another embodiment, the source may be placed inside the balloon and the inner diameter of the source is then optionally encapsulated.

By using source preparation methods as described above, the non-radioactive substructures may be prepared ahead of the time of use and then assembled with a recently-made isotope containing portion of the source just prior to use or shipment. Thus, one may create separate subassemblies or substructures and assemble them just prior to shipment or use of the catheter device. Although the discussion which follows is in terms of a balloon catheter and a tubular source, one skilled in the art would recognize that the source may be used for applications other than a balloon and that the same concepts apply to other geometries such as a sheet.

Thus, in one embodiment, the isotope-containing multilayer substructure may simply comprise a bonding layer-isotope (BI) two layer stack. If this substructure were assembled into a source with a balloon and encapsulant, each of which comprise a bonding layer and a structural layer, the source would have the following layer structure: (SB)-(BI)-(BS). Alternatively, one can protect the isotope-containing layer of the substructure from damage during later processing by applying a coating layer (C) to the isotope-containing layer and/or other exterior layer, such as is described supra, to form sources of the type (SB)-(BIC)-(BS), and (SB)-(CBIC)-(BS). In preferred embodiments, the coating layer is the same material as or is heat fusible or mechanically or chemically adherent to the bonding layers.

In other embodiments, the isotope-containing substructure further comprises a structural layer, such as to aid in formation and processing of the source. Thus the substructure could take the form (BSI) or (SBI), with the latter being preferred such that when it is combined with the other portions to form the full multilayer source, the bonding layer upon which the isotope-containing layer sits can fuse with the bonding layer on either the balloon or the encapsulant. In the latter structure, (SBI) it is preferred that there be an additional bonding layer (BSBI) such that the substructure bonding layers may fuse with bonding layers on both the balloon and encapsulant. Substructures containing support layers may also have an additional protective coating layer on the isotope-containing layer, e.g. (BSIC), (CBSIC), (SBIC), (BSBIC), and (CBSBIC).

In accordance with the present invention, one preferred embodiment of the source is represented by the shorthand (SB)-(BSBIC)-(BS). A source of this type is shown in FIGS. 9. FIG. 9 is an exploded cross-section showing the source during the assembly of the three portions: encapsulant, isotope-containing substructure, and balloon. The upper two layer portion is the encapsulant comprising a bonding layer 38b and a structural layer 38a. The lower two layer portion is the balloon comprising a bonding layer 36b and a structural layer 36a. The isotope-containing substructure or radiation source 10 initially comprises seven layers. The core of the substructure is a three layer stack comprising a structural layer 74a sandwiched between two bonding layers 74b. On one bonding layer sits the isotope containing layer, which is a two layer structure comprising a tie layer 14 and an isotope layer 16. The isotope layer 16 preferably comprises a metal salt or oxide with at least one isotope. The tie layer 14 and isotope layer 16 is of the type described supra and as such, there may not be a clear visual distinction between the layers. The outer layers of the substructure are coating layers 17.

Figure 9A:
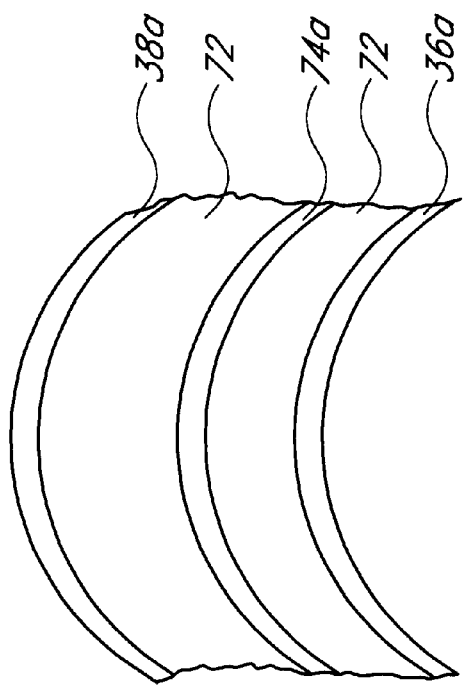
FIG. 9A is a view as in FIG. 9, in which the bonding layers have been fused.
Figure 9:
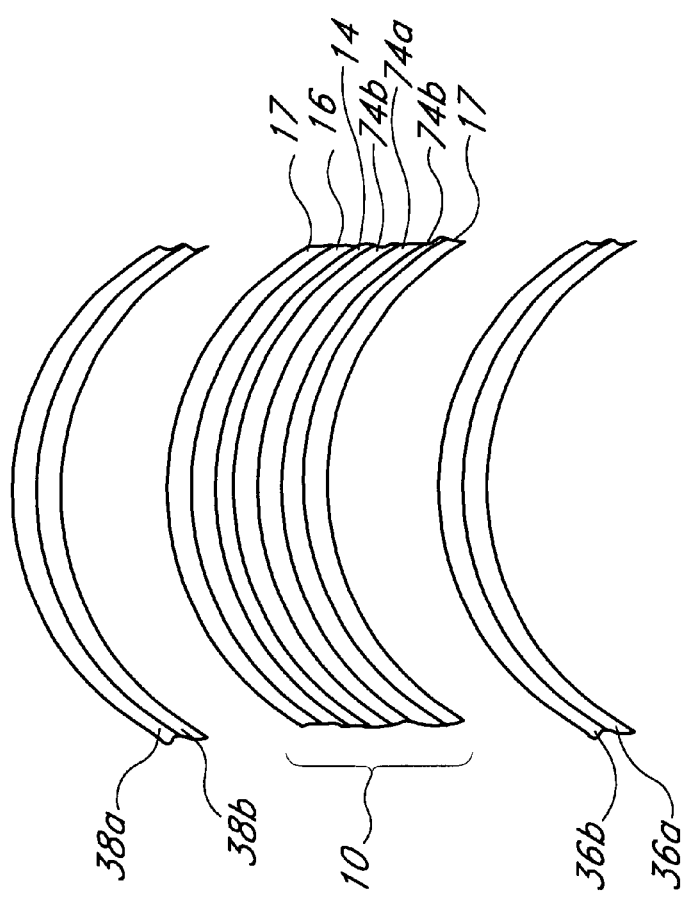
FIG. 9 is an exploded cross-sectional view through a portion of a multi-layered sealed source embodiment of the present invention, prior to fusing the bonding layers.

FIG. 9A illustrates the final configuration of the source of the type in FIG. 9, following the application of heat, either with or without pressure, to fuse the various bonding layers. The source of FIG. 9A comprises two layers of fuse 72 sandwiched among the structural layers of the balloon 36a, isotope-containing substructure 74a, and encapsulant 38a. The upper layer of fuse 72, between the isotope-containing substructure 74a and encapsulant 38a support layers, is that which has the isotope embedded therein.

To aid in the formation of the complete fuse through coating layers and isotope-containing layers, the materials which form those layers preferably have a melting point similar to that of the bonding materials, comprise a material common with the bonding materials, or have some other physical or chemical property which aids them to become part of a fuse layer 72. Alternatively, the coating layers and/or isotope-containing layers may be porous or comprise a plurality of apertures through which the bonding materials may form fuses or spot welds to bind the layers together.

Thus, using the principles described above, a wide variety of multilayer sources encompassed within the present invention can be prepared by combining layers, creating substructures, and fusing bonding layers in the multilayer stacks formed.

In the above multilayer sources, the fuse between the bonding layer adjacent to the isotope-containing layer in the substructure and the bonding layer in either the balloon or encapsulant may extend through the isotope-containing layer such that the isotope-containing layer is suspended within a larger layer of bonding material, as shown in FIG. 8. FIG. 8 depicts a tubular structure, as would exist in a tubular source or in a cross-section of the center portion of one embodiment of balloon catheter incorporating a sealed source of the present invention. Such a fully radially extending fuse may be enhanced for certain materials if the isotope-containing layer is permeable or has gaps therein, such that it does not create a barrier to the fusing of the two bonding layers. This is a benefit in that even in the case of a tear such as by calcium or a stent strut, only the edge surface area of the tear would be exposed to the bloodstream.

In experiments, balloons having a full seal were slit axially and then allowed to soak in a rhodamine dye solution to determine the degree of infiltration of fluid into the breach. After several minutes, the dye solution could be seen staining the slit. There was, however, no separation of fused layers adjacent to the slit and no lateral infiltration of dye solution between fused layers of the source, indicating that the solution was exposed to only that small portion of the edge of the source in the puncture channel itself In addition, the completely fused structure increases the surface area of fuse and decreases the potential of a seal breach due to overhandling or exposure of balloon material while the product is on the shelf.

EXAMPLE 3

A sample was constructed of a PE-EMA-source-EMA-PE in which the tubular source was of configuration EMA-PE-EMA-isotope with an intentional leak channel therein. The sample was manufactured with about 1 mCi of activity. After twenty cycles of inflation/deflation in a test tube, the radiation leakage was undetectable by a Geiger counter. The balloon was then intentionally slit and allowed to soak for 15 minutes. The resulting radiation leakage was slightly above background. This would represent a design that, upon tear, would allow the radiation to be nearly completely obscured from the outside and meet the 5 nCi removable activity requirement of a sealed source.

The optimal balloon bonding surface $36b$ and encapsulant bonding surface $38b$ can be determined through routine experimentation by those of ordinary skill in the art in view of the disclosure herein, and depending upon the desired balloon $36a$ material and encapsulant $38a$ material. In addition, variations can be made on the foregoing stack depending upon the construction materials and the desired process parameters, particularly temperature, for a given balloon construction. In general, the desired result is a fused or blended polymeric material along the length of the radiation source 10, such as may be readily accomplished through heating certain types of materials under compression. This may be accomplished in a 4-layer stack (not counting the source) as illustrated where the balloon material $36a$ and encapsulant material $38a$ will not fuse as has been described herein. Alternatively, a 2-layer stack may be used where the balloon material $36a$ and the encapsulant material $38a$ will fuse to form a sealed bond. A 3-layer stack such as a balloon $36a$, an encapsulant $38a$, and one of $36b$ or $38b$ may be positioned therebetween, either radially inwardly from or radially outwardly from the radiation source 10.

The encapsulant 38 may extend any of a variety of lengths along the balloon 26, to produce proximal and distal annular seals of the desired length. In the illustrated embodiment, the encapsulant 38 extends beyond the working length of the balloon by about 5–8 mm in each of the proximal and distal directions to maximize the total surface area of the proximal and distal seals. The encapsulant 38 may extend proximally farther than the balloon neck, and distally farther than the balloon neck if desired. Encapsulant lengths of only slightly longer than the axial length of the source 10 may also be utilized, provided the materials of the stack provide a sufficient seal over the shortened axial length.

The fused encapsulant layer in accordance with the present invention can be utilized to provide a sealed source using a source produced by any of a variety of isotope attachment techniques. Thus, in addition to using the various binding chemistries disclosed supra, the source layer 10 may comprise any of a variety of alternative chemistry schemes, including chelating chemistry reactions, ion implantation, and others as will be understood by those of skill in the art.

Spaced-Back Sources

A P-32 beta radiation source in tissue attenuates about 13% of its dose within a distance of 0.1 mm and about 50% of its dose within about 0.5 mm of its surface. This physical attribute creates the advantage, in balloon or mechanically expandable sources, of achieving the desired dose rate with less activity as compared to line sources such as wires and seed trains. The deployment or expansion of the preferred catheter-borne radiation source embodiments of the present invention can give a relatively high dose to the tissues on the surface of the vessel if the source is fully deployed against the tissue. The dose to the tissue lining the vessel drops to about 85% if the surface of the source is spaced back as little as 0.1 mm from the vessel wall. In this same position, the dose delivered at a depth of 1.0 mm into the vessel wall is reduced only slightly, being about 97% of the dose which would have been delivered if the source were directly opposed to the tissue lining the wall.

This radiation distribution phenomenon may be exploited by employing an expandable source that deploys to a controlled distance that is smaller than the reference diameter of the target tissue. For example, in a 3.0 mm artery, deploying a source to a diameter of about 2.5 mm (spaced back from the artery surface by 0.25 mm) would give about 93% of the dose at a depth of 1.0 mm that would be given if the source were deployed at 3.0 mm. The surface dose to the arterial wall would, however, see a much more drastic reduction in dose, in that only about 45% of the dose delivered by a fully deployed source (3.0 mm) would be seen by the wall when the source is spaced back by 0.25 mm.

Benefits gained by spacing back the source may be best applied in the field of peripheral brachytherapy where high activity sources are employed to treat the larger vessels. If the target dose is approximately 14 Gy at 2.0 mm depth, this would translate to about 45 Gy at 1.0 mm depth and about 320 Gy at the surface. If, however, the source were spaced back from the wall by about 0.5 mm, the same 14 Gy at 2.0 mm would result in about 144 Gy into the vessel wall. As such, by spacing back a high activity source, one could safely employ sources which might otherwise cause tissue necrosis if allowed to remain in contact with the vessel wall for an ordinary treatment time.

The amount of spacing back is preferably about 0.05 mm to about 1.0 mm, more preferably about 0.5 mm to 1.0 mm. The spacing back could be accomplished in several ways. A spacer of the desired thickness formed from one or more bands of material, coiled wire, polymeric tube or other type material could be placed over the source prior to deployment. A thicker outer coating could be used on the source to gain some additional distance between the source layer and the vessel wall, or the source could be placed on the inner surface of the balloon or substrate. It should be noted that if a stent is being deployed or if the vessel already has a stent in place, the stent may also act as a spacer.

One preferred design for spacing back is a multi balloon system. One example of preferred dual balloon system is found in U.S. patent application Ser. No. 09/040,172, filed Mar. 17, 1998, entitled Dual Catheter Radiation Delivery System. In a preferred dual balloon system, there is an outer balloon to be deployed to the diameter of the vessel and an inner balloon to deploy a source to about 0.5 mm less in diameter than the vessel or to reside about 0.25 mm from the surface of the target tissue. In alternate embodiments, one or both of the balloons may be replaced with structures having other means of deployment, including unwinding and mechanical expansion. The inner source may be any of the types described herein. The outer balloon is preferably similar to angioplasty type balloons and constructed from polyethylene, PET, Nylon and the like.

Another spacing system includes an elastomeric type tube. The tube is designed to expand under pressure to a diameter slightly larger than that of the balloon carrying the source. This may be accomplished by adjusting the durometer of the material, the wall thickness or by simply adding a strain component into the design of the balloon. An example of this would be to use a material such as silicone or Kraton and stretch it to 25% longer than its relaxed length and then bind it to the outer diameter of the distal shaft portion of the catheter. A tube of elastomeric material is preferred because, upon deflation or release of pressure, the material would return to its natural tubular shape. This will allow the delivery system to be pulled into a guide catheter without the formation of wings as sometimes happens with preshaped angioplasty balloons. In addition, if the source balloon had a memory fold, the outer elastomeric balloon would encourage the fold and add the compression to decrease the overall profile back through the artery during removal. The attribute of decreased profile upon pressure release may find benefit in the case of multiple balloon inflation/deflation cycles that are required for long treatment times or those systems not having perfusion capability. The reduced profile would increase the opportunity to reside in situ during the brachytherapy treatment decreasing the chances of operator error in placement of the source. This is especially true for the case of in-stent restenosis where misplacement of the radiation source with reference to the injured artery at the edge of the stent can result in an edge restenosis or "candy wrapper" effect. As above, the source balloon may be replaced with a structure having another means of deployment, including unwinding and mechanical expansion.

In accordance with one method of the present invention, a balloon catheter such as any described above is percutaneously inserted and transluminally advanced through a patient's vasculature, to the treatment site. At the treatment site, the balloon is expanded to position the radioactive delivery layer against the vessel wall. The balloon remains expanded for a sufficient radiation delivery time, and is thereafter deflated and withdrawn from the patient.

If delivery times greatly in excess of 3–4 minutes are clinically desirable, the catheter 18 may be provided with a perfusion conduit such as that illustrated in FIG. 5. Any of a variety of perfusion structures can be utilized, such as any of those disclosed in U.S. Pat. No. 5,344,402 to Crocker entitled Low Profile Perfusion Catheter or U.S. Pat. No. 5,421,826 to Crocker et al. entitled Drug Delivery and Dilatation Catheter Having a Reinforced Perfusion Lumen, the disclosure of each of which is incorporated in its entirety herein by reference.

Alternatively, the balloon may be periodically deflated to permit perfusion and then reinflated to contact the vessel wall. For example, the balloon may be up for one minute and down for one minute through a series of cycles until the total cumulative inflated time is within the range of from about 5 to about 20 minutes. Up for two minutes or three minutes for every minute down may alternatively be used, depending upon perfusion needs.

In accordance with another aspect of the method of the present invention, the radiation delivery and balloon dilatation catheter of the present invention is utilized to simultaneously dilate a stenosis in a vessel and deliver a treating dose of radiation. The catheter is percutaneously introduced and transluminally advanced through the arterial system to reach a stenosis. The balloon is positioned within the stenosis, and inflated to expand the stenosis as is known in the art. During the expansion step, the balloon is delivering a treatment dose of radiation to the vessel wall. The balloon may then be left in position in the inflated profile optionally with perfusion for a sufficient period of time to deliver the desired dose of radiation. The balloon is thereafter deflated, and the catheter is withdrawn from the treatment site.

In accordance with a further aspect of the method of the present invention, the radiation delivery catheter of the present invention may be utilized to simultaneously implant a stent while delivering a dose of radiation. In accordance with this aspect of the method, a stent is positioned on the radiation delivery balloon prior to percutaneous insertion within the patient. The balloon carrying a stent thereon is thereafter percutaneously inserted and transluminally advanced through the patient's vasculature to the treatment site. The balloon is expanded at the treatment site to expand the stent, while simultaneously delivering a dose of radiation. The balloon is thereafter deflated, and withdrawn from the patient, leaving the expanded stent in position at the site.

In accordance with another aspect of the present invention, there is provided a method of treating a previously implanted stent or graft with exposure to a dose of radiation. The method comprises the steps of identifying a previously implanted stent or graft within a body lumen. A radiation delivery catheter of the type described elsewhere herein is positioned within the stent or graft, and the balloon is inflated to position the radioactive source against or near the interior wall of the stent or graft. The balloon may either be inflated to a sufficient pressure to further dilate the stent or graft, or inflated sufficiently to position the radiation source against the interior wall of the stent or graft without additional stent or graft expansion or sizing. Additionally, the radiation delivery catheter may provide differing levels of radiation to the edges of the stent and the body of the stent. Following delivery of a dose of radiation, the balloon is deflated and removed from the patient.

Any of the foregoing methods may be accomplished either with or without the perfusion capability disclosed elsewhere herein. In addition, any of the foregoing methods may be accomplished through the use of an over the wire embodiment of the invention or a rapid exchange embodiment of the invention as has been disclosed elsewhere herein.

Thus, in accordance with the present invention, there is provided a catheter having a radiation delivery layer on the balloon, which permits a relatively low energy thin film source to be positioned directly against, or within about 0.001 to 0.003 inches from the vascular wall, depending upon the thickness of any outer sleeve 38 or 70 or other coating. In addition, the present configuration expels substantially all blood or other fluids from between the radiation source and the vessel wall, throughout the entire interior circumference of the vessel for the axial length of the balloon. As a consequence, the radiation is not required to penetrate multiple structures as well as blood within the vessel in order to reach the vessel wall. In addition, radiation delivery is essentially uniform throughout the entire circumference of the vessel at the delivery site.

The configuration of the balloon of the present invention is such that the radiation delivery layer does not need to be elastic and can simply be folded with the balloon material into the reduced, insertion profile. Higher radiation dosages than those specifically described herein can be readily achieved, such as through the use of longer dose times and/or higher activity isotopes and/or higher density of the isotope layer and/or more layers of the thin film source.

Dosimetry

As compared to devices in the art which use centered wires, seed trains or radioactive liquid filled balloons, the catheters and methods disclosed herein present several distinct advantages for the both the physician and patient. The catheters and methods described above allow for delivery of a clinically significant dose of radiation into a vessel wall in a relatively short time while using a source having relatively low activity. They also allow for delivery of a substantially uniform dose into the vessel wall, whether or not such delivery is through a stent previously placed in the vessel. Furthermore, they maximize the effective radiation length ("ERL") of the source, that is, the amount of the total length of the source for which the delivered dose is substantially uniform. These characteristics and advantages are described in more detail below.

The devices and methods described below refer to a reference depth in the vessel to which radiation is being delivered. The reference depth is basically a measuring point for determining delivered dose, however, the reference depths discussed below are based in part upon the depth to which the radioactive dose should be delivered to achieve a clinically relevant effect. The reference depth is generally between 0.5 mm and 3 mm into the tissue at the target site, with 1 mm being a preferred reference depth for coronary vessels and 2 mm being a preferred reference depth for vessels in the peripheral vasculature.

The catheters and methods discussed below preferably use catheter and source technologies described above. However, these preferred technologies should not be viewed as placing limits on either the catheters and methods described in the discussion below or on the attached claims.

In one aspect of the present invention, a radiation delivery catheter has a source that delivers a substantially uniform dose of radiation at a reference depth in the vessel wall. The reference depth is preferably at least 0.7 mm, with depths of about 1 mm being preferred for coronary vessels and a greater depth (about 2 mm) being preferred for peripheral vessels. The dose delivered at the reference depth is substantially uniform over at least 30% and as high as 99% or more of the axial length of the source. The source is preferably substantially uniform over at least 40%, 50%, 60%, 70%, 75%, 80%, 85%, 90%, 95%, 99% or more of its length, with the higher percentages of uniformity being more preferred. The substantially uniform dose may be delivered into the vessel wall through a stent implanted in the vessel wall, or the dose may be delivered into a vessel without a stent therein.

Preferably, the radioactive source delivers a dose of at least about 5 Gy at a reference depth of about 1 mm into the tissue in no more than about 15 minutes. This embodiment is especially preferred for delivery of radiation to a site in a coronary vessel, such as a coronary artery. The delivered dose may be 5 Gy to 30 Gy or more, such as 8 Gy, 10 Gy, 12 Gy, 15 Gy, 20 Gy, 25 Gy, 30 Gy or more, depending upon the desired clinical result. The required time for delivering the dose may be a time period of less than 15 minutes, such as no more than 12 minutes, 10 minutes, 8 minutes, 6 minutes or less.

In another embodiment of catheter, the catheter has a radioactive source which delivers a dose of at least about 6 Gy at a reference depth of about 2 mm into the tissue over a time period of no more than about 40 minutes. This embodiment is useful for delivery of radiation to a site in a vessel larger than most coronary vessels as is more commonly found in the peripheral vasculature. The large vessel dose may be at least about 8 Gy, 10 Gy, 12 Gy, 15 Gy, or more depending upon the desired clinical result. Similarly, the delivery time for the dose is preferably less than 40 minutes, such as less than about 30 minutes, 25 minutes, 20 minutes, 15 minutes or less.

In a preferred method of the present invention, a vessel is treated to inhibit restenosis of the vessel. The treatment may be done in a vessel without a stent therein, or the treatment may be done in-stent, either in an already implanted stent or within a stent carried and/or implanted by the source catheter or another catheter during the same procedure. In one embodiment, the method comprises delivering radiation at a dose of at least about 5 Gy at a reference depth of about 1 mm into the tissue of the vessel wall over a time frame of no more than about 15 minutes. Other preferred embodiments include those in which the dose is increased and/or the time period is decreased, as discussed above in reference to a catheter. Again, this preferred combination of dose/depth/time is especially preferred for coronary vessel applications. For treatment of larger vessels, the method preferably comprises delivering, to a reference depth of about 2 mm, a dose of radiation of 6 Gy or more over a time period of 40 minutes or less, more preferably 20–30 minutes. The doses greater than 6 Gy are preferred, with dosages of 8 Gy, 12 Gy, 15 Gy, or more being among the more preferred dosages for peripheral vessel applications.

In accordance with another preferred embodiment of the present invention, there is provided a method of optimizing the intraluminal radiation delivery profile by minimizing the variation in dose delivered at a reference depth. A delivered dose having a reduced or minimal amount of variation along the length of the treatment site allows for all the tissue which was to be treated in the treatment area to receive a similar dose. Because this dose is preferably that which has been chosen as effective for treating the vessel, and all relevant portions of the vessel have thus received the dose, this result is considered to be optimized. The method itself comprises exposing a vessel to radiation from a source, such that the variation in dose delivered along the length of the source preferably does not exceed about 20%. In more preferred embodiments, the variation in dose delivered along the length of the source is 15% or less, or 10% or less. The preferred range for the reference depth, as discussed above, is between 0.5 to 3 mm into tissue, with a reference depth of 1.0 mm being preferred for coronary vessel applications and 2.0 mm being preferred for larger or peripheral vessels.

As discussed elsewhere, for some embodiments of the present invention, the sources are intentionally non-uniform, having either an extended effective radiation length or a lower length such as in stepping sources. For such non-uniform sources, the discussion in the paragraph above is meant to apply to those areas in which the source is designed to be relatively uniform, such as in the center region of a stepping source.

The foregoing doses can be delivered by the devices of the present invention, using a lower source activity than the activity required in the prior art designs to deliver the same dose over the same time. In one preferred embodiment, a source 33 mm in length and 3.0 mm in diameter has an activity of about 32 mCi. In an alternate embodiment for use in larger vessels (e.g. SVG anastomoses) or those in the peripheral vasculature, the source is 60 mm long and 6.0 mm in diameter with an activity of 155.2 mCi. Both of these sources have an activity of about 0.103 mCi/mm$^2$.

The preferred activities may also be expressed in a manner normalized to the area of the source. In such cases the activity is preferably about 0.050 mCi/mm$^2$ to about 1.000 mCi/mm$^2$, more preferably about 0.080 mCi/mm$^2$ to 0.120 mCi/mm$^2$. Preferred sources deliver a dose of at least 6 Gy at a reference depth of 1 or 2 mm, with sources delivering higher doses, such as 8 Gy, 10 Gy, 12 Gy, 15 Gy, 20 Gy or more being more preferred. The time for delivering the dose is preferably less than about 40 min, 30 min, 25 min, 20 min, 15 min, 12 min, 10 min, 8 min or less, with shorter times being more preferred.

Another preferred embodiment of the invention is a method of optimizing dose uniformity in a vessel wall behind a stent by minimizing the shadow formed by the stent at a reference depth. The preferred reference depths are as discussed above for other embodiments of the present invention. This method comprises placing a radiation delivery catheter inside the stent in a vessel. The method is not limited by the amount of time that the stent has been in place: the stent may have been implanted for some time, it may have been implanted immediately prior to radiation delivery, or it may be being implanted simultaneously with radiation delivery. The method continues with delivering at least two rays of radiation, preferably beta radiation, into the vessel wall in which a first dose is delivered along a first axis past a first side of a stent strut and into the vessel wall, and a second dose is delivered along a second axis past a second side of the same stent strut and into the wall. The first and second axes converge at a convergence point behind the strut, wherein the convergence point is preferably approximately equal to the reference depth, that is, generally no more than about 3 mm behind the strut (i.e., into the vessel wall), preferably no more than about 2 mm behind the strut and more preferably in the coronary artery application, at about 1 mm depth. The dose delivered at a depth approximately equal to the convergence point is preferably at least about 6 or 8 Gy, and may be 10 Gy, 12 Gy, 15 Gy, 20 Gy or more. The more preferred dosages will be determined in part by the particulars of the treatment site and the desired clinical result. In preferred embodiments, the dose depth profile varies by less than 10% along the length of the source inside the 90% isodose crossing the horizontal plane.

In the above embodiments, variables such as the dose delivered, the activity of the source, and the treatment time may be chosen by the physician in view of the particular circumstances of the lesion or site to be treated. It should be noted that catheters and methods having delivered dosages lying outside the above-listed amounts may be used, with the maximum dose being limited by the upper end of the allowable surface dose. The upper allowable surface dose is that which may be delivered to the vessel wall without causing necrosis or other adverse response in the tissue. Because the tissue closest to the source (the interior of the vessel) is most susceptible to overdosing, one may consider spacing back a source, as discussed above, if the surface dose would otherwise fall in the necrotic zone to achieve the desired delivered dose below the surface in the desired time.

Experimental Results

Several catheters according to preferred embodiments of the present invention were made and tested to reveal dosimetry properties. Numerical point dose kernel calculations for cylindrical shell P-32 sources with diameters ranging from the vessel diameter down to a diameter of 0.5 mm were performed to obtain the dose distributions for the range from fully expanded sources to fully unexpanded (deflated), refolded sources. The dose distributions were plotted as depth dose curves and dose profiles along the source length. Additionally, transaxial radiochromic film measurements of the dose distributions surrounding the sources were done in a Lucite phantom, both with and without a 3.0 mm AVE stent.

The catheters used in the testing comprised P-32 thin film sources comprising a substrate (the balloon), tie layer, metal salt and isotope having a coating layer thereon, mounted on an inflatable balloon The balloon sources measured 3.5 mm by 33 mm (diameter by length) being used in the non-stent tests and 2.5 mm by 33 mm being used for the in-stent tests.

The inflated balloon dose was found to be approximately 3.5 Gy/min at a reference depth of 1.0 mm for a source activity density of 100 $\mu$Ci/mm$^2$, independent of source diameter or length. There was good agreement between the experimental measurements and the calculated doses. When inflated, the surface dose of the balloon was 6.1 times greater than at the reference depth (1.0 mm), but only two times greater than that delivered at 130 microns (the stent thickness) from the surface. When the 3.5 mm balloon was deflated, the dose rate at the reference depth was reduced by only about 25% and the vessel surface dose was reduced by about half. For a 2.5 mm balloon, the dose rate at the reference depth was reduced by only about 16%. Stent attenuation reduced the dose of the 3.5 mm balloon at the reference depth by less than 15% (less than 12% for the 2.5 mm balloon), with no discrete shadowing by the stent struts being observed when the source was inflated, although there was some minimal shadowing seen at 0.5 mm depth when the source was deflated. These results indicate that the benefits of high dosing, short treatment times, and minimal stent shadowing will be maintained even if the balloon is deflated frequently during treatment, such as may be done when non-perfusion catheter embodiments are used so as to allow for the passage of blood.

Figure 15:
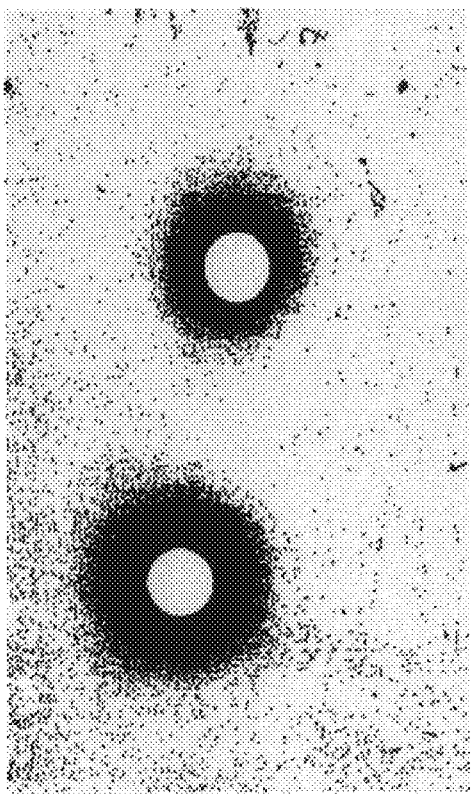
FIG. 15 illustrates the dose delivered by an inflated and a deflated balloon source according to a preferred embodiment of the present invention in a Lucite phantom.

FIGS. 15, 16a–d, and 17 provide some of the results discussed above. Referring to FIG. 15, films from the Lucite phantom testing are presented. In the phantom, the films are placed perpendicular to the tubular body of the catheter (and the balloon having the source thereon) so as to measure the radiation delivered radially outward from the source. This demonstrates how the radiation dose would be delivered into the tissue in the walls of a vessel during treatment. For both the inflated and deflated balloons, the delivered dose is fairly symmetrical, and it can be seen that the amount of radiation delivered by the deflated balloon is a substantial portion of that which is delivered by the inflated balloon.

Figure 16A:
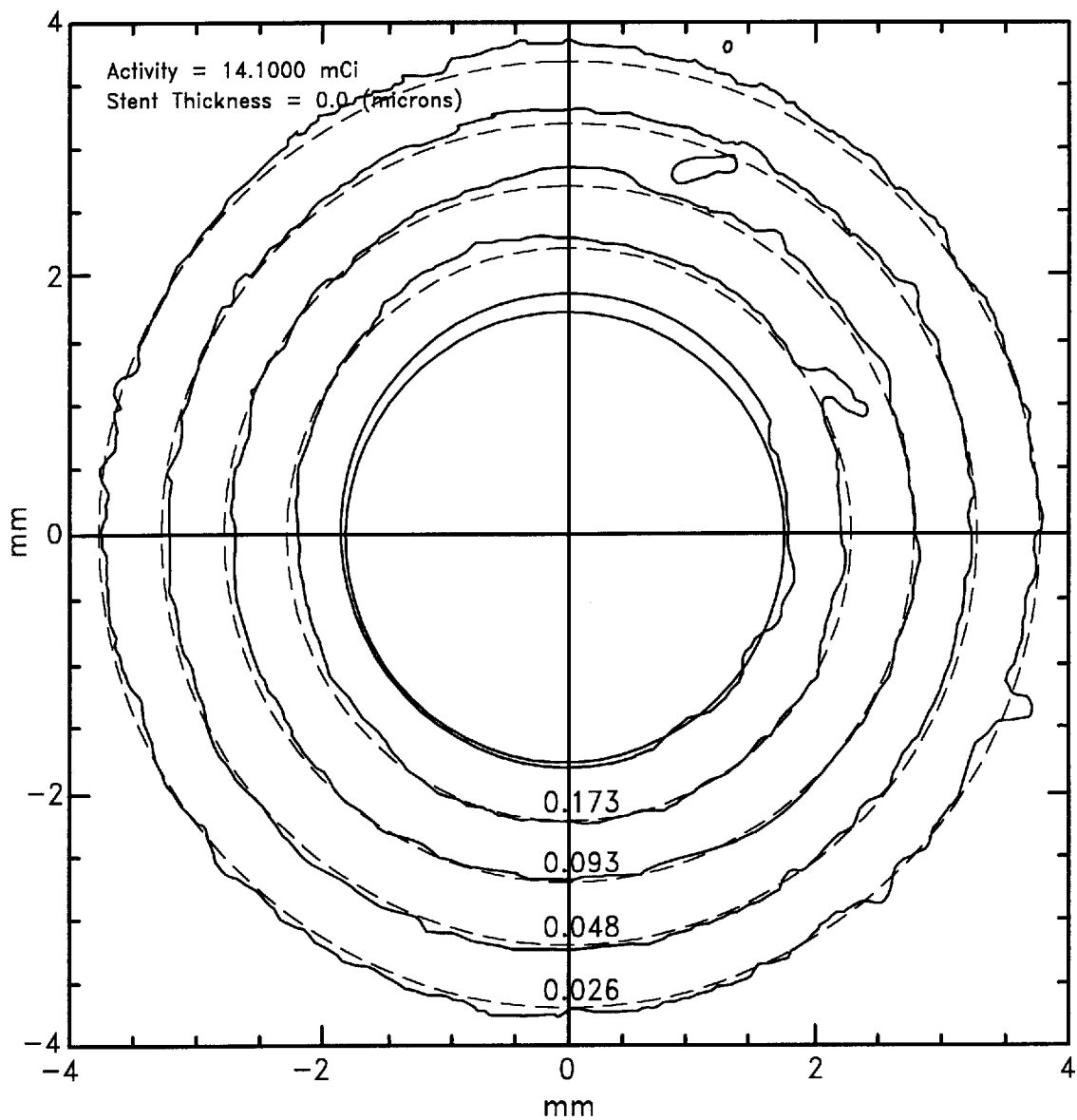
FIGS. 16a and 16c show the dose contours at various reference depths in a phantom and 16b and 16d plot dose versus depth from the vessel surface both without a stent (16a, 16b) and with a stent (16c, 16d).
Figure 16B:
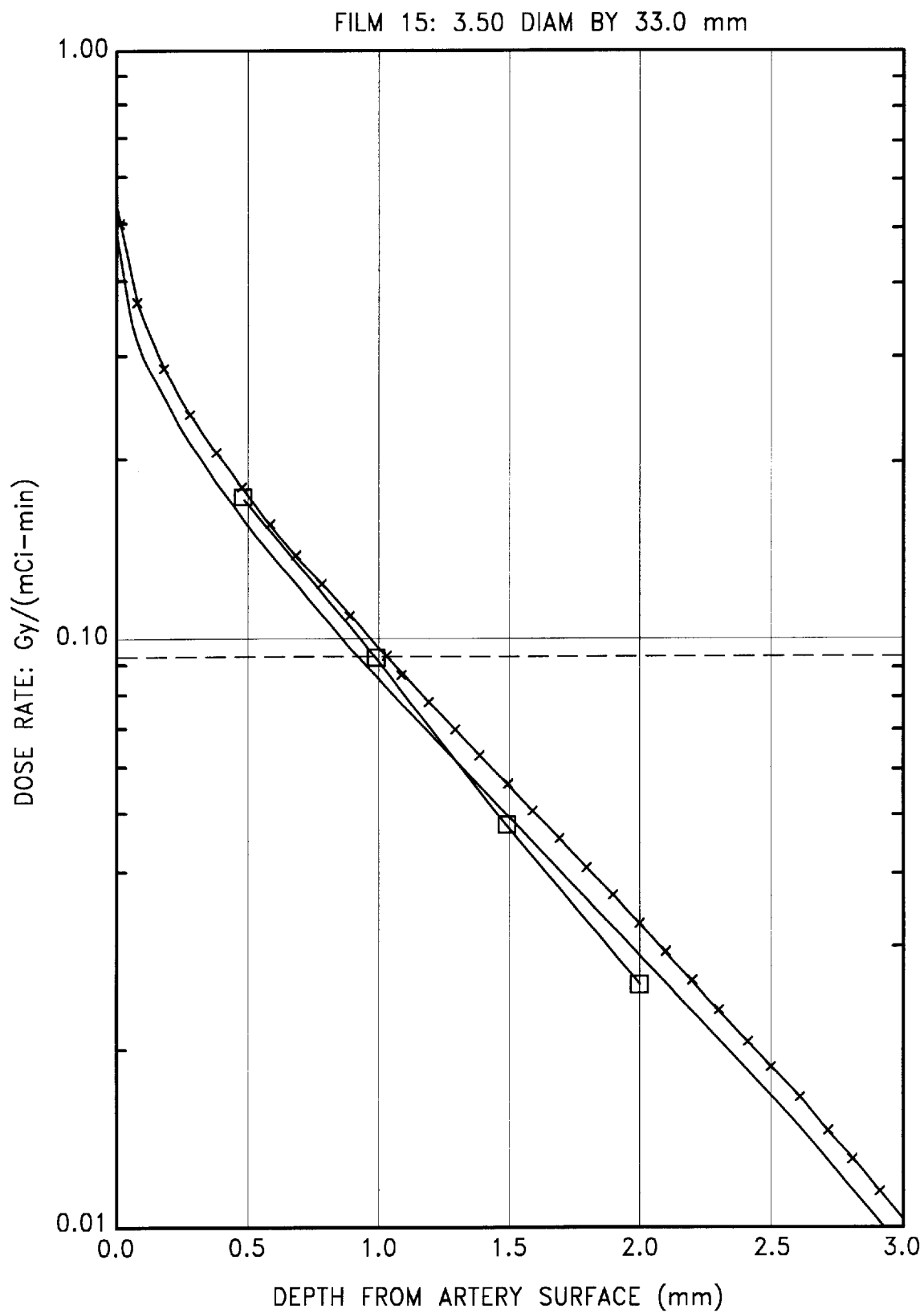
Figure 16C:
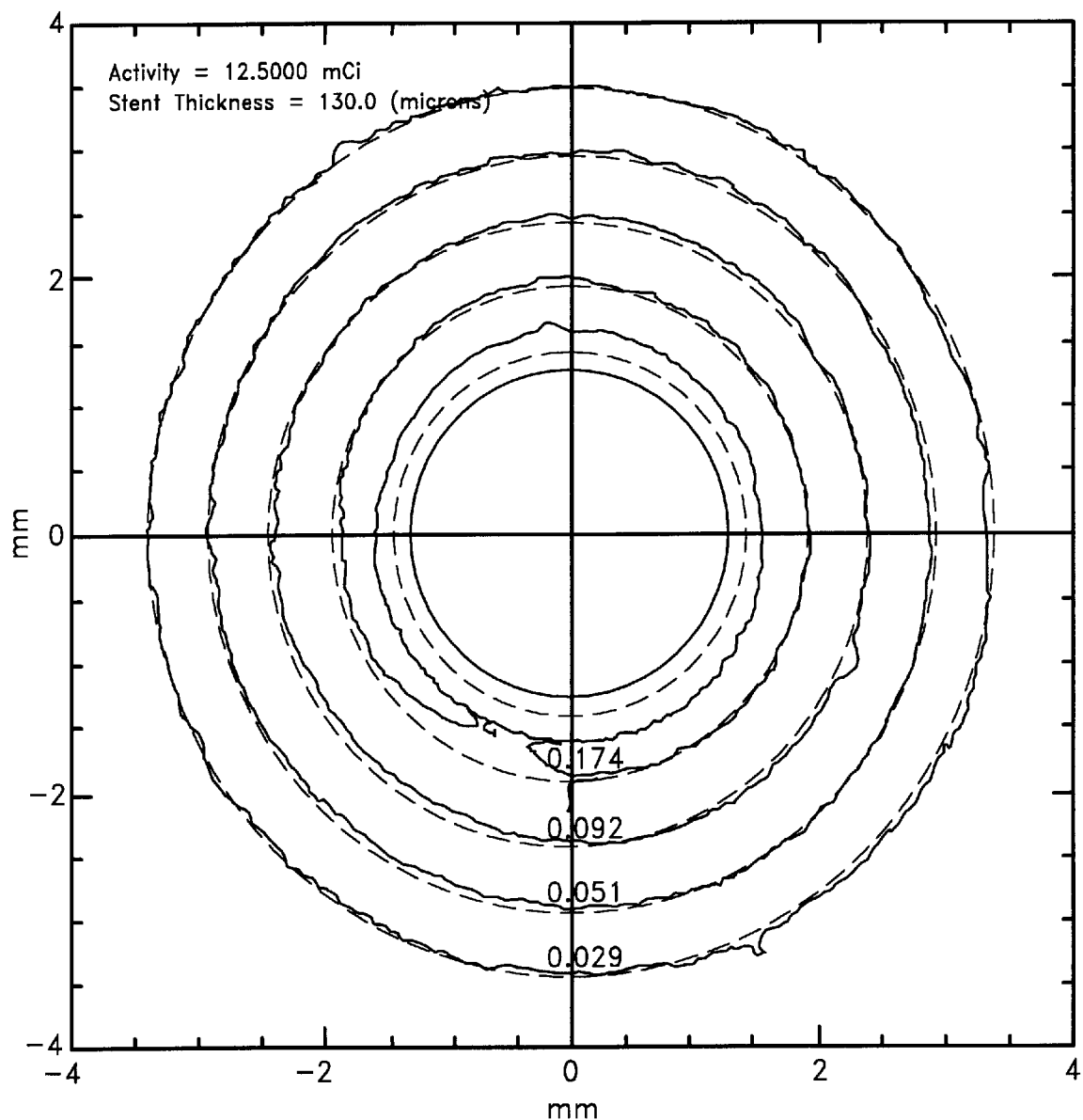
Figure 16D:
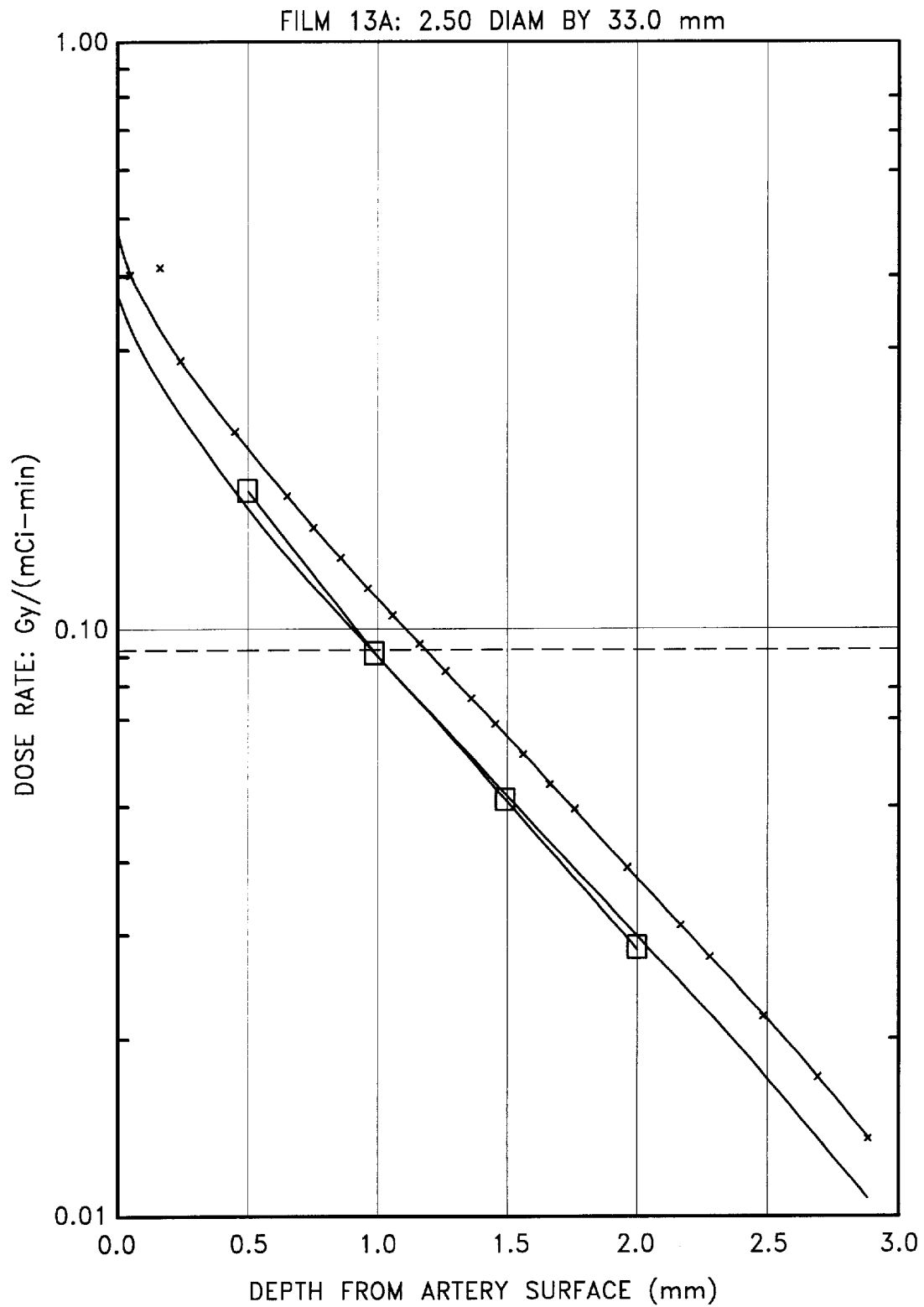

Referring to FIGS. 16a and 16c, the film dose contours show that the dose delivered by the catheters are relatively uniform. hi FIG. 16c, showing the results of the in-stent testing, there is no noticeable shadowing from the stent seen in the dose contours. Additionally, a comparison of FIG. 16d to FIG. 16b demonstrates the more gradual decrease in delivered dose between the surface of the vessel and the first 0.2 mm or so into the vessel that is seen when the source is positioned radially inward of the inner surface of the vessel as is the case when the dosing is done in-stent, or when other spacing means or methods are used, such as the spaced-back source embodiment discussed above.

Figure 17:
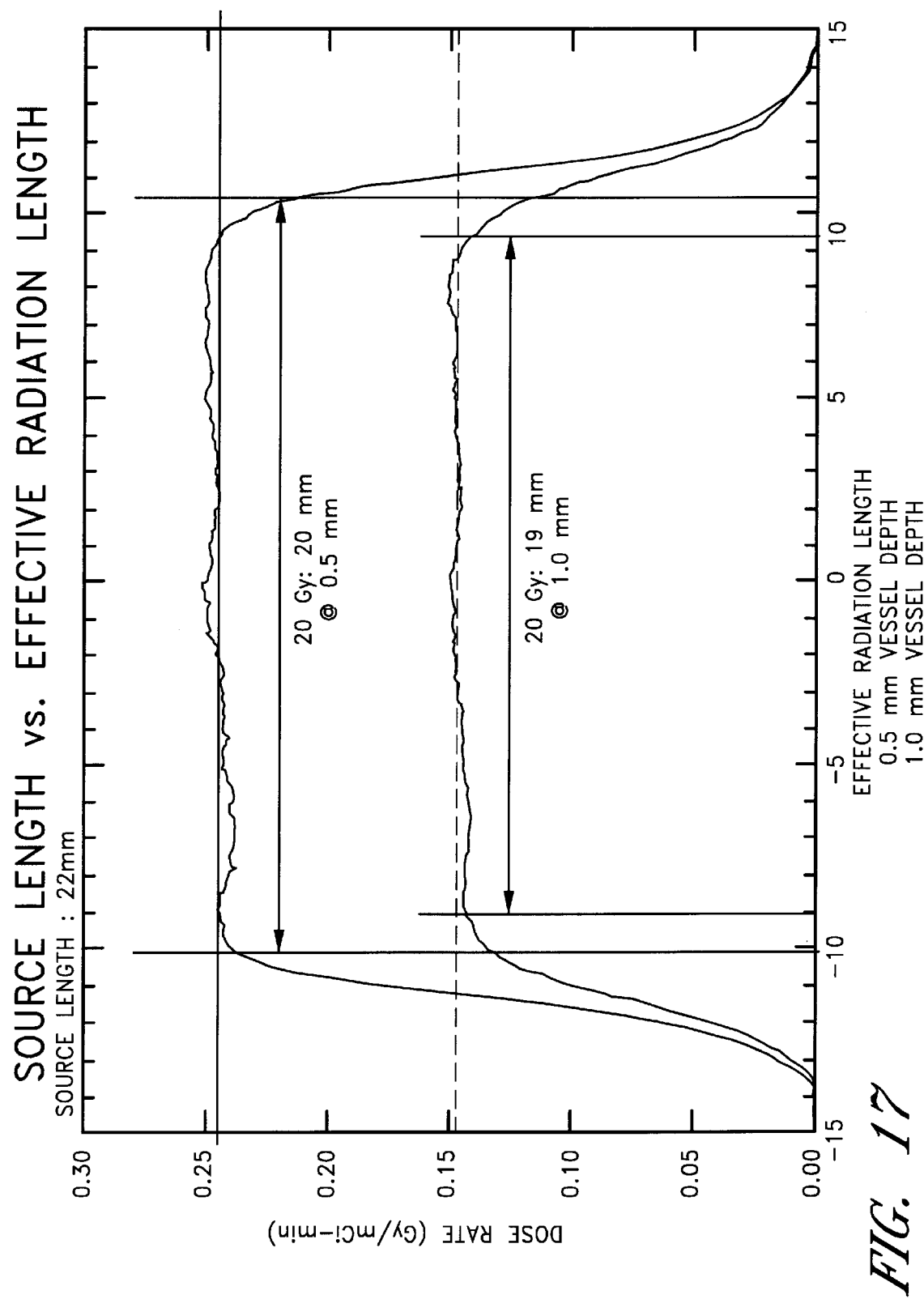
FIG. 17 is a graph showing the dose delivered directly adjacent the surface of the balloon and the dose delivered at a reference depth of 0.5 mm.

In FIG. 17, the two curves plot the dose rate at reference depths of 1.0 mm and 0.5 mm as a function of position on the source. On the horizontal axis, zero marks the center of the balloon-mounted 22 mm long source. It can be seen that the dose rate is substantially uniform over most of the length of the source and trails off near the ends. As discussed above, this tailing off can be minimized if the source used has greater activity in its ends or edges. In FIG. 17, the effective length of the source is calculated using a dose variation of about 10% as the cutoff. Effective lengths can be calculated using other percentage values as the cutoff, depending upon the particular clinical requirements. For the source in FIG. 17, the effective length was about 20 mm at 0.5 mm reference depth and about 19 mm at 1.0 mm reference depth, coming to about 91% and 86% of the length of the source, respectively.

Two alternate embodiments have been studied. In the EERL sources, with non-uniform distribution of activity biased at the ends, the effective radiation length was changed. Using a 1 mm strip at the end of the source in which the activity is increased by 50%, the effective radiation length (1 mm depth, 90% of prescribed dose) for a 33 mm long balloon was increased from 29 mm to 31 mm, in other words from 88% to 94% of the source length. This allows for the treatment of lesions up to 2 mm longer using the same size source without repositioning. Therefore, the inventors contemplate sources in which 90% of the prescribed dose at a depth of 1 mm is delivered over 85% of the source length, preferably over 90% of the source length, with 87%, 89%, 93%, 95%, 97%, and 99% of the source length also being contemplated.

In the stepping sources in which there are 5 mm bands at each end having 50% activity (as compared to the center region), the dosimetry (1 mm depth) indicated that with 3 mm stepping overlap, the dose at the tissue will be between 62% of the prescribed dose to 100% of the dose. These values can be changed based upon the percent activity decrease at the ends and the maximal wall dose which is desired. The inventors contemplate sources having reduced activity bands at the end of the source which are 1 mm–10 mm wide, more preferably 2 mm–5 mm wide being used in methods involving stepping with overlap of such reduced activity bands to achieve a dose in the overlap region of at least 50% of the prescribed dose, more preferably at least 60% of the prescribed dose, with delivered doses of at least 65%, at least 75%, at least 80%, at least 90%, at least 95%, and at least 100% of the prescribed dose also being contemplated.

Comparison with Linear Sources

Figure 18:
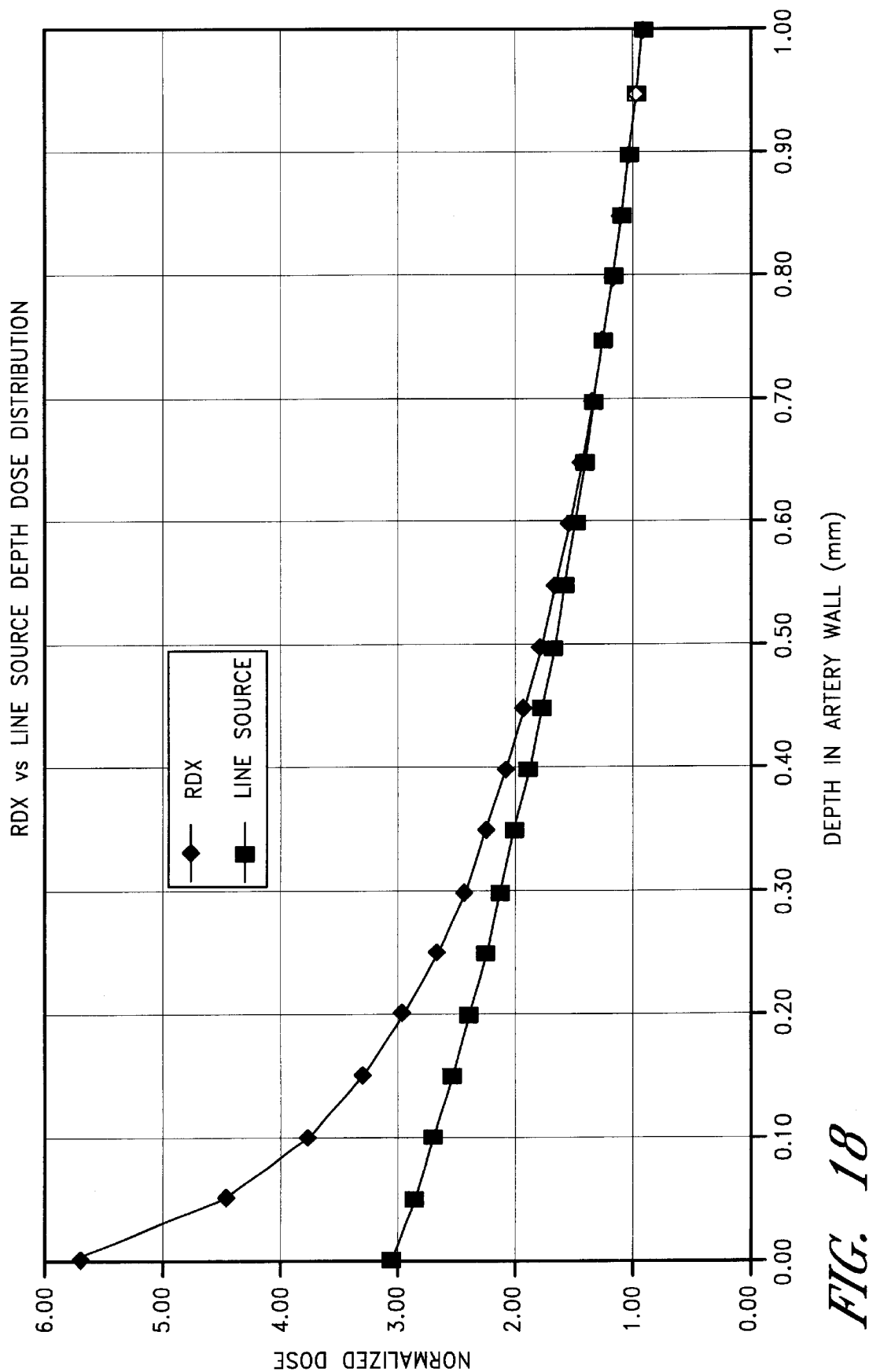
FIG. 18 is a graph showing the dose depth distribution for a generally cylindrical balloon-mounted source embodiment of the present invention and a centered line source.

The balloon-mounted or other generally cylindrical sources according to preferred embodiments of the present invention have several advantages as compared to wire-based or seed train-based line sources known in the art. As discussed earlier, for sources which reside in or near the center of the vessel, the source activity and energy must be high enough to overcome absorption loss encountered as the radiation traverses the lumen of the blood vessel to get to the target tissue site in the vessel wall. The effects of this are shown in FIG. 18, which compares the dose delivered by a generally cylindrical RDX source catheter according to one embodiment of the present invention with a line source. The dose curve for the line source in FIG. 18 assumes that the source is perfectly centered within the vessel lumen, which can be difficult to achieve.

Figure 19:
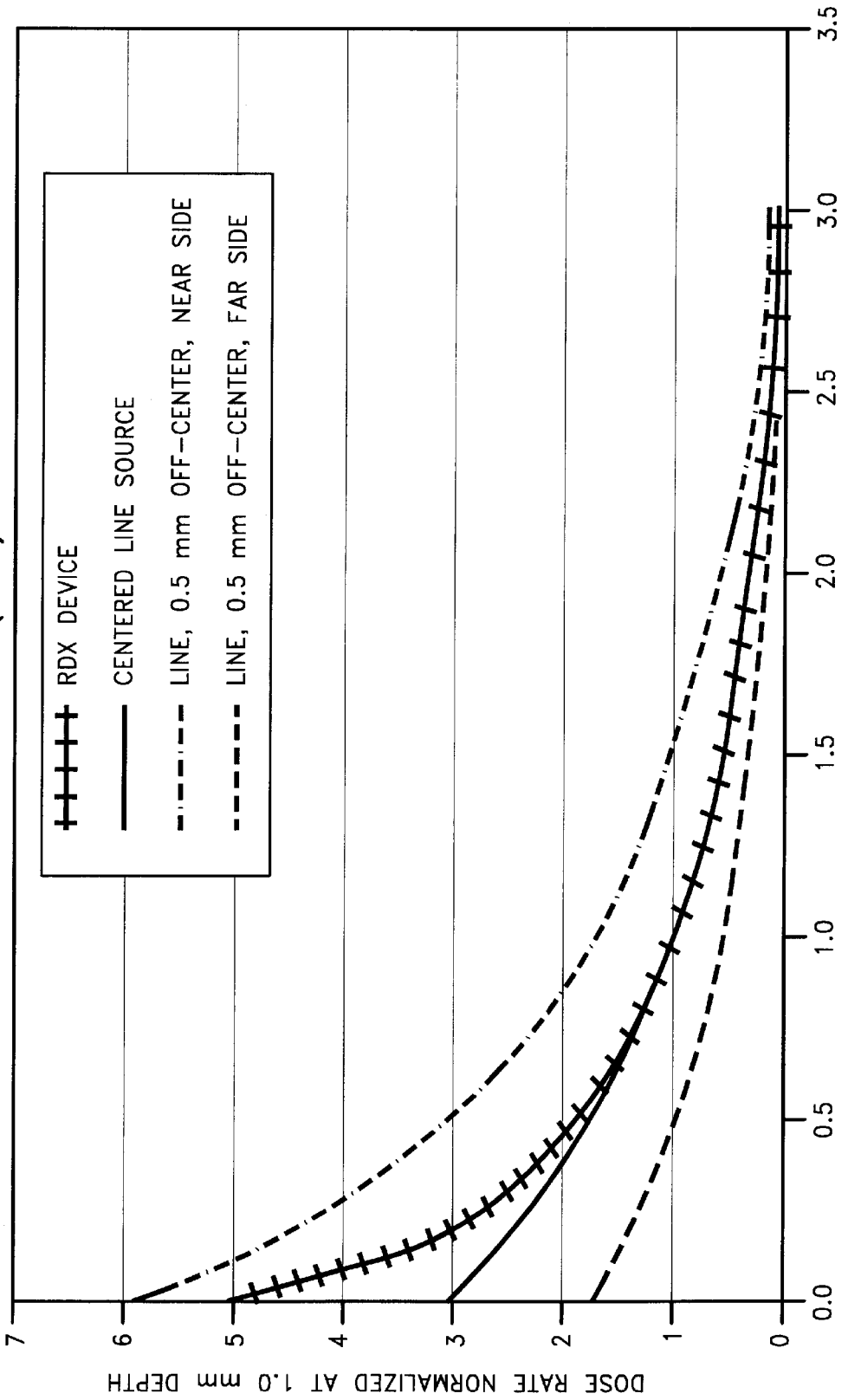
FIG. 19 is a graph showing dosing data for a generally cylindrical balloon-mounted source embodiment of the present invention, a centered line source, and an off-center linear source.

The consequences of a non-centered line source are shown in FIG. 19. The dashed curves in FIG. 19 show the differences in dose rate that are seen when a line source is 0.5 mm off-center in the vessel during treatment. The upper curve shows the dose rate on the side of the vessel to which the wire is closest, where the lower curve shows the dose rate on the side of the vessel which is farther away from the off-center source. This figure shows that, even when the centration of the line source is off by a small amount, the difference in dosing from place to place in the vessel can vary greatly, with much of the vessel receiving either too little dose to be effective or too much dosing so as to cause tissue necrosis.

Figure 20:
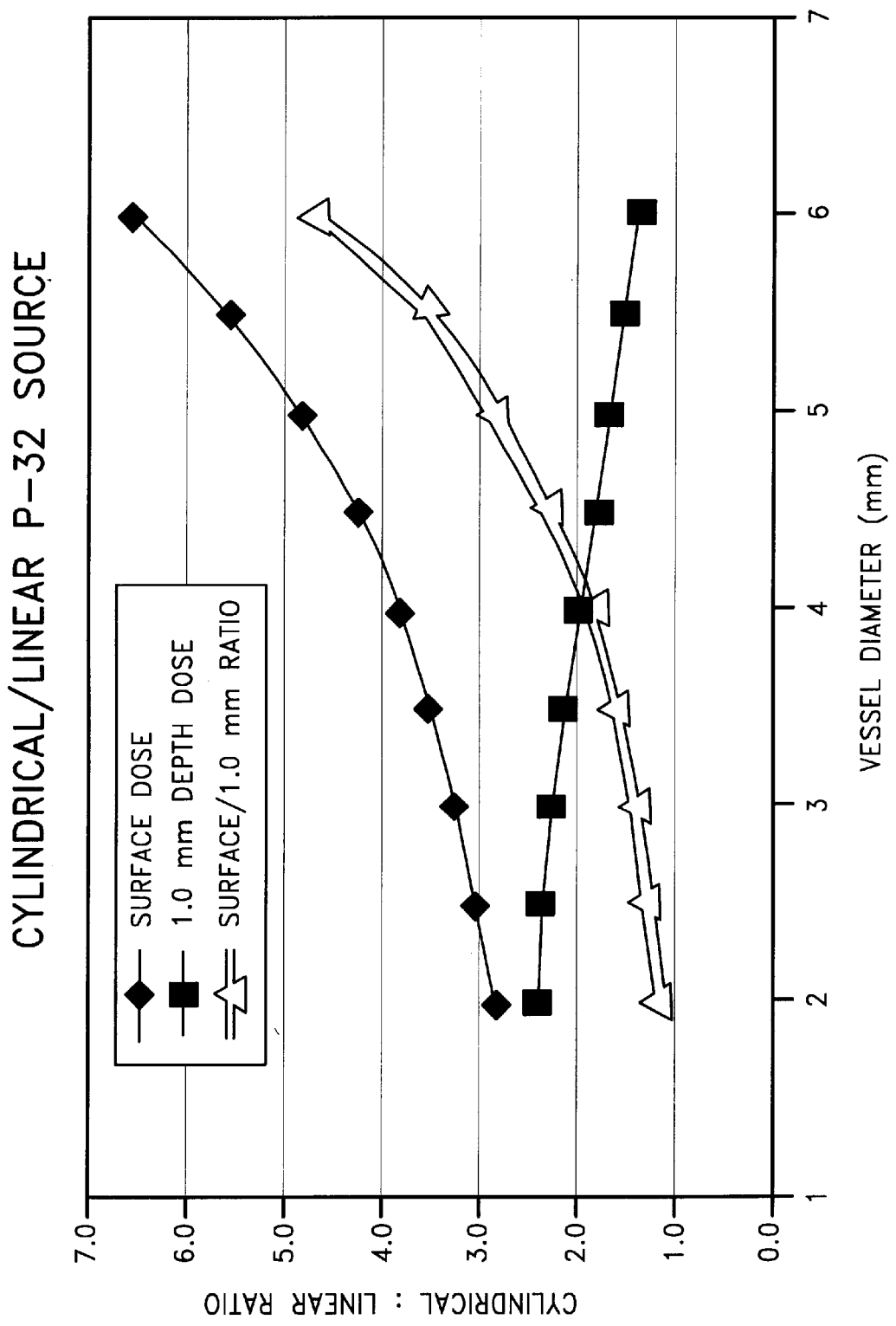
FIG. 20 shows a series of curves comparing dosing in large diameter vessels for a generally cylindrical balloon-mounted source embodiment of the present invention and a centered line source.
Figure 21:
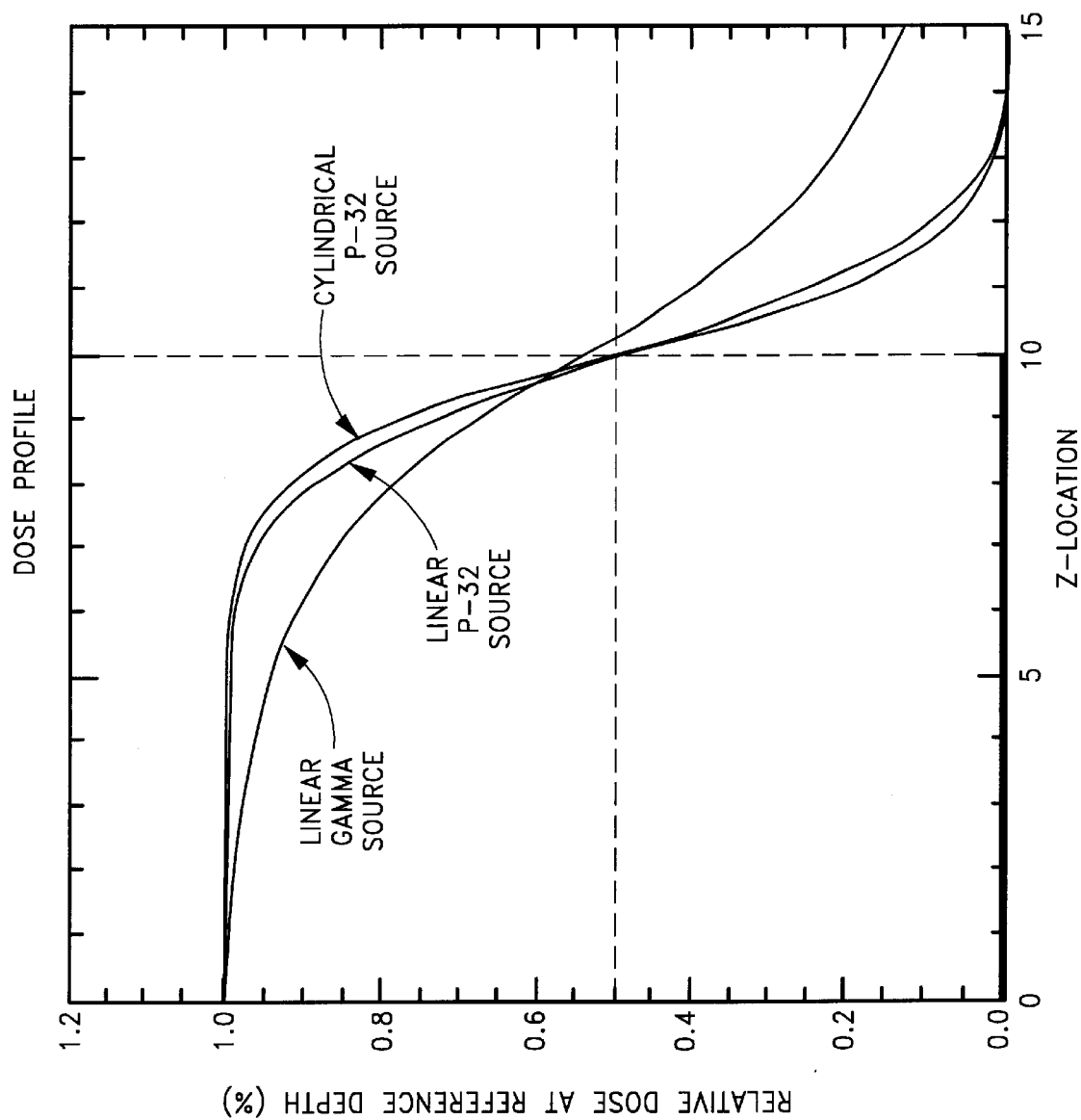
FIG. 21 is a graph comparing relative dose at reference depth for a generally cylindrical balloon-mounted P-32 source embodiment of the present invention, a linear gamma source and a linear P-32 source.
Figure 22:
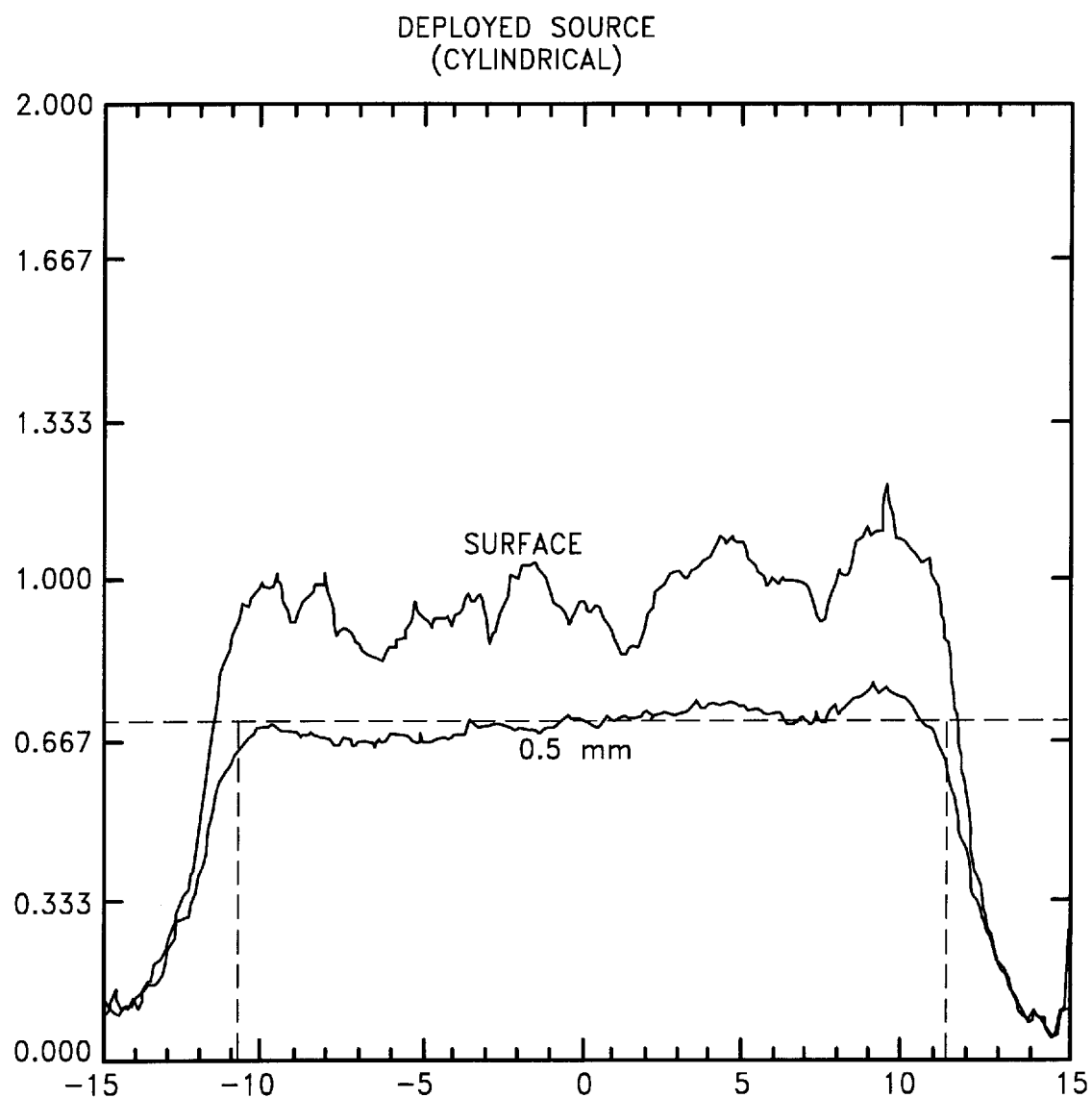
FIG. 22 shows the relative dose for a generally cylindrical balloon-mounted source embodiment of the present invention at the surface of the vessel and at a depth of 0.5 mm into the vessel.

Another advantage of the balloon-mounted or other generally cylindrical sources according to preferred embodiments of the present invention is their ability to provide a clinically significant dose to the surface and reference depth of a larger diameter vessel or hollow organ in the body while maintaining a reasonably low activity. Line sources must have an extremely high activity in order to provide a significant dose to a larger vessel, due in large part to the geometry of the source. The difference between the sources according to preferred cylindrical embodiments of the present invention and those of a linear source can be seen in FIG. 20.

Higher activity and energy sources, however, can have undesirable consequences. First, the likelihood of radiation inadvertently affecting untargeted tissue is higher because the absorption factor per unit tissue length is lower. Second, the higher activity and energy sources are more hazardous to the medical staff and thus require additional shielding during storage and additional precaution during use. In addition, the source of any activity or energy may or may not be exactly in the center of the lumen, so the dose calculations are subject to error factors due to non-uniformity in the radial distance from the source surface to the target tissue. The impact of these factors is a common topic of discussion at recent medical conferences addressing Intravascular Radiation Therapy, such as the Trans Catheter Therapeutics conference, the Scripps Symposium on Radiotherapy, the Advances in Cardiovascular Radiation Therapy meeting, the American College of Cardiology meeting, and the American Heart Association Meeting.

The impact on treatment strategy is discussed in detail in a paper discussing a removable seed system similar to the ones disclosed above (Tierstein et al., Catheter based Radiotherapy to Inhibit Restenosis after Coronary Stenting, NEJM 1997; 336(24):1697–1703). Tierstein reports that Scripps Clinic physicians inspect each vessel using ultrasonography to assess the maximum and minimum distances from the source center to the target tissue. To prevent a dose hazard, they will not treat vessels where more than about a 4×differential dose factor (8–30 Gy) exists between the near vessel target and the far vessel target. Differential dose factors such as these are inevitable for a catheter in a curvilinear vessel such as an artery, and will invariably limit the use of radiation from conventional wire and seed train sources and add complexity to the procedure. Moreover, the paper describes the need to keep the source in a lead transport device called a "pig", as well as the fact that the medical staff leaves the catheterization procedure room during the treatment. Thus added complexity, time and risk is added to the procedure caused by variability of the position of the source within the delivery system and by the activity and energy of the source itself.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. A method of optimizing an in stent radiation delivery profile, comprising the steps of:
   identifying a stent positioned against the wall of a vessel;
   positioning a radiation source within the stent; and
   exposing the vessel to radiation through the stent such that variations in the dose delivered to a reference depth of at least about 1 mm in the wall of the vessel along the length of the source do not exceed about 20%.

2. A method of optimizing an in stent radiation delivery profile as in claim 1, wherein the variations in the dose delivered to the reference depth in the wall of the vessel along the length of the source do not exceed about 15%.

3. A method of optimizing an in stent radiation delivery profile as in claim 1, wherein the positioning a radiation a source step comprises positioning a source having an activity of no greater than about 60 mCi, and the average dose delivered to a depth of about 1 mm in the wall of the vessel is at least about 8 Gy.

4. A method of optimizing an in stent radiation delivery profile as in claim 3, wherein the exposing step is accomplished in no more than about 15 minutes.

5. A method of optimizing an in stent radiation delivery profile as in claim 4, wherein the exposing step is accomplished in no more than about ten minutes.

6. A method of optimizing an in stent radiation delivery profile as in claim 5, wherein the exposing step is accomplished in no more than about eight minutes.

7. A method of optimizing an in stent radiation delivery profile as in claim 1, wherein the positioning a radiation a source step comprises positioning a source having an activity of no greater than about 200 mCi, and the average dose delivered to a reference depth of about 2 mm in the wall of the vessel is at least about 6 Gy.

8. A method of optimizing an in stent radiation delivery profile as in claim 7, wherein the exposing step is accomplished in no more than about 40 minutes.

9. A method of optimizing an in stent radiation delivery profile as in claim 8, wherein the exposing step is accomplished in no more than about 30 minutes.

10. A method of optimizing an in stent radiation delivery profile as in claim 9, wherein the exposing step is accomplished in no more than about 20 minutes.

11. A method of optimizing radiation dose uniformity in a vessel wall behind a stent, comprising the steps of:
    positioning a radiation delivery catheter within a stent in a body vessel;
    delivering a first dose of beta radiation along a first axis past a first side of a stent strut and into the vessel wall; and
    delivering a second dose of beta radiation along a second axis past a second side of the strut and into the vessel wall;
    wherein the first axis and the second axis converge behind the strut.

12. A method as in claim 11, wherein the convergence point is at a depth of no more than about 3 mm.

13. A method as in claim 12, wherein the convergence point is at a depth of no more than about 2 mm.

14. A method as in claim 11, wherein a dose of at least about 8 Gy is delivered at a depth of about 1 mm.

15. A method as in claim 11, wherein the dose depth profile varies by less than 10% along the length of the source inside the 90% isodose crossing of the horizontal plane.

16. A method of optimizing an intraluminal radiation delivery profile, comprising the steps of:
    identifying a treatment site in the wall of a vessel;
    positioning a radiation source against the wall; and
    exposing the vessel to radiation such that variations in the dose delivered to a reference depth of at least about 1 mm in the wall of the vessel along the length of the source do not exceed about 20%.

17. A method of optimizing an intraluminal radiation delivery profile as in claim 16, wherein the variations in the dose delivered to a reference depth of at least about 1 mm in the wall of the vessel along the length of the source do not exceed about 15%.

18. A method of optimizing an intraluminal radiation delivery profile as in claim 16, wherein the positioning a radiation a source step comprises positioning a source having an activity of no greater than about 60 mCi, and the average dose delivered to a depth of about 1 mm in the wall of the vessel is at least about 8 Gy.

19. A method of optimizing an intraluminal radiation delivery profile as in claim 18, wherein the exposing step is accomplished in no more than about 15 minutes.

20. A method of optimizing an intraluminal radiation delivery profile as in claim 18, wherein the exposing step is accomplished in no more than about ten minutes.

21. A method of optimizing an intraluminal radiation delivery profile as in claim 18, wherein the exposing step is accomplished in no more than about eight minutes.

22. A method of optimizing an intraluminal radiation delivery profile as in claim 16, wherein the positioning a radiation a source step comprises positioning a source having an activity of no greater than about 200 mCi, and the average dose delivered to a depth of about 2 mm in the wall of the vessel is at least about 6 Gy.

23. A method of optimizing an intraluminal radiation delivery profile as in claim 22, wherein the exposing step is accomplished in no more than about 40 minutes.

24. A method of optimizing an intraluminal radiation delivery profile as in claim 22, wherein the exposing step is accomplished in no more than about 30 minutes.

25. A method of optimizing an intraluminal radiation delivery profile as in claim 22, wherein the exposing step is accomplished in no more than about 20 minutes.

26. A method of treating a site in a vessel, comprising delivering radiation from a source having an activity of no more than about 200 mCi at a dose of at least about 8 Gy, at a depth of 1 mm into the vessel wall, over a time of no more than about 15 minutes.

27. A method of treating a vessel as in claim 26, wherein the time is no more than about 10 minutes.

28. A method of treating a vessel as in claim 26, wherein the time is no more than about 8 minutes.

29. A method of treating a vessel as in claim 26, wherein variations in the delivered dose at a depth of 1 mm do not exceed about 20%.

30. A method of treating a vessel as in claim 29, wherein variations in the delivered dose at a depth of 1 mm do not exceed about 15%.

31. A method of treating a vessel as in claim 26, wherein the delivering step comprises delivering radiation from a source having an activity of no more than about 60 mCi.

32. A method of treating a vessel as in claim 26, wherein the delivering step comprises positioning a source against the vessel wall.

33. A method of treating a vessel as in claim 32, wherein the positioning step is accomplished by inflating a balloon.

34. A method of treating a vessel as in claim 33, further comprising the steps of deflating the balloon to permit perfusion and reinflating the balloon.

35. A method of treating a vessel as in claim 33, wherein the source is attached to the balloon.

36. A method of treating a vessel as in claim 26, wherein the site is in a coronary artery.

37. A method of treating a vessel as in claim 26, wherein the site is in a coronary artery bypass graft.

38. A method of treating a site in a vessel, comprising delivering radiation from a source having an activity of no more than about 60 mCi at a dose of at least about 8 Gy, at a depth of 1 mm into the vessel wall, over a time of no more than about 15 minutes.

39. A method of treating a vessel as in claim 38, wherein the time is no more than about 10 minutes.

40. A method of treating a vessel as in claim 38, wherein variations in the delivered dose at a depth of 1 mm do not exceed about 20%.

41. A method of treating a vessel as in claim 38, wherein variations in the delivered dose at a depth of 1 mm do not exceed about 15%.

42. A method of treating a vessel as in claim 38, wherein the delivering step comprises positioning a source against the vessel wall.

43. A method of treating a site in a vessel, comprising delivering radiation to a site in a coronary artery bypass graft at a dose of at least about 8 Gy, at a depth of 1 mm into the vessel wall, over a time of no more than about 15 minutes.

44. A method of treating a vessel as in claim 43, wherein the time is no more than about 10 minutes.

45. A method of treating a vessel as in claim 43, wherein variations in the delivered dose at a depth of 1 mm do not exceed about 20%.

46. A method of treating a vessel as in claim 43, wherein the delivering step comprises delivering radiation from a source having an activity of no more than about 200 mCi.

47. A method of treating a vessel as in claim 43, wherein the delivering step comprises positioning a source against the vessel wall.

* * * * *